US007214858B2

(12) United States Patent
Caimi et al.

(10) Patent No.: US 7,214,858 B2

(45) Date of Patent: May 8, 2007

(54) PLANT GENES ENCODING TREHALOSE METABOLISM ENZYMES

(75) Inventors: Perry G. Caimi, Kennett Square, PA (US); Saverio Carl Falco, Arden, DE (US); Zude Weng, Des Plaines, IL (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 10/365,970

(22) Filed: Feb. 13, 2003

(65) Prior Publication Data

US 2004/0229364 A1 Nov. 18, 2004

Related U.S. Application Data

(63) Continuation-in-part of application No. 09/538,365, filed on Mar. 29, 2000, now abandoned.

(60) Provisional application No. 60/127,187, filed on Mar. 31, 1999.

(51) Int. Cl.

| | |
|---|---|
| ***A01H 5/00*** | (2006.01) |
| ***A01H 5/10*** | (2006.01) |
| ***C12N 15/82*** | (2006.01) |
| ***C12N 15/55*** | (2006.01) |

(52) U.S. Cl. .................. 800/298; 800/278; 435/320.1; 536/23.2; 424/93.2

(58) Field of Classification Search ................ 800/278, 800/298; 536/23.2, 23; 435/320.1, 70.1; 424/93.2

See application file for complete search history.

(56) References Cited

U.S. PATENT DOCUMENTS 6,686,516 B2 2/2004 Lebel et al.

FOREIGN PATENT DOCUMENTS

EP 1 002 867 A1 5/2000

OTHER PUBLICATIONS

Vogel, G. et al., Accession No. AF007778, Mar. 9, 1998.*

Romero, C. et al., "Expresison of the yeast trehalose-6-phosphate synthase gene in transgenic tobacco plants: pleiotropic phenotypes include drought tolerance." 1997, Planta, vol. 201, pp. 293-297.*

Lazar, E. et al., "Transforming Growth Factor a: Mutation of Aspartic Acid 47 and Leucine 48 Results in Different Biological Activities." 1988, Molecular and Cellular Biology, vol. 8, pp. 1247-1252.*

Broun, P. et al., "Catalytic Plasticity of Fatty Acid Modification Enzymes Underlying Chemical Diversity of Plant Lipids." 1998, Science, vol. 282, pp. 1315-1317.*

Hill, M. A. and Preiss, J. ,"Vunctional Analysis of Conserved Histidines in ADP-Glucose Pyrophosphorylase from *Escherichia coli*." 1998, Biochemical and Biophysical Research Communications, vol. 244, pp. 573-577.*

Bowie, J. U. et al., "Deciphering the Message in Protein Sequences: Tolerance to Amono Acid Substitutions." 1998, Science, vol. 247, pp. 1306-1310.*

Guo et al, 2004, Proc. Natl. Acad. Sci. USA 101: 9205-9210.*

Schluepmann et al, 2004, Plant Physiol. 135:879-890.*

George F. Kalf et al., The purification and properties of trehalase, J. Biol. Chem. 230:691-698, 1958.

National Center for Biotechnology Information General Identifier No. 2944178, Accession No. AAC39369, Mar. 9, 1998, G. Vogel et al., Trehalose-6-phosphate phosphatases from *Arabidopsis thaliana*: identification by functional complementation of the yeast tps2 mutant.

National Center for Biotechnology Information General Identifier No. 2944180, Accession No. AAC39370, Mar. 9, 1998, G. Vogel et al., Trehalose-6-phosphate phosphatases from *Arabidopsis thaliana*Identification by functional complementation of the yeast tps2 mutant.

National Center for Biotechnology Information General Identifier No. 4559292, Accession No. AAD22970, Apr. 4, 1999, R. A. Aeschbacher et al., Purification of the trehafase GMTRE1 from soybean nodules and cloning of its cDNA. GMTRE1 is expressed at a low level in multiple tissues.

National Center for Biotechnology Information General Identifier No. 3929389, Accession No. 042783, Jun. 15, 2002, C. D'Enfert et al., Neutral trehalases catalyse intracellular trehalose breakdown in the filamentous fungi *Aspergillus nidulans* and *Neurospora crassa*.

Christophe D'Enfert et al., Mol. Microbiol., 32(3):471-473, 1999, neutral trehalases catalyse intracellular trehalose breakdown in the filamentous fungi *Aspergillus nidulans* and *Neurospora crassa*.

National Center for Biotechnology Information General Identifier No. 6553894, Accession No. AAF16560, Oct. 12, 2000, X. Lin et al., *Arabidopsis thallane* chromosome 1 BAC T23K23 genomic sequence.

National Center for Biotechnology Information General Identifier No. 730984, Accession No. P40387, Nov. 1, 1997, M.A. Blazquez et al., Trehalaose-6-P synthase is dispensable for growth on glucose but not for spore germination in *Schizosaccharomyces prome*.

National Center for Biotechnology Information General Identifier No. 6587858, Accession No. AAF 18542. Oct. 12, 2000, X. Lin et al., *Arabidopsis thaliana* chromosome 1 BAC T11/11 genomic sequence.

Miguel A. Blazquez et al., Plant J., 13(5):685-689, 1998, Isolation and molecular characterization of the *Arabidopsis* TPS1 gene, encoding trehalose-6-phosphate synthase.

(Continued)

*Primary Examiner*—Anne Kubelik

(57) ABSTRACT

This invention relates to isolated nucleic acid fragments encoding trehalose metabolism enzymes, more specifically, alpha, alpha-trehalase, alpha, alpha-trehalose-phosphate synthase or trehalose-6-phosphate phosphatase. The invention also relates to the construction of a recombinant DNA construct encoding all or a portion of the alpha, alpha-trehalase, alpha, alpha-trehalose-phosphate synthase or trehalose-6-phosphate phosphatase, in sense or antisense orientation, wherein expression of the recombinant DNA construct results in production of altered levels of the alpha, alpha-trehalase, alpha, alpha-trehalose-phosphate synthase or trehalose-6-phosphate phosphatase in a transformed host cell.

12 Claims, 3 Drawing Sheets

OTHER PUBLICATIONS

Guido Vogel et al., Plant J., 13(5):673-683, 1998, Trehalose-6-phosphate phosphatases from *Arabidopsis thaliana*: Identifiction by Functional complementation of the yeast tps2 mutant.

Karin Lippert et al., Enzyme stabilization by ectoine-type compatible solutes: protection against heating, freezing and drying, Appl. Microbiol. Biotechnol., 37:61-65, 1992.

Hans J. Bohnert et al., Adaptations to Environmental Stresses, Plant Cell, 7:1099-1111, 1995.

Roger A. Aeschbacher et al., Purification of the trehalase GMTRE1 from soybean nodules and cloning of is cDNA. GMTRE1 is expressed at a low level in multiple tissues, Plant Physiol., 119:489-495, 1999.

Miguel A. Blazquez et al., Trehalaose-6-P synthase is dispensable for growth on glucose but not for spore germination in *Schizosaccharomyces pombe*, J. Bacteriol., 176(13):3895-3902, 1994.

* cited by examiner

```
                                                 *
SEQ ID NO:16     1 MDMGSGS-SPVITDPISISPPLLGGLTSNLMP-FSVMSGGCSS-SPS--MSAS--SRRK-
SEQ ID NO:20     1 MDLKP-NLNPVLTDATPLTRSRLG-VPSGLSP-YSPIGAT-FP-HGN--MLAI--PRKKT
SEQ ID NO:22     1 L----VELAMSISN--------TSALPRATVPGIMALLGGVLGLPQKKLLMKTLEDGSVN
SEQ ID NO:24     1 ------------------------------------------------------------
SEQ ID NO:37     1 MDMKSGHSSPVMTDSPPISNSRLT-IRQNRLP-YSSAAATAIS-QNNNLLLTV--PRKKT
SEQ ID NO:38     1 M----TNQNVIVSDRKPILGLKTITVSVSNSPLFSNSFPTYFNFPRRKLL-KLLEAADKN
                   1                                                          60

                                * *  ***                      *     ****  *  *
SEQ ID NO:16    53 --IEEVLVNGLLDAMKSSSPRKKHNLAFGQDNSPDEDPAYTAWLS-KCPSALASFKQIVA
SEQ ID NO:20    52 GILDDFRSSGWLDAMKSSSPTHTKVSKDVSHGIGSPDSAYSTWL-LKFPSALASFDQITN
SEQ ID NO:22    49 K-GGTKVINTWIDSMRASSPTRVKSTQ-----NQDPTS---PWT-LYHPSALSMFDQIVC
SEQ ID NO:24     1 ------------------------------------------------------------
SEQ ID NO:37    56 GILDDVKSNGWLDAMKSSSPPPTILNKD-NLSNDATDMTYREWMQLKYPSALTSFEKIMS
SEQ ID NO:38    56 NLVVAPKITSMIDSMRDSSPTRLRSSSYDSDSDNDDKT---SWI-VRFPSALNMFDEIVN
                  61                                                         120

                         *  ************  ** *     **      *  ** **  **   **  *
SEQ ID NO:16   110 NAQGRRIAVFLDYDGTLSPIVDDPDKAFMSPVMRAAVRNVAKYFPTAIVSGRSRKKVFEF
SEQ ID NO:20   111 CAKGKRIALFLDYDGTLSPIVDNPDSAFMSDNMRAAVKIVAEYFPTAIISGRSRDKVYEF
SEQ ID NO:22    99 ESKGKQIVTFLDYDGTLSPIVADPDKAYMSKKMRTTLKDLARHFPTAIVSGRCLDKVYNF
SEQ ID NO:24     1 ------------------------------------RNVAKYFPAAIVSGRSRKKVLEF
SEQ ID NO:37   115 FAKGKRIALFLDYDGTLSPIVEEPDCAYMSSAMRSAVQNVAKYFPTAIISGRSRDKVYEF
SEQ ID NO:38   112 AAKGKQIVMFLDYDGTLSPIVEDPDKAFITHEMREVVKDVASNFPTAIVTGRSIEKVRSF
                  121         LDYDGTLSPIVEEP                                 180
                                 A-Domain
```

FIG. 1A

```
                      *         *********                                         *****   *****   *
SEQ ID NO:16   170 VKLTELYYAGSHGMDIVTSAAAH---ATEKC--------KEANLFQPACEFLPMINEVSK
SEQ ID NO:20   171 VGVSDLCYAGSHGMDIIGPSRQSISDNHPDCISSADKQGVEVNLFQPAAEFLPMINEVLG
SEQ ID NO:22   159 VRLAELYYAGSHGMDIKGPTNKRST-----------KKENEQVLFQPASEFLPMINEVYN
SEQ ID NO:24    24 VKLKELCYAGSHGMDIMTSSSAHYERNAEKG--------KEANLFQPARDFLPMIDEVSK
SEQ ID NO:37   175 VNLSELYYAGSHGMDIMSPAGESLNHEHSRTVSVYE-QGKDVNLFQPASEFLPMIDKVLC
SEQ ID NO:38   172 VQVNEIYYAGSHGMDIEGPTNENSN-----------GQSNERVLFQPAREFLPMIEKVVN
                  181                                                         240

                       * * *     *  ** **** *** * * *  *        *  *    * *  * ** ***
SEQ ID NO:16   219 CLVEVTSSIEGARVENNKFCVSVHYRNVAEKDWKVVAGLVKQVLEAFPRLKVTNGRMVLE
SEQ ID NO:20   231 LLMECTEDIEGATVENNKFCVSVHYRNVDEESWQIVGQRVYDVLKEYPRLRLTHGRKVLE
SEQ ID NO:22   208 ILVEKTKSVPGAKVENNKFCLSVHFRCVDEKSWVSLAEQVSFVLNEYPKLKLTQGRKVLE
SEQ ID NO:24    76 VLLEVTSRIEGASVEDNKFCVSVHYRNVDEKDWELVARLVNEVLEDFPRLKVTNGRMVLE
SEQ ID NO:37   234 SLIESTKDIKGVKVEDNKFCISVHYRNVEEKNWTLVAQCVDDVIRTYPKLRLTHGRKVLE
SEQ ID NO:38   221 ILEEKTKWIPGAMVENNKFCLSVHFRRVDEKRWPALAEVVKSVLIDYPKLKLTQGRKVLE
                  241                                                         300

                       ** * **** *  *** ***        *   * *************      * *****
SEQ ID NO:16   279 VRPVIDWDKGKAVEFLLRSLGLSDSEDVVPIYIGDDRTDEDAFKVLRE-RSCGYGILVSQ
SEQ ID NO:20   291 VRPVIDWDKGKAVTFLLESLGLN-CDDVLAIYVGDDRTDEDAFKVLKEA-NKGCGILVSR
SEQ ID NO:22   268 IRPTIKWDKGKALEFLLESLGYANSDNVFPIYIGDDRTDEDAFKVLRR-RGHGVGILVSK
SEQ ID NO:24   136 VRPVIDWDKGKAVEFLLQSLGLSDSEKVIPIYIGDDRTDEDAFKVLRE-RNCGYGILVSQ
SEQ ID NO:37   294 IRPVIDWDKGKAVTFLLESLGLNNCEDVLPIYVGDDRTDEDAFKVLRDGPNHGYGILVSA
SEQ ID NO:38   281 IRPTIKWDKGQALNFLLKSLGYENSDDVVPVYIGDDRTDEDAFKVLRE-RGQGFGILVSK
                  301                                  GDDRTDEDAF             360
                                                        B-Domain
```

FIG. 1B

```
                   **   * *   **  *  **  *  **
SEQ ID NO:16  338 VPKDTEAFYSVRDPSEVMGFLNSLVRWKK-----HPL  369
SEQ ID NO:20  349 APKESNAIYSLRDPSEVMEFLTSLAEWKSSI---QAR  382
SEQ ID NO:22  327 IPKETDASYTLQDPTEVGQFLRHLVEWKRTSSQYHKL  363
SEQ ID NO:24  195 APKETEAFYSLRDPSEVMEFLNSLVRWKK-----HSL  226
SEQ ID NO:37  354 VPKDSNAFYSLRDPSEVMEFLKSLVTWKRSM---G--  385
SEQ ID NO:38  340 VPKDTNASYSLQDPSQVNKFLERLVEWKRKTVGEE--  374
                361                                   397
```

FIG. 1C

PLANT GENES ENCODING TREHALOSE METABOLISM ENZYMES

This application is a continuation-in-part of U.S. application Ser. No. 09/538,365, filed Mar. 29, 2000, now abandoned, which claims the benefit of U.S. Provisional Application No. 60/127,187, filed Mar. 31, 1999, now abandoned, each of which is herein incorporated by reference in its entirety.

FIELD OF THE INVENTION

This invention is in the field of plant molecular biology. More specifically, this invention pertains to nucleic acid fragments encoding trehalose metabolism enzymes in plants and seeds.

BACKGROUND OF THE INVENTION

Plants encounter a variety of environmental stresses that effect plant water status. The availability of water for nutrient transport, cellular metabolism, evaporative cooling and other biological functions is often impaired by these environmental stresses. One mechanism that all organisms use to tolerate abiotic stress is the accumulation of solutes that do not interfere with normal biochemical reactions. Three of the most effective compatible solutes, as shown by in vitro enzyme stabilization studies are ectoine, hydroxyectoine (unusual methylated cyclic amino acids) and trehalose (Lippert, K. et al. (1992) *Appl. Microbiol. Biotech.* 37:61–65). In fungi, bacteria and invertebrates trehalose plays a major role in desiccation tolerance and several genes have been identified in bacteria that encode enzymes required for trehalose biosynthesis (Bohnert, H. J. et al. (1995) *Plant Cell* 7:1099–1111). Two of the enzymes involved in trehalose biosynthesis are alpha, alpha-trehalose-phosphate synthase, and trehalose-6-phosphate phosphatase. Trehalose is metabolized by the enzyme alpha, alpha-trehalase. Initially, plants were thought to lack the ability to synthesize trehalose and attempts have been made to engineer water-stress tolerance in plants via the expression of microbial genes for trehalose synthesis. However, it has been demonstrated that *Arabidopsis thaliana* possesses a gene for trehalose-6-phosphate synthase, TPS1 (Blazquez et al. (1998) *Plant J* 13:685–689) and at least two genes, AtTPPA and AtTPPB, for trehalose-6-phosphate phosphatase (Vogel, G. et al. (1998) *Plant J* 13(5):673–683). Thus there is a great deal of interest in identifying genes that encode proteins that may be involved in trehalose synthesis in plants. These genes may be used to engineer trehalose synthesis in plants in an effort to produce plants with increased water stress tolerance. Accordingly, the availability of nucleic acid sequences encoding all or a portion of a trehalose-6-phosphate phosphatase, alpha, alpha-trehalase and alpha, alpha-trehalose-phosphate synthase would facilitate studies to better understand or engineer trehalose synthesis in plants and provide genetic tools to produce plants having increased water stress tolerance.

SUMMARY OF THE INVENTION

The present invention concerns isolated polynucleotides comprising (a) a first nucleotide sequence encoding a first polypeptide having alpha, alpha-trehalase activity, wherein the amino acid sequence of the first polypeptide and the amino acid sequence of SEQ ID NOs:2 or 4 have at least 80% sequence identity, (b) a second nucleotide sequence encoding a second polypeptide having alpha, alpha-trehalose-phosphate synthase activity, wherein the amino acid sequence of the second polypeptide and the amino acid sequence of SEQ ID NOs:6, 8, 10, 12 or 14 have at least 80% sequence identity, or (c) a third nucleotide sequence encoding a third polypeptide having trehalose-6-phosphate phosphatase activity, wherein the amino acid sequence of the third polypeptide and the amino acid sequence of SEQ ID NOs:16, 18, 20, 22, or 24 have at least 80% sequence identity. It is preferred that the identity be at least 85%, it is preferable if the identity is at least 90%, it is more preferred that the identity be at least 95%. The present invention also relates to isolated polynucleotides comprising the complement of the nucleotide sequence. More specifically, the present invention concerns isolated polynucleotides encoding the polypeptide sequence of SEQ ID NOs:2, 4, 6, 8, 10, 12, 14, 16, 18, 20, 22, or 24 or nucleotide sequences comprising the nucleotide sequence of SEQ ID NO:1, 3, 5, 7, 9, 11, 13, 15, 17, 19, 21 or 23.

In a first embodiment, the present invention includes an isolated polynucleotide comprising: (a) a first nucleotide sequence encoding a first polypeptide having alpha, alpha-trehalase activity, wherein the first polypeptide has an amino acid sequence of at least 80%, 85%, 90%, or 95% sequence identity, based on the Clustal V method of alignment, when compared to one of SEQ ID NO:2, or 4, (b) a second nucleotide sequence encoding a second polypeptide having alpha, alpha-trehalose-phosphate synthase activity, wherein the second polypeptide has an amino acid sequence of at least 80%, 85%, 90%, or 95% sequence identity, based on the Clustal V method of alignment, when compared to one of SEQ ID NO:6, 8, 10, 12 or 14, (c) a third nucleotide sequence encoding a third polypeptide having trehalose-6-phosphate phosphatase activity, wherein the third polypeptide has an amino acid sequence of at least 80%, 85%, 90%, or 95% sequence identity, based on the Clustal V method of alignment, when compared to one of SEQ ID NO:16, 18, 20, 22, or 24, or (d) a complement of the nucleotide sequence of (a), (b) or (c), wherein the complement and the nucleotide sequence consist of the same number of nucleotides and are 100% complementary. The first polypeptide preferably comprises the amino acid sequence of SEQ ID NOs:2 or 4, the second polypeptide preferably comprises the amino acid sequence of SEQ ID NOs:6, 8, 10, 12 or 14, and the third polypeptide preferably comprises the amino acid sequence of SEQ ID NOs:16, 18, 20, 22 or 24. The first nucleotide sequence preferably comprises the nucleotide sequence of SEQ ID NOs:1 or 3, the second nucleotide sequence preferably comprises the nucleotide sequence of SEQ ID NOs:5, 7, 9, 11 or 13, and the third nucleotide sequence preferably comprises the nucleotide sequence of SEQ ID NOs:15, 17, 19, 21 or 23.

In a second embodiment, the present invention concerns a recombinant DNA construct comprising any of the isolated polynucleotides of the present invention operably linked to at least one regulatory sequence, and a cell, a plant, and a seed comprising the recombinant DNA construct.

In a third embodiment, the present invention includes a vector comprising any of the isolated polynucleotides of the present invention.

In a fourth embodiment, the present invention concerns a method for transforming a cell comprising transforming a cell with any of the isolated polynucleotides of the present invention. The cell transformed by this method is also included. Advantageously, the cell is eukaryotic, e.g., a yeast or plant cell, or prokaryotic, e.g., a bacterium.

In a fifth embodiment, the present invention includes a method for producing a transgenic plant comprising transforming a plant cell with any of the isolated polynucleotides of the present invention and regenerating a plant from the transformed plant cell. The invention is also directed to the transgenic plant produced by this method, and seed obtained from this transgenic plant.

In a sixth embodiment, the present invention concerns (a) an isolated first polypeptide having alpha, alpha-trehalase activity, wherein the first polypeptide has an amino acid sequence of at least 80%, 85%, 90%, or 95% identity, based on the Clustal V method of alignment, when compared to one of SEQ ID NOs:2 or 4, (b) an isolated second polypeptide having alpha, alpha-trehalose-phosphate synthase activity, wherein the second polypeptide has an amino acid sequence of at least 80%, 85%, 90%, or 95% identity, based on the Clustal V method of alignment, when compared to one of SEQ ID NOs:6, 8, 10, 12 or 14, or (c) an isolated third polypeptide having trehalose-6-phosphate phosphatase activity, wherein the third polypeptide has an amino acid sequence of at least 80%, 85%, 90%, or 95% identity, based on the Clustal V method of alignment, when compared to one of SEQ ID NOs:16, 18, 20, 22 or 14. The first polypeptide preferably comprises one of SEQ ID NOs:2 or 4, the second polypeptide preferably comprises one of SEQ ID NOs:6, 8, 10, 12 or 14, and the third polypeptide preferably comprises one of SEQ ID NOs:16, 18, 20, 22 or 24.

In a seventh embodiment, the present invention includes to a method for isolating a polypeptide having alpha, alpha-trehalase, alpha, alpha-trehalose-phosphate synthase or trehalose-6-phosphate phosphatase activity comprising isolating the polypeptide from a cell or culture medium of the cell, wherein the cell comprises a recombinant DNA construct comprising a polynucleotide of the invention operably linked to at least one regulatory sequence.

In an eighth embodiment, this invention concerns a method for selecting a transformed cell comprising: (a) transforming a host cell with the recombinant DNA construct or an expression cassette of the present invention; and (b) growing the transformed host cell, preferably a plant cell, under conditions that allow expression of the polynucleotide encoding alpha, alpha-trehalase, alpha, alpha-trehalose-phosphate synthase or trehalose-6-phosphate phosphatase in an amount sufficient to complement a null mutant in order to provide a positive selection means.

In a ninth embodiment, this invention concerns a method of altering the level of expression of a alpha, alpha-trehalase, alpha, alpha-trehalose-phosphate synthase or trehalose-6-phosphate phosphatase protein in a host cell comprising: (a) transforming a host cell with a recombinant DNA construct of the present invention; and (b) growing the transformed host cell under conditions that are suitable for expression of the recombinant DNA construct wherein expression of the recombinant DNA construct results in production of altered levels of the alpha, alpha-trehalase, alpha, alpha-trehalose-phosphate synthase or trehalose-6-phosphate phosphatase protein in the transformed host cell.

A further embodiment of the instant invention is a method for evaluating at least one compound for its ability to inhibit the activity of an alpha, alpha-trehalase, alpha, alpha-trehalose-phosphate synthase or trehalose-6-phosphate phosphatase, the method comprising the steps of: (a) introducing into a host cell a recombinant DNA construct comprising a nucleic acid fragment encoding an alpha, alpha-trehalase, alpha, alpha-trehalose-phosphate synthase or trehalose-6-phosphate phosphatase polypeptide, operably linked to at least one regulatory sequence; (b) growing the host cell under conditions that are suitable for expression of the recombinant DNA construct wherein expression of the recombinant DNA construct results in production of an alpha, alpha-trehalase, alpha, alpha-trehalose-phosphate synthase or trehalose-6-phosphate phosphatase polypeptide in the host cell; (c) optionally purifying the alpha, alpha-trehalase, alpha, alpha-trehalose-phosphate synthase or trehalose-6-phosphate phosphatase polypeptide expressed by recombinant DNA construct in the host cell; (d) treating the alpha, alpha-trehalase, alpha, alpha-trehalose-phosphate synthase or trehalose-6-phosphate phosphatase polypeptide with a compound to be tested; (e) comparing the activity of the alpha, alpha-trehalase, alpha, alpha-trehalose-phosphate synthase or trehalose-6-phosphate phosphatase polypeptide that has been treated with a test compound to the activity of an untreated alpha, alpha-trehalase, alpha, alpha-trehalose-phosphate synthase or trehalose-6-phosphate phosphatase polypeptide, and (f) selecting compounds with potential for inhibitory activity.

BRIEF DESCRIPTION OF THE DRAWING AND SEQUENCE LISTINGS

The invention can be more fully understood from the following detailed description and the accompanying drawing and Sequence Listing which form a part of this application.

FIGS. 1A, 1B and 1C show a sequence alignment of the following: (1) the amino acid sequence of SEQ ID NO:16, the corn trehalose-6-phosphate phosphatase; (2) the amino acid sequence of SEQ ID NO:20, the soybean trehalose-6-phosphate phosphatase; (3) the amino acid sequence of SEQ ID NO:22, a second soybean trehalose-6-phosphate phosphatase; (4) the amino acid sequence of SEQ ID NO:24, a carboxy-terminal portion of the wheat trehalose-6-phosphate phosphatase; (5) the amino acid sequence of an *Arabidopsis thaliana* trehalose-6-phosphate phosphatase, AtTPPA, of Vogel et al. (NCBI GI No. 2944178; SEQ ID NO:37); and (6) the amino acid sequence of a second *Arabidopsis thaliana* trehalose-6-phosphate phosphatase, AtTPPB, of Vogel et al. (NCBI GI No. 2944180; SEQ ID NO:38). A consensus sequence of 397 amino acids was generated and is numbered below these six sequences. The amino acid positions for each sequence is given to the left of each row, and to the right of the final row. An asterisk above an amino acid residue indicates that the position is totally conserved among the given SEQ ID NOs, with respect to the *Arabidopsis thaliana* AtTPPA sequence. Below the sequences are shown two domains, A and B, that are conserved among trehalose-6-phosphate phosphatases, as described in Vogel et al. (1998) *Plant J* 13(5):673–683. The given sequence for each conserved domain is taken from the *Arabidopsis thaliana* AtTPPA amino acid sequence at these positions.

Table 1 lists the polypeptides that are described herein, the designation of the cDNA clones that comprise the nucleic acid fragments encoding polypeptides representing all or a substantial portion of these polypeptides, and the corresponding identifier (SEQ ID NO:) as used in the attached Sequence Listing. The sequence descriptions and Sequence Listing attached hereto comply with the rules governing nucleotide and/or amino acid sequence disclosures in patent applications as set forth in 37 C.F.R. §1.821–1.825.

TABLE 1

Trehalose Metabolism Enzymes

| Protein | Clone Designation | SEQ ID NO: (Nucleotide) | (Amino Acid) |
|---|---|---|---|
| Alpha, Alpha-Trehalase | cs1.pk0105.a2 | 1 | 2 |
| Alpha, Alpha-Trehalase | sdp2c.pk008.n16 (FIS) | 3 | 4 |
| Alpha, Alpha-Trehalose-Phosphate Synthase | p0102.ceraq93r | 5 | 6 |
| Alpha, Alpha-Trehalose-Phosphate Synthase | rls2.pk0002.f4 | 7 | 8 |
| Alpha, Alpha-Trehalose-Phosphate Synthase | rls2.pk0004.b4 | 9 | 10 |
| Alpha, Alpha-Trehalose-Phosphate Synthase | ssm.pk0021.f9 | 11 | 12 |
| Alpha, Alpha-Trehalose-Phosphate Synthase | wlk1.pk0017.e10 (FIS) | 13 | 14 |
| Trehalose-6-Phosphate Phosphatase | p0006.cbyvv20r (FIS) | 15 | 16 |
| Trehalose-6-Phosphate Phosphatase | rls72.pk0035.d8 (FIS) | 17 | 18 |
| Trehalose-6-Phosphate Phosphatase | sls2c.pk002.e16 (FIS) | 19 | 20 |
| Trehalose-6-Phosphate Phosphatase | srn1c.pk002.g19 (FIS) | 21 | 22 |
| Trehalose-6-Phosphate Phosphatase | wre1n.pk187.h5 (FIS) | 23 | 24 |
| Alpha, Alpha-Trehalase | sdp2c.pk008.n16 (EST) | 25 | 26 |
| Alpha, Alpha-Trehalose-Phosphate Synthase | wlk1.pk0017.e10 (EST) | 27 | 28 |
| Trehalose-6-Phosphate Phosphatase | rls72.pk0035.d8 (EST) | 29 | 30 |
| Trehalose-6-Phosphate Phosphatase | sls2c.pk002.e16 (EST) | 31 | 32 |
| Trehalose-6-Phosphate Phosphatase | srn1c.pk002.g19 (EST) | 33 | 34 |
| Trehalose-6-Phosphate Phosphatase | wre1n.pk187.h5 (EST) | 35 | 36 |

SEQ ID NO:37 corresponds to the amino acid sequence of the *Arabidopsis thaliana* trehalose-6-phosphate phosphatase, AtTPPA (NCBI GI No. 2944178).

SEQ ID NO:38 corresponds to the amino acid sequence of the *Arabidopsis thaliana* trehalose-6-phosphate phosphatase, AtTPPB (NCBI GI No. 2944180).

The Sequence Listing contains the one letter code for nucleotide sequence characters and the three letter codes for amino acids as defined in conformity with the IUPAC-IUBMB standards described in *Nucleic Acids Res.* 13:3021–3030 (1985) and in the *Biochemical J.* 219 (No. 2):345–373 (1984) which are herein incorporated by reference. The symbols and format used for nucleotide and amino acid sequence data comply with the rules set forth in 37 C.F.R. §1.822.

DETAILED DESCRIPTION OF THE INVENTION

In the context of this disclosure, a number of terms shall be utilized. The terms "polynucleotide", "polynucleotide sequence", "nucleic acid sequence", and "nucleic acid fragment"/"isolated nucleic acid fragment" are used interchangeably herein. These terms encompass nucleotide sequences and the like. A polynucleotide may be a polymer of RNA or DNA that is single- or double-stranded, that optionally contains synthetic, non-natural or altered nucleotide bases. A polynucleotide in the form of a polymer of DNA may be comprised of one or more segments of cDNA, genomic DNA, synthetic DNA, or mixtures thereof. An isolated polynucleotide of the present invention may include at least 30 contiguous nucleotides, preferably at least 40 contiguous nucleotides, most preferably at least 60 contiguous nucleotides derived from SEQ ID NO:1, 3, 5, 7, 9, 11, 13, 15, 17, 19, 21 or 23, or the complement of such sequences.

The term "isolated" refers to materials, such as nucleic acid molecules and/or proteins, which are substantially free or otherwise removed from components that normally accompany or interact with the materials in a naturally occurring environment. Isolated polynucleotides may be purified from a host cell in which they naturally occur. Conventional nucleic acid purification methods known to skilled artisans may be used to obtain isolated polynucleotides. The term also embraces recombinant polynucleotides and chemically synthesized polynucleotides.

The term "recombinant" means, for example, that a nucleic acid sequence is made by an artificial combination of two otherwise separated segments of sequence, e.g., by chemical synthesis or by the manipulation of isolated nucleic acids by genetic engineering techniques. A "recombinant DNA construct" comprises any of the isolated polynucleotides of the present invention operably linked to at least one regulatory sequence.

As used herein, "contig" refers to a nucleotide sequence that is assembled from two or more constituent nucleotide sequences that share common or overlapping regions of sequence homology. For example, the nucleotide sequences of two or more nucleic acid fragments can be compared and aligned in order to identify common or overlapping sequences. Where common or overlapping sequences exist between two or more nucleic acid fragments, the sequences (and thus their corresponding nucleic acid fragments) can be assembled into a single contiguous nucleotide sequence.

As used herein, "substantially similar" refers to nucleic acid fragments wherein changes in one or more nucleotide bases results in substitution of one or more amino acids, but do not affect the functional properties of the polypeptide encoded by the nucleotide sequence. "Substantially similar" also refers to nucleic acid fragments wherein changes in one or more nucleotide bases does not affect the ability of the nucleic acid fragment to mediate alteration of gene expression by gene silencing through for example antisense or co-suppression technology. "Substantially similar" also refers to modifications of the nucleic acid fragments of the instant invention such as deletion or insertion of one or more nucleotides that do not substantially affect the functional properties of the resulting transcript vis-a-vis the ability to mediate gene silencing or alteration of the functional properties of the resulting protein molecule. It is therefore understood that the invention encompasses more than the specific exemplary nucleotide or amino acid sequences and includes functional equivalents thereof. The terms "substantially similar" and "corresponding substantially" are used interchangeably herein.

The "Clustal V method of alignment" corresponds to the alignment method labeled Clustal V (described by Higgins and Sharp (1989) CABIOS. 5:151–153) and found in the Megalign program of the LASERGENE bioinformatics computing suite (DNASTAR Inc., Madison, Wis.). The "default parameters" are the parameters pre-set by the manufacturer of the program and for multiple alignments they correspond to GAP PENALTY=10 and GAP LENGTH PENALTY=10, while for pairwise alignments they are KTUPLE=1, GAP PENALTY=3, WINDOW=5 and DIAGONALS SAVED=5. After alignment of the sequences, using the Clustal V program, it is possible to obtain a "percent identity" by viewing the "sequence distances" table on the same program.

Substantially similar nucleic acid fragments may be selected by screening nucleic acid fragments representing subfragments or modifications of the nucleic acid fragments of the instant invention, wherein one or more nucleotides are substituted, deleted and/or inserted, for their ability to affect the level of the polypeptide encoded by the unmodified nucleic acid fragment in a plant or plant cell. For example, a substantially similar nucleic acid fragment representing at least 30 contiguous nucleotides, preferably at least 40 contiguous nucleotides, most preferably at least 60 contiguous nucleotides derived from the instant nucleic acid fragment can be constructed and introduced into a plant or plant cell. The level of the polypeptide encoded by the unmodified nucleic acid fragment present in a plant or plant cell exposed to the substantially similar nucleic fragment can then be compared to the level of the polypeptide in a plant or plant cell that is not exposed to the substantially similar nucleic acid fragment.

For example, it is well known in the art that antisense suppression and co-suppression of gene expression may be accomplished using nucleic acid fragments representing less than the entire coding region of a gene, and by using nucleic acid fragments that do not share 100% sequence identity with the gene to be suppressed. Moreover, alterations in a nucleic acid fragment which result in the production of a chemically equivalent amino acid at a given site, but do not effect the functional properties of the encoded polypeptide, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products. Consequently, an isolated polynucleotide comprising a nucleotide sequence of at least 30 (preferably at least 40, most preferably at least 60) contiguous nucleotides derived from a nucleotide sequence of SEQ ID NOs: 1, 3, 5, 7, 9, 11, 13, 15, 17, 19, 21 or 23, and the complement of such nucleotide sequences may be used to affect the expression and/or function of an alpha, alpha-trehalase, alpha, alpha-trehalose-phosphate synthase or trehalose-6-phosphate phosphatase in a host cell. A method of using an isolated polynucleotide to affect the level of expression of a polypeptide in a host cell (eukaryotic, such as plant or yeast, prokaryotic such as bacterial) may comprise the steps of: constructing an isolated polynucleotide of the present invention or an isolated recombinant DNA construct of the present invention; introducing the isolated polynucleotide or the isolated recombinant DNA construct into a host cell; measuring the level of a polypeptide or enzyme activity in the host cell containing the isolated polynucleotide; and comparing the level of a polypeptide or enzyme activity in the host cell containing the isolated polynucleotide with the level of a polypeptide or enzyme activity in a host cell that does not contain the isolated polynucleotide.

Moreover, substantially similar nucleic acid fragments may also be characterized by their ability to hybridize. Estimates of such homology are provided by either DNA-DNA or DNA-RNA hybridization under conditions of stringency as is well understood by those skilled in the art (Hames and Higgins, Eds. (1985) Nucleic Acid Hybridisation, IRL Press, Oxford, U.K.). Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions. One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions uses higher temperatures in which the washes are identical to those above except for the temperature of the final two 30 min washes in 0.2×SSC, 0.5% SDS was increased to 60° C. Another preferred set of highly stringent conditions uses two final washes in 0.1×SSC, 0.1% SDS at 65° C.

Substantially similar nucleic acid fragments of the instant invention may also be characterized by the percent identity of the amino acid sequences that they encode to the amino acid sequences disclosed herein, as determined by algorithms commonly employed by those skilled in this art. Suitable nucleic acid fragments (isolated polynucleotides of the present invention) encode polypeptides that are at least 70% identical, preferably at least 80% identical to the amino acid sequences reported herein. Preferred nucleic acid fragments encode amino acid sequences that are at least 85% identical to the amino acid sequences reported herein. More preferred nucleic acid fragments encode amino acid sequences that are at least 90% identical to the amino acid sequences reported herein. Most preferred are nucleic acid fragments that encode amino acid sequences that are at least 95% identical to the amino acid sequences reported herein. Suitable nucleic acid fragments not only have the above identities but typically encode a polypeptide having at least 50 amino acids, preferably at least 100 amino acids, more preferably at least 150 amino acids, still more preferably at least 200 amino acids, and most preferably at least 250 amino acids.

It is well understood by one skilled in the art that many levels of sequence identity are useful in identifying related polypeptide sequences. Useful examples of percent identities are 50%, 55%, 60%, 65%, 70%, 75%, 80%, 85%, 90%, or 95%, or any integer percentage from 55% to 100%. Sequence alignments and percent identity calculations were performed using the Megalign program of the LASERGENE bioinformatics computing suite (DNASTAR Inc., Madison, Wis.). Multiple alignment of the sequences was performed using the Clustal method of alignment (Higgins and Sharp (1989) *CABIOS.* 5:151–153) with the default parameters (GAP PENALTY=10, GAP LENGTH PENALTY=10). Default parameters for pairwise alignments using the Clustal method were KTUPLE=1, GAP PENALTY=3, WINDOW=5 and DIAGONALS SAVED=5.

A "substantial portion" of an amino acid or nucleotide sequence comprises an amino acid or a nucleotide sequence that is sufficient to afford putative identification of the protein or gene that the amino acid or nucleotide sequence comprises. Amino acid and nucleotide sequences can be evaluated either manually by one skilled in the art, or by using computer-based sequence comparison and identification tools that employ algorithms such as BLAST (Basic Local Alignment Search Tool; Altschul et al. (1993) *J. Mol. Biol.* 215:403–410; see also the explanation of the BLAST alogarithm on the world wide web site for the National Center for Biotechnology Information at the National Library of Medicine of the National Institutes of Health). In general, a sequence of ten or more contiguous amino acids or thirty or more contiguous nucleotides is necessary in order to putatively identify a polypeptide or nucleic acid sequence as homologous to a known protein or gene. Moreover, with respect to nucleotide sequences, gene-specific oligonucleotide probes comprising 30 or more contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12 or more nucleotides may be used as amplification primers in PCR in order to obtain a particular nucleic acid fragment comprising the primers. Accordingly, a "substantial portion" of a nucleotide sequence comprises a nucleotide sequence that will afford specific identification and/or isolation of a nucleic acid fragment comprising the sequence. The instant specification teaches amino acid and nucleotide sequences encoding polypeptides that comprise one or more particular plant proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

"Codon degeneracy" refers to divergence in the genetic code permitting variation of the nucleotide sequence without effecting the amino acid sequence of an encoded polypeptide. Accordingly, the instant invention relates to any nucleic acid fragment comprising a nucleotide sequence that encodes all or a substantial portion of the amino acid sequences set forth herein. The skilled artisan is well aware of the "codon-bias" exhibited by a specific host cell in usage of nucleotide codons to specify a given amino acid. Therefore, when synthesizing a nucleic acid fragment for improved expression in a host cell, it is desirable to design the nucleic acid fragment such that its frequency of codon usage approaches the frequency of preferred codon usage of the host cell.

"Synthetic nucleic acid fragments" can be assembled from oligonucleotide building blocks that are chemically synthesized using procedures known to those skilled in the art. These building blocks are ligated and annealed to form larger nucleic acid fragments which may then be enzymatically assembled to construct the entire desired nucleic acid fragment. "Chemically synthesized", as related to a nucleic acid fragment, means that the component nucleotides were assembled in vitro. Manual chemical synthesis of nucleic acid fragments may be accomplished using well established procedures, or automated chemical synthesis can be performed using one of a number of commercially available machines. Accordingly, the nucleic acid fragments can be tailored for optimal gene expression based on optimization of the nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign-gene" refers to a gene not normally found in the host organism, but that is introduced into the host organism by gene transfer. Foreign genes can comprise native genes inserted into a non-native organism, recombinant DNA constructs, or chimeric genes. A "transgene" is an isolated nucleic acid fragment or recombinant DNA construct that has been introduced into the genome by a transformation procedure.

"Coding sequence" refers to a nucleotide sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a nucleotide sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a nucleotide sequence which can stimulate promoter activity and may be an innate element of the promoter or a heterologous element inserted to enhance the level or tissue-specificity of a promoter. Promoters may be derived in their entirety from a native gene, or may be composed of different elements derived from different promoters found in nature, or may even comprise synthetic nucleotide segments. It is understood by those skilled in the art that different promoters may direct the expression of a gene in different tissues or cell types, or at different stages of development, or in response to different environmental conditions. Promoters which cause a nucleic acid fragment to be expressed in most cell types at most times are commonly referred to as "constitutive promoters". New promoters of various types useful in plant cells are constantly being discovered; numerous examples may be found in the compilation by Okamuro and Goldberg (1989) *Biochemistry of Plants* 15:1–82. It is further recognized that since in most cases the exact boundaries of regulatory sequences have not been completely defined, nucleic acid fragments of different lengths may have identical promoter activity.

"Translation leader sequence" refers to a nucleotide sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner and Foster (1995) *Mol. Biotechnol.* 3:225–236).

"3' non-coding sequences" refer to nucleotide sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al. (1989) *Plant Cell* 1:671–680.

"RNA transcript" refers to the product resulting from RNA polymerase catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA (mRNA)" refers to the RNA that is without introns and that can be translated into polypeptides by the cell. "cDNA" refers to DNA that is complementary to and derived from an mRNA template. The cDNA can be single-stranded or converted to double stranded form using, for example, the Klenow fragment of DNA polymerase I. "Sense-RNA" refers to an RNA transcript that includes the mRNA and so can be translated into a polypeptide by the cell. "Antisense RNA" refers to an RNA transcript that is complementary to all or part of a target primary transcript or mRNA and that blocks the expression of a target gene (see U.S. Pat. No. 5,107,065, incorporated herein by reference). The complementarity of an antisense RNA may be with any part of the specific nucleotide sequence, i.e., at the 5' non-coding sequence, 3' non-coding sequence, introns, or the coding sequence. "Functional RNA" refers to sense RNA, antisense RNA, ribozyme RNA, or other RNA that may not be translated but yet has an effect on cellular processes.

The term "operably linked" refers to the association of two or more nucleic acid fragments on a single polynucleotide so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts capable of suppressing the expression of identical or substantially similar foreign or endogenous genes (U.S. Pat. No. 5,231,020, incorporated herein by reference).

A "protein" or "polypeptide" is a chain of amino acids arranged in a specific order determined by the coding sequence in a polynucleotide encoding the polypeptide. Each protein or polypeptide has a unique function.

"Altered levels" or "altered expression" refers to the production of gene product(s) in transgenic organisms in amounts or proportions that differ from that of normal or non-transformed organisms.

"Mature protein" or the term "mature" when used in describing a protein refers to a post-translationally processed polypeptide; i.e., one from which any pre- or propeptides present in the primary translation product have been removed. "Precursor protein" or the term "precursor" when used in describing a protein refers to the primary product of translation of mRNA; i.e., with pre- and propeptides still present. Pre- and propeptides may be but are not limited to intracellular localization signals.

A "chloroplast transit peptide" is an amino acid sequence which is translated in conjunction with a protein and directs the protein to the chloroplast or other plastid types present in the cell in which the protein is made. "Chloroplast transit sequence" refers to a nucleotide sequence that encodes a chloroplast transit peptide. A "signal peptide" is an amino acid sequence which is translated in conjunction with a protein and directs the protein to the secretory system (Chrispeels (1991) *Ann. Rev. Plant Phys. Plant Mol. Biol.* 42:21–53). If the protein is to be directed to a vacuole, a vacuolar targeting signal (supra) can further be added, or if to the endoplasmic reticulum, an endoplasmic reticulum retention signal (supra) may be added. If the protein is to be directed to the nucleus, any signal peptide present should be removed and instead a nuclear localization signal included (Raikhel (1992) *Plant Phys.* 100:1627–1632).

"Transformation" refers to the transfer of a nucleic acid fragment into the genome of a host organism. Host organisms containing the transferred nucleic acid fragments are referred to as "transgenic" or "transformed" organisms. Examples of methods of plant transformation include Agrobacterium-mediated transformation (De Blaere et al. (1987) *Meth. Enzymol.* 143:277; Ishida Y. et al. (1996) *Nature Biotech.* 14:745–750) and particle-accelerated or "gene gun" transformation technology (Klein et al. (1987) *Nature* (London) 327:70–73; U.S. Pat. No. 4,945,050, incorporated herein by reference). Thus, isolated polynucleotides of the present invention can be incorporated into recombinant constructs, typically DNA constructs, capable of introduction into and replication in a host cell. Such a construct can be a vector that includes a replication system and sequences that are capable of transcription and translation of a polypeptide-encoding sequence in a given host cell. A number of vectors suitable for stable transfection of plant cells or for the establishment of transgenic plants have been described in, e.g., Pouwels et al., Cloning Vectors: A Laboratory Manual, 1985, supp. 1987; Weissbach and Weissbach, Methods for Plant Molecular Biology, Academic Press, 1989; and Flevin et al., Plant Molecular Biology Manual, Kluwer Academic Publishers, 1990. Typically, plant expression vectors include, for example, one or more cloned plant genes under the transcriptional control of 5' and 3' regulatory sequences and a dominant selectable marker. Such plant expression vectors also can contain a promoter regulatory region (e.g., a regulatory region controlling inducible or constitutive, environmentally- or developmentally-regulated, or cell- or tissue-specific expression), a transcription initiation start site, a ribosome binding site, an RNA processing signal, a transcription termination site, and/or a polyadenylation signal.

"Stable transformation" refers to the transfer of a nucleic acid fragment into a genome of a host organism, including both nuclear and organellar genomes, resulting in genetically stable inheritance. In contrast, "transient transformation" refers to the transfer of a nucleic acid fragment into the nucleus, or DNA-containing organelle, of a host organism resulting in gene expression without integration or stable inheritance. The term "transformation" as used herein refers to both stable transformation and transient transformation.

The terms "recombinant construct", "expression construct" and "recombinant expression construct" are used interchangeably herein. These terms refer to a functional unit of genetic material that can be inserted into the genome of a cell using standard methodology well known to one skilled in the art. Such construct may be used by itself or may be used in conjunction with a vector. If a vector is used, the choice of vector is dependent upon the method that will be used to transform host plants as is well known to those skilled in the art.

Standard recombinant DNA and molecular cloning techniques used herein are well known in the art and are described more fully in Sambrook et al. *Molecular Cloning: A Laboratory Manual*; Cold Spring Harbor Laboratory Press: Cold Spring Harbor, 1989 (hereinafter "Maniatis").

"Motifs" or "subsequences" refer to short regions of conserved sequences of nucleic acids or amino acids that comprise part of a longer sequence. For example, it is expected that such conserved subsequences would be important for function, and could be used to identify new homologues in plants. It is expected that some or all of the elements may be found in a homologue. Also, it is expected that one or two of the conserved amino acids in any given motif may differ in a true homologue.

"PCR" or "polymerase chain reaction" is well known by those skilled in the art as a technique used for the amplification of specific DNA segments (U.S. Pat. Nos. 4,683,195 and 4,800,159).

The present invention concerns isolated polynucleotides comprising (a) a first nucleotide sequence encoding a first polypeptide having alpha, alpha-trehalase activity, wherein the amino acid sequence of the first polypeptide and the amino acid sequence of SEQ ID NOs:2 or 4 have at least 80% sequence identity, (b) a second nucleotide sequence encoding a second polypeptide having alpha, alpha-trehalose-phosphate synthase activity, wherein the amino acid sequence of the second polypeptide and the amino acid sequence of SEQ ID NOs:6, 8, 10, 12 or 14 have at least 80% sequence identity, or (c) a third nucleotide sequence encoding a third polypeptide having trehalose-6-phosphate phosphatase activity, wherein the amino acid sequence of the third polypeptide and the amino acid sequence of SEQ ID NOs:16, 18, 20, 22, or 24 have at least 80% sequence identity. It is preferred that the identity be at least 85%, it is preferable if the identity is at least 90%, it is more preferred that the identity be at least 95%.

This invention also includes to the isolated complement of such polynucleotides, wherein the complement and the polynucleotide consist of the same number of nucleotides, and the nucleotide sequences of the complement and the polynucleotide have 100% complementarity.

Nucleic acid fragments encoding at least a portion of several alpha, alpha-trehalase, alpha, alpha-trehalose-phosphate synthase or trehalose-6-phosphate phosphatase have been isolated and identified by comparison of random plant cDNA sequences to public databases containing nucleotide and protein sequences using the BLAST algorithms well known to those skilled in the art. The nucleic acid fragments of the instant invention may be used to isolate cDNAs and genes encoding homologous proteins from the same or other plant species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction, ligase chain reaction).

For example, genes encoding other alpha, alpha-trehalase, alpha, alpha-trehalose-phosphate synthase or trehalose-6-phosphate phosphatase, either as cDNAs or genomic DNAs, could be isolated directly by using all or a portion of the instant nucleic acid fragments as DNA hybridization probes to screen libraries from any desired plant employing methodology well known to those skilled in the art. Specific oligonucleotide probes based upon the instant nucleic acid sequences can be designed and synthesized by methods known in the art (Maniatis). Moreover, an entire sequence can be used directly to synthesize DNA probes by methods known to the skilled artisan such as random primer DNA labeling, nick translation, end-labeling techniques, or RNA probes using available in vitro transcription systems. In addition, specific primers can be designed and used to amplify a part or all of the instant sequences. The resulting amplification products can be labeled directly during amplification reactions or labeled after amplification reactions, and used as probes to isolate full length cDNA or genomic fragments under conditions of appropriate stringency.

In addition, two short segments of the instant nucleic acid fragments may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding plant genes. Alternatively, the second primer sequence may be based upon sequences derived from the cloning vector. For example, the skilled artisan can follow the RACE protocol (Frohman et al. (1988) *Proc. Natl. Acad. Sci. USA* 85:8998–9002) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara et al. (1989) *Proc. Natl. Acad. Sci. USA* 86:5673–5677; Loh et al. (1989) *Science* 243:217–220). Products generated by the 3' and 5' RACE procedures can be combined to generate full-length cDNAs (Frohman and Martin (1989) *Techniques* 1:165). Consequently, a polynucleotide comprising a nucleotide sequence of at least 30 (preferably at least 40, most preferably at least 60) contiguous nucleotides derived from a nucleotide sequence of SEQ ID NOs: 1, 3, 5, 7, 9, 11, 13, 15, 17, 19, 21 or 23, and the complement of such nucleotide sequences may be used in such methods to obtain a nucleic acid fragment encoding a substantial portion of an amino acid sequence of a polypeptide.

Availability of the instant nucleotide and deduced amino acid sequences facilitates immunological screening of cDNA expression libraries. Synthetic peptides representing portions of the instant amino acid sequences may be synthesized. These peptides can be used to immunize animals to produce polyclonal or monoclonal antibodies with specificity for peptides or proteins comprising the amino acid sequences. These antibodies can be then be used to screen cDNA expression libraries to isolate full-length cDNA clones of interest (Lerner (1984) *Adv. Immunol.* 36:1–34; Maniatis).

In another embodiment, this invention concerns viruses and host cells comprising either the recombinant DNA constructs of the invention as described herein or isolated polynucleotides of the invention as described herein. Examples of host cells which can be used to practice the invention include, but are not limited to, yeast, bacteria, and plants.

As was noted above, the nucleic acid fragments of the instant invention may be used to create transgenic plants in which the disclosed polypeptides are present at higher or lower levels than normal or in cell types or developmental stages in which they are not normally found. This would have the effect of altering the level of trehalose in those cells.

Overexpression of the polypeptides of the instant invention may be accomplished by first constructing a recombinant DNA construct in which the coding region is operably linked to a promoter capable of directing expression of a polypeptide in the desired tissues at the desired stage of development. The recombinant DNA construct may comprise promoter sequences and translation leader sequences derived from the same genes. 3' Non-coding sequences corresponding to transcription termination signals may also be provided. The instant recombinant DNA construct may also comprise one or more introns in order to facilitate expression of the recombinant DNA construct.

Plasmid vectors comprising the instant isolated polynucleotide(s) (or recombinant DNA construct(s)) may be constructed. The choice of plasmid vector is dependent upon the method that will be used to transform host plants. The skilled artisan is well aware of the genetic elements that must be present on the plasmid vector in order to successfully transform, select and propagate host cells containing the recombinant DNA construct or chimeric gene. The skilled artisan will also recognize that different independent transformation events will result in different levels and patterns of expression (Jones et al. (1985) *EMBO J.* 4:2411–2418; De Almeida et al. (1989) *Mol. Gen. Genetics* 218:78–86), and thus that multiple events must be screened in order to obtain lines displaying the desired expression level and pattern. Such screening may be accomplished by Southern analysis of DNA, Northern analysis of mRNA expression, Western analysis of protein expression, or phenotypic analysis.

For some applications it may be useful to direct the instant polypeptides to different cellular compartments, or to facilitate its secretion from the cell. It is thus envisioned that the recombinant DNA construct(s) described above may be further supplemented by directing the coding sequence to encode the instant polypeptides with appropriate intracellular targeting sequences such as transit sequences (Keegstra (1989) *Cell* 56:247–253), signal sequences or sequences encoding endoplasmic reticulum localization (Chrispeels (1991) *Ann. Rev. Plant Phys. Plant Mol. Biol.* 42:21–53), or nuclear localization signals (Raikhel (1992) *Plant Phys.* 100: 1627–1632) with or without removing targeting sequences that are already present. While the references cited give examples of each of these, the list is not exhaustive and more targeting signals of use may be discovered in the future.

It may also be desirable to reduce or eliminate expression of genes encoding the instant polypeptides in plants for some applications. In order to accomplish this, a recombinant DNA construct designed for co-suppression of the instant polypeptide can be constructed by linking a gene or gene fragment encoding that polypeptide to plant promoter sequences. Alternatively, a recombinant DNA construct designed to express antisense RNA for all or part of the instant nucleic acid fragment can be constructed by linking the gene or gene fragment in reverse orientation to plant promoter sequences. Either the co-suppression or antisense recombinant DNA constructs could be introduced into plants via transformation wherein expression of the corresponding endogenous genes are reduced or eliminated.

Molecular genetic solutions to the generation of plants with altered gene expression have a decided advantage over more traditional plant breeding approaches. Changes in plant phenotypes can be produced by specifically inhibiting expression of one or more genes by antisense inhibition or cosuppression (U.S. Pat. Nos. 5,190,931, 5,107,065 and 5,283,323). An antisense or cosuppression construct would act as a dominant negative regulator of gene activity. While conventional mutations can yield negative regulation of gene activity these effects are most likely recessive. The dominant negative regulation available with a transgenic approach may be advantageous from a breeding perspective. In addition, the ability to restrict the expression of a specific phenotype to the reproductive tissues of the plant by the use of tissue specific promoters may confer agronomic advantages relative to conventional mutations which may have an effect in all tissues in which a mutant gene is ordinarily expressed.

The person skilled in the art will know that special considerations are associated with the use of antisense or cosuppression technologies in order to reduce expression of particular genes. For example, the proper level of expression of sense or antisense genes may require the use of different recombinant DNA constructs utilizing different regulatory elements known to the skilled artisan. Once transgenic plants are obtained by one of the methods described above, it will be necessary to screen individual transgenics for those that most effectively display the desired phenotype. Accordingly, the skilled artisan will develop methods for screening large numbers of transformants. The nature of these screens will generally be chosen on practical grounds. For example, one can screen by looking for changes in gene expression by using antibodies specific for the protein encoded by the gene being suppressed, or one could establish assays that specifically measure enzyme activity. A preferred method will be one which allows large numbers of samples to be processed rapidly, since it will be expected that a large number of transformants will be negative for the desired phenotype.

In another embodiment, the present invention concerns (a) an isolated first polypeptide having alpha, alpha-trehalase activity, wherein the first polypeptide has an amino acid sequence of at least 80%, 85%, 90%, or 95% identity, based on the Clustal V method of alignment, when compared to one of SEQ ID NOs:2 or 4, (b) an isolated second polypeptide having alpha, alpha-trehalose-phosphate synthase activity, wherein the second polypeptide has an amino acid sequence of at least 80%, 85%, 90%, or 95% identity, based on the Clustal V method of alignment, when compared to one of SEQ ID NOs:6, 8, 10, 12 or 14, or (c) an isolated third polypeptide having trehalose-6-phosphate phosphatase activity, wherein the third polypeptide has an amino acid sequence of at least 80%, 85%, 90%, or 95% identity, based on the Clustal V method of alignment, when compared to one of SEQ ID NOs:16, 18, 20, 22 or 14.

The instant polypeptides (or portions thereof) may be produced in heterologous host cells, particularly in the cells of microbial hosts, and can be used to prepare antibodies to these proteins by methods well known to those skilled in the art. The antibodies are useful for detecting the polypeptides of the instant invention in situ in cells or in vitro in cell extracts. Preferred heterologous host cells for production of the instant polypeptides are microbial hosts. Microbial expression systems and expression vectors containing regulatory sequences that direct high level expression of foreign proteins are well known to those skilled in the art. Any of these could be used to construct a recombinant DNA construct for production of the instant polypeptides. This recom binant DNA construct could then be introduced into appropriate microorganisms via transformation to provide high level expression of the encoded alpha, alpha-trehalase, alpha, alpha-trehalose-phosphate synthase or trehalose-6-phosphate phosphatase. An example of a vector for high level expression of the instant polypeptides in a bacterial host is provided (Example 8).

Additionally, the instant polypeptides can be used as a target to facilitate design and/or identification of inhibitors of those enzymes that may be useful as herbicides. This is desirable because the polypeptides described herein catalyze various steps in trehalose metabolism. Accordingly, inhibition of the activity of one or more of the enzymes described herein could lead to inhibition of plant growth. Thus, the instant polypeptides could be appropriate for new herbicide discovery and design.

All or a substantial portion of the polynucleotides of the instant invention may also be used as probes for genetically and physically mapping the genes that they are a part of, and used as markers for traits linked to those genes. Such information may be useful in plant breeding in order to develop lines with desired phenotypes. For example, the instant nucleic acid fragments may be used as restriction fragment length polymorphism (RFLP) markers. Southern blots (Maniatis) of restriction-digested plant genomic DNA may be probed with the nucleic acid fragments of the instant invention. The resulting banding patterns may then be subjected to genetic analyses using computer programs such as MapMaker (Lander et al. (1987) *Genomics* 1:174–181) in order to construct a genetic map. In addition, the nucleic acid fragments of the instant invention may be used to probe Southern blots containing restriction endonuclease-treated genomic DNAs of a set of individuals representing parent and progeny of a defined genetic cross. Segregation of the DNA polymorphisms is noted and used to calculate the position of the instant nucleic acid sequence in the genetic map previously obtained using this population (Botstein et al. (1980) *Am. J. Hum. Genet.* 32:314–331).

The production and use of plant gene-derived probes for use in genetic mapping is described in Bernatzky and Tanksley (1986) *Plant Mol. Biol. Reporter* 4:37–41. Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

Nucleic acid probes derived from the instant nucleic acid sequences may also be used for physical mapping (i.e., placement of sequences on physical maps; see Hoheisel et al. In: *Nonmammalian Genomic Analysis*: A Practical Guide, Academic press 1996, pp. 319–346, and references cited therein).

Nucleic acid probes derived from the instant nucleic acid sequences may be used in direct fluorescence in situ hybridization (FISH) mapping (Trask (1991) *Trends Genet.* 7:149–154). Although current methods of FISH mapping favor use of large clones (several kb to several hundred kb; see Laan et al. (1995) *Genome Res.* 5:13–20), improvements in sensitivity may allow performance of FISH mapping using shorter probes.

A variety of nucleic acid amplification-based methods of genetic and physical mapping may be carried out using the instant nucleic acid sequences. Examples include allele-specific amplification (Kazazian (1989) *J. Lab. Clin. Med.* 11:95–96), polymorphism of PCR-amplified fragments (CAPS; Sheffield et al. (1993) *Genomics* 16:325–332), allele-specific ligation (Landegren et al. (1988) *Science* 241:1077–1080), nucleotide extension reactions (Sokolov (1990) *Nucleic Acid Res.* 18:3671), Radiation Hybrid Mapping (Walter et al. (1997) *Nat. Genet.* 7:22–28) and Happy Mapping (Dear and Cook (1989) *Nucleic Acid Res.* 17:6795–6807). For these methods, the sequence of a nucleic acid fragment is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, is generally not necessary for mapping methods.

Loss of function mutant phenotypes may be identified for the instant cDNA clones either by targeted gene disruption protocols or by identifying specific mutants for these genes contained in a maize population carrying mutations in all possible genes (Ballinger and Benzer (1989) *Proc. Natl. Acad. Sci USA* 86:9402–9406; Koes et al. (1995) *Proc. Natl. Acad. Sci USA* 92:8149–8153; Bensen et al. (1995) *Plant Cell* 7:75–84). The latter approach may be accomplished in two ways. First, short segments of the instant nucleic acid fragments may be used in polymerase chain reaction protocols in conjunction with a mutation tag sequence primer on DNAs prepared from a population of plants in which Mutator transposons or some other mutation-causing DNA element has been introduced (see Bensen, supra). The amplification of a specific DNA fragment with these primers indicates the insertion of the mutation tag element in or near the plant gene encoding the instant polypeptide. Alternatively, the instant nucleic acid fragment may be used as a hybridization probe against PCR amplification products generated from the mutation population using the mutation tag sequence primer in conjunction with an arbitrary genomic site primer, such as that for a restriction enzyme site-anchored synthetic adaptor. With either method, a plant containing a mutation in the endogenous gene encoding the instant polypeptide can be identified and obtained. This mutant plant can then be used to determine or confirm the natural function of the instant polypeptide disclosed herein.

EXAMPLES

The present invention is further defined in the following Examples, in which parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

The disclosure of each reference set forth herein is incorporated herein by reference in its entirety.

Example 1

Composition of cDNA Libraries; Isolation and Sequencing of cDNA Clones cDNA libraries representing mRNAs from various corn, rice, soybean and wheat tissues were prepared. The characteristics of the libraries are described below.

TABLE 2 cDNA Libraries from Corn, Rice, Soybean and Wheat

| Library | Tissue | Clone |
|---|---|---|
| cs1 | Corn leaf, sheath 5 wk plant | cs1.pk0105.a2 |
| p0006 | Corn young shoot | p0006.cbyvv20r |
| p0102 | Corn early meiosis tassels, 16–18 cm long* | p0102.ceraq93r |
| rls2 | Rice leaf (15 days after gremination) 2 hrs after infection of *Magnaporta grisea* strain 4360-R-62 (AVR2-YAMO) | rls2.pk0002.f4 |
| | | rls2.pk0004.b4 |
| rls72 | Rice leaf (15 days after germination) 72 hours after infection of *Magnaporta grisea* strain 4360-R-67 (avr2-yamo) | rls72.pk0035.d8 |
| sdp2c | Soybean developing pods 6–7 mm | sdp2c.pk008.n16 |
| sls2c | Soybean infected with *Sclerotinia sclerotiorum* mycelium. | sls2c.pk002.e16 |
| srn1c | Soybean developing root nodules. | srn1c.pk002.g19 |
| ssm | Soybean shoot meristem | ssm.pk0021.f9 |
| wlk1 | Wheat seedlings 1 hr after treatment with herbicide** | wlk1.pk0017.e10 |
| wre1n | Wheat root; 7 day old etiolated seedling* | wre1n.pk187.h5 |

*These libraries were normalized essentially as described in U.S. Pat. No. 5,482,845, incorporated herein by reference.
**Application of 6-iodo-2-propoxy-3-propyl-4(3H)-quinazolinone; synthesis and methods of using this compound are described in USSN 08/545,827, incorporated herein by reference.

cDNA libraries may be prepared by any one of many methods available. For example, the cDNAs may be introduced into plasmid vectors by first preparing the cDNA libraries in Uni-ZAP™ XR vectors according to the manufacturer's protocol (Stratagene Cloning Systems, La Jolla, Calif.). The Uni-ZAP™ XR libraries are converted into plasmid libraries according to the protocol provided by Stratagene. Upon conversion, cDNA inserts will be contained in the plasmid vector pBluescript. In addition, the cDNAs may be introduced directly into precut Bluescript II SK(+) vectors (Stratagene) using T4 DNA ligase (New England Biolabs), followed by transfection into DH10B cells according to the manufacturer's protocol (GIBCO BRL Products). Once the cDNA inserts are in plasmid vectors, plasmid DNAs are prepared from randomly picked bacterial colonies containing recombinant pBluescript plasmids, or the insert cDNA sequences are amplified via polymerase chain reaction using primers specific for vector sequences flanking the inserted cDNA sequences. Amplified insert DNAs or plasmid DNAs are sequenced in dye-primer sequencing reactions to generate partial cDNA sequences (expressed sequence tags or "ESTs"; see Adams et al., (1991) *Science* 252:1651–1656). The resulting ESTs are analyzed using a Perkin Elmer Model 377 fluorescent sequencer.

Full-insert sequence (FIS) data is generated utilizing a modified transposition protocol. Clones identified for FIS are recovered from archived glycerol stocks as single colonies, and plasmid DNAs are isolated via alkaline lysis. Isolated DNA templates are reacted with vector primed M13 forward and reverse oligonucleotides in a PCR-based sequencing reaction and loaded onto automated sequencers. Confirmation of clone identification is performed by sequence alignment to the original EST sequence from which the FIS request is made.

Confirmed templates are transposed via the Primer Island transposition kit (PE Applied Biosystems, Foster City, Calif.) which is based upon the *Saccharomyces cerevisiae* Ty1 transposable element (Devine and Boeke (1994) *Nucleic Acids Res.* 22:3765–3772). The in vitro transposition system places unique binding sites randomly throughout a population of large DNA molecules. The transposed DNA is then used to transform DH10B electro-competent cells (Gibco BRL/Life Technologies, Rockville, Md.) via electroporation. The transposable element contains an additional selectable marker (named DHFR; Fling and Richards (1983) *Nucleic Acids Res.* 11:5147–5158), allowing for dual selection on agar plates of only those subclones containing the integrated transposon. Multiple subclones are randomly selected from each transposition reaction, plasmid DNAs are prepared via alkaline lysis, and templates are sequenced (ABI Prism dye-terminator ReadyReaction mix) outward from the transposition event site, utilizing unique primers specific to the binding sites within the transposon.

Sequence data is collected (ABI Prism Collections) and assembled using Phred/Phrap (P. Green, University of Washington, Seattle). Phred/Phrap is a public domain software program which re-reads the ABI sequence data, re-calls the bases, assigns quality values, and writes the base calls and quality values into editable output files. The Phrap sequence assembly program uses these quality values to increase the accuracy of the assembled sequence contigs. Assemblies are viewed by the Consed sequence editor (D. Gordon, University of Washington, Seattle).

In some of the clones the cDNA fragment corresponds to a portion of the 3'-terminus of the gene and does not cover the entire open reading frame. In order to obtain the upstream information one of two different protocols are used. The first of these methods results in the production of a fragment of DNA containing a portion of the desired gene sequence while the second method results in the production of a fragment containing the entire open reading frame. Both of these methods use two rounds of PCR amplification to obtain fragments from one or more libraries. The libraries some times are chosen based on previous knowledge that the specific gene should be found in a certain tissue and some times are randomly-chosen. Reactions to obtain the same gene may be performed on several libraries in parallel or on a pool of libraries. Library pools are normally prepared using from 3 to 5 different libraries and normalized to a uniform dilution. In the first round of amplification both methods use a vector-specific (forward) primer corresponding to a portion of the vector located at the 5'-terminus of the clone coupled with a gene-specific (reverse) primer. The first method uses a sequence that is complementary to a portion of the already known gene sequence while the second method uses a gene-specific primer complementary to a portion of the 3'-untranslated region (also referred to as UTR). In the second round of amplification a nested set of primers is used for both methods. The resulting DNA fragment is ligated into a pBluescript vector using a commercial kit and following the manufacturer's protocol. This kit is selected from many available from several vendors including Invitrogen (Carlsbad, Calif.), Promega Biotech (Madison, Wis.), and Gibco-BRL (Gaithersburg, Md.). The plasmid DNA is isolated by alkaline lysis method and submitted for sequencing and assembly using Phred/Phrap, as above.

Example 2

Identification of cDNA Clones cDNA clones encoding trehalose metabolism enzymes were identified by conducting BLAST (Basic Local Alignment Search Tool; Altschul et al. (1993) *J. Mol. Biol.* 215:403–410; see also the explanation of the BLAST alogarithm on the world wide web site for the National Center for Biotechnology Information at the National Library of Medicine of the National Institutes of Health) searches for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). The cDNA sequences obtained in Example 1 were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish and States (1993) *Nat. Genet.* 3:266–272) provided by the NCBI. For convenience, the P-value (probability) of observing a match of a cDNA sequence to a sequence contained in the searched databases merely by chance as calculated by BLAST are reported herein as "pLog" values, which represent the negative of the logarithm of the reported P-value. Accordingly, the greater the pLog value, the greater the likelihood that the cDNA sequence and the BLAST "hit" represent homologous proteins.

ESTs submitted for analysis are compared to the genbank database as described above. ESTs that contain sequences more 5- or 3-prime can be found by using the BLASTn algorithm (Altschul et al (1997) *Nucleic Acids Res.* 25:3389–3402.) against the Du Pont proprietary database comparing nucleotide sequences that share common or overlapping regions of sequence homology. Where common or overlapping sequences exist between two or more nucleic acid fragments, the sequences can be assembled into a single contiguous nucleotide sequence, thus extending the original fragment in either the 5 or 3 prime direction. Once the most 5-prime EST is identified, its complete sequence can be determined by Full Insert Sequencing as described in Example 1. Homologous genes belonging to different species can be found by comparing the amino acid sequence of a known gene (from either a proprietary source or a public database) against an EST database using the tBLASTn algorithm. The tBLASTn algorithm searches an amino acid query against a nucleotide database that is translated in all 6 reading frames. This search allows for differences in nucleotide codon usage between different species, and for codon degeneracy.

Example 3

Characterization of cDNA Clones Encoding Alpha, Alpha-Trehalase

The BLASTX search using the EST sequences from clones listed in Table 3 revealed similarity of the polypeptides encoded by the cDNAs alpha, alpha-trehalase from *Glycine max* (NCBI General Identifier No. gi 4559292) and *Neurospora crassa* (NCBI General Identifier No. gi 3929389). Shown in Table 3 are the BLAST results for individual ESTs ("EST"), the sequences of the entire cDNA inserts comprising the indicated cDNA clones ("FIS"), the sequences of contigs assembled from two or more ESTs ("Contig"), sequences of contigs assembled from an FIS and one or more ESTs ("Contig*"), or sequences encoding an entire protein derived from an FIS, a contig, or an FIS and PCR ("CGS"):

TABLE 3

BLAST Results for Sequences Encoding Polypeptides Homologous to *Glycine max* and *Neurospora crassa* Alpha, Alpha-Trehalase

| Clone | Status | BLAST pLog Score to |
|---|---|---|
| cs1.pk0105.a2 | FIS | 133.00 (gi 4559292) |
| sdp2c.pk008.n16 | FIS | 69.70 (gi 3929389) |

The data in Table 4 represents a calculation of the percent identity of the amino acid sequences set forth in SEQ ID NOs:2 and 4 and the *Glycine max* and Neurospora crassa sequences.

TABLE 4

Percent Identity of Amino Acid Sequences Deduced From the Nucleotide Sequences of cDNA Clones Encoding Polypeptides Homologous to *Glycine max* and *Neurospora crassa* Alpha, Alpha-Trehalase

| SEQ ID NO. | Percent Identity to |
|---|---|
| 2 | 59% (gi 4559292) |
| 4 | 35% (gi 3929389) |

Sequence alignments and percent identity calculations were performed using the Megalign program of the LASERGENE bioinformatics computing suite (DNASTAR Inc., Madison, Wis.). Multiple alignment of the sequences was performed using the Clustal method of alignment (Higgins and Sharp (1989) *CABIOS.* 5:151–153) with the default parameters (GAP PENALTY=10, GAP LENGTH PENALTY=10). Default parameters for pairwise alignments using the Clustal method were KTUPLE=1, GAP PENALTY=3, WINDOW=5 and DIAGONALS SAVED=5. Sequence alignments and BLAST scores and probabilities indicate that the nucleic acid fragments comprising the instant cDNA clones encode a substantial portion of an alpha, alpha-trehalase. These sequences represent the first corn sequence and a new soybean sequence encoding alpha, alpha-trehalase, known to the Applicant.

Example 4

Characterization of cDNA Clones Encoding Alpha, Alpha-Trehalose-Phosphate Synthase The BLASTX search using the EST sequences from clones listed in Table 5 revealed similarity of the polypeptides encoded by the cDNAs alpha, alpha-trehalose-phosphate synthase from *Arabidopsis thaliana* (NCBI GI No. 6553894) and *Schizosaccharomyces pombe* (NCBI GI No. 730984). Shown in Table 5 are the BLAST results for individual ESTs ("EST"), the sequences of the entire cDNA inserts comprising the indicated cDNA clones ("FIS"), the sequences of contigs assembled from two or more ESTs ("Contig"), sequences of contigs assembled from an FIS and one or more ESTs ("Contig*"), or sequences encoding an entire protein derived from an FIS, a contig, or an FIS and PCR ("CGS"):

TABLE 5

BLAST Results for Sequences Encoding Polypeptides Homologous *Arabidopsis thaliana* and *Schizosaccharomyces pombe* Alpha, Alpha-Trehalose-Phosphate Synthase

| Clone | Status | BLAST pLog Score |
|---|---|---|
| p0102.ceraq93r | EST | 97.50 (gi 6553894) |
| rls2.pk0002.f4 | FIS | >254.00 (gi 6553894) |
| rls2.pk0004.b4 | FIS | >254.00 (gi 6553894) |
| ssm.pk0021.f9 | FIS | >254.00 (gi 6553894) |
| wlk1.pk0017.e10 | EST | 67.52 (gi 730984) |

The data in Table 6 represents a calculation of the percent identity of the amino acid sequences set forth in SEQ ID NOs:6, 8, 10, 12 and 14 and the *Arabidopsis thaliana* and *Schizosaccharomyces pombe* sequences.

TABLE 6

Percent Identity of Amino Acid Sequences Deduced From the Nucleotide Sequences of cDNA Clones Encoding Polypeptides Homologous to *Arabidopsis thaliana* and *Schizosaccharomyces pombe* Alpha, Alpha-Trehalose-Phosphate Synthase

| SEQ ID NO. | Percent Identity to |
|---|---|
| 6 | 63% (gi 6553894) |
| 8 | 59% (gi 6553894) |
| 10 | 57% (gi 6553894) |
| 12 | 64% (gi 6553894) |
| 14 | 33% (gi 730984) |

Sequence alignments and percent identity calculations were performed using the Magalign program of the LASERGENE bioinformatics computing suite (DNASTAR Inc., Madison, Wis.). Multiple alignment of the sequences was performed using the Clustal al method of alignment (Higgins and Sharp (1989) *CABIOS.* 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5. Sequence alignments and BLAST scores and probabilities indicate that the necleic acid fragments comprising the instant cDNA clones encode a substantial portion of an alpha, alpha-trehalose-phosphate synthase. These sequences represent the first corn, rice, soybean and wheat sequences encoding alpha, alpha-trehalose-phosphate synthase known to the Applicant.

Example 5

Characterization of cDNA Clones Encoding Trehalose-6-Phosphate Phosphatase

The BLASTX search using the EST sequences from clones listed in Table 7 revealed similarity of the polypeptides encoded by the cDNAs trehalose-6-phosphate phosphatase from *Arabidopsis thaliana* (NCBI GI No. 6587856), *Arabidopsis thaliana* (NCBI GI No. 2944178; AtTPPA) and *Arabidopsis thaliana* (NCBI GI No. 2944180; AtTPPB). Shown in Table 7 are the BLAST results for individual ESTs ("EST"), the sequences of the entire cDNA inserts comprising the indicated cDNA clones ("FIS"), the sequences of contigs assembled from two or more ESTs ("Contig"), sequences of contigs assembled from an FIS and one or more ESTs ("Contig*"), or sequences encoding an entire protein derived from an FIS, a contig, or an FIS and PCR ("CGS"):

TABLE 7

BLAST Results for Sequences Encoding Polypeptides Homologous to *Arabidopsis thaliana* Trehalose-6-Phosphate Phosphatase

| Clone | Status | BLAST pLog Score |
|---|---|---|
| p0006.cbyvv20r | CGS | 112.00 (gi 2944178) |
| rls72.pk0035.d8 | FIS | 55.00 (gi 6587856) |
| sls2c.pk002.e16 | CGS | 134.00 (gi 2944178) |
| srn1c.pk002.g19 | FIS | 120.00 (gi 2944180) |
| wre1n.pk187.h5 | FIS | 82.52 (gi 2944178) |

FIGS. 1A–1C show a sequence alignment of the amino acid sequences for the trehalose-6-phosphate phosphatases from corn (SEQ ID NO:16), soybean (SEQ ID NOs:20 and 22), wheat (SEQ ID NO:24) and *Arabidopsis thaliana* (AtTPPA, SEQ ID NO:37, and AtTPPB, SEQ ID NO:38). The amino acid sequence of the second soybean trehalose-6-phosphate phosphatase (SEQ ID NO:22) is almost full-length, missing approximately ten to twenty amino acids at the amino-terminus, as compared to the other soybean trehalose-6-phosphate phosphatase (SEQ ID NO:20). The amino acid sequence of the wheat trehalose-6-phosphate phosphatase (SEQ ID NO:24) corresponds to the carboxy-terminal 226 amino acids of the protein. An asterisk above an amino acid residue indicates that the position is totally conserved among the given SEQ ID NOs, with respect to the *Arabidopsis thaliana* AtTPPA sequence. Below the sequences are shown two domains, A and B, that are conserved among trehalose-6-phosphate phosphatases, as described in Vogel et al. (1998) *Plant J* 13(5):673–683. The given sequence for each conserved domain is taken from the *Arabidopsis thaliana* AtTPPA amino acid sequence at these positions. FIGS. 1A–1C indicate that regions of high sequence similarity are located in the carboxy-terminal 70% of the consensus sequence. Vogel et al. have noted that the AtTPPA and AtTPPB proteins have high sequence conservation to each other except for the amino-terminal 100 amino acids, which they note have features in common with chloroplast transit peptides. Vogel et al. have shown enzyme activity for AtTPPA, AtTPPB, and a truncated AtTPPA polypeptide that is missing the first 91 amino acids.

The data in Table 8 represents a calculation of the percent identity of the amino acid sequences set forth in SEQ ID NOs:16, 18, 20, 22 and 24 and the *Arabidopsis thaliana* sequences for AtTPPA (GI No. 2944178; SEQ ID NO:37), AtTPPB (GI No. 2944180; SEQ ID NO:38) and a variant of AtTPPB (GI No. 6587856).

TABLE 8

Percent Identity of Amino Acid Sequences Deduced From the Nucleotide Sequences of cDNA Clones Encoding Polypeptides Homologous to Trehalose-6-Phosphate Phosphatase

| SEQ ID NO. | Percent Identity to |
|---|---|
| 16 (corn) | 55% (gi 2944178; AtTPPA) |
| 18 (rice) | 54% (gi 6587856; AtTPPB) |
| 20 (soy) | 60% (gi 2944178; AtTPPA) |
| 22 (soy) | 59% (gi 2944180; AtTPPB) |
| 24 (wheat) | 64% (gi 2944178; AtTPPA) |

The data in Table 9 shows the percent identity for each pair of amino acid sequences from SEQ ID NOs:16, 18, 20, 22, 24, 37, 38 and an enzymatically active fragment of SEQ ID NO:37 in which the first 91 amino acids are missing (Vogel et al. (1998) *Plant J* 13(5):673–683).

TABLE 9

Percent Sequence Identity of Amino Acid Sequences of Plant Trehalose-6-Phosphate Phosphatases With Each Other

| SEQ | Percent Identity to SEQ ID NO: | | | | | | | |
|---|---|---|---|---|---|---|---|---|
| ID NO: | 16 | 18 | 20 | 22 | 24 | 37 | 37t* | 38 |
| 16 | — | 56% | 54% | 49% | 82% | 55% | 61% | 48% |
| 18 | 56% | — | 49% | 59% | 51% | 51% | 51% | 54% |
| 20 | 54% | 49% | — | 47% | 63% | 60% | 66% | 46% |
| 22 | 49% | 59% | 47% | — | 58% | 47% | 55% | 59% |
| 24 | 82% | 51% | 63% | 58% | — | 64% | 64% | 57% |
| 37 | 55% | 51% | 60% | 47% | 64% | — | 100% | 47% |
| 37t* | 61% | 51% | 66% | 55% | 64% | 100% | — | 55% |
| 38 | 48% | 54% | 46% | 59% | 57% | 47% | 55% | — |

*37t refers to the truncated AtTPPA polypeptide that is missing 91 amino acids from the amino terminus.

Sequence alignments and percent identity calculations were performed using the Megalign program of the LASERGENE bioinformatics computing suite (DNASTAR Inc., Madison, Wis.). Multiple alignment of the sequences was performed using the Clustal method of alignment (Higgins and Sharp (1989) CABIOS. 5:151–153) with the default parameters (GAP PENALTY=10, GAP LENGTH PENALTY=10). Default parameters for pairwise alignments using the Clustal method were KTUPLE=1, GAP PENALTY=3, WINDOW=5 and DIAGONALS SAVED=5. Sequence alignments and BLAST scores and probabilities indicate that the nucleic acid fragments comprising the instant cDNA clones encode a substantial portion of a trehalose-6-phosphate phosphatase. These sequences represent the first corn, rice, soybean and wheat sequences encoding trehalose-6-phosphate phosphatase that are known to the Applicant.

Example 6

Expression of Recombinant DNA Constructs in Monocot Cells

A recombinant DNA construct comprising a cDNA encoding one of the instant polypeptides in sense orientation with respect to the maize 27 kD zein promoter that is located 5' to the cDNA fragment, and the 10 kD zein 3' end that is located 3' to the cDNA fragment, can be constructed. The cDNA fragment of this gene may be generated by polymerase chain reaction (PCR) of the cDNA clone using appropriate oligonucleotide primers. Cloning sites (NcoI or SmaI) can be incorporated into the oligonucleotides to provide proper orientation of the DNA fragment when inserted into the digested vector pML103 as described below. Amplification is then performed in a standard PCR. The amplified DNA is then digested with restriction enzymes NcoI and SmaI and fractionated on an agarose gel. The appropriate band can be isolated from the gel and combined with a 4.9 kb NcoI-SmaI fragment of the plasmid pML103. Plasmid pML103 has been deposited under the terms of the Budapest Treaty at ATCC (American Type Culture Collection, 10801 University Blvd., Manassas, Va. 20110–2209), and bears accession number ATCC 97366. The DNA segment from pML103 contains a 1.05 kb SalI-NcoI promoter fragment of the maize 27 kD zein gene and a 0.96 kb SmaI-SalI fragment from the 3' end of the maize 10 kD zein gene in the vector pGem9Zf(+) (Promega). Vector and insert DNA can be ligated at 15° C. overnight, essentially as described (Maniatis). The ligated DNA may then be used to transform *E. coli* XL1-Blue (*Epicurian Coli* XL-1 Blue™; Stratagene). Bacterial transformants can be screened by restriction enzyme digestion of plasmid DNA and limited nucleotide sequence analysis using the dideoxy chain termination method (Sequenase™ DNA Sequencing Kit; U.S. Biochemical). The resulting plasmid construct would comprise a recombinant DNA construct encoding, in the 5' to 3' direction, the maize 27 kD zein promoter, a cDNA fragment encoding one of the instant polypeptides, and the 10 kD zein 3' region.

The recombinant DNA construct described above can then be introduced into corn cells by the following procedure. Immature corn embryos can be dissected from developing caryopses derived from crosses of the inbred corn lines H99 and LH132. The embryos are isolated 10 to 11 days after pollination when they are 1.0 to 1.5 mm long. The embryos are then placed with the axis-side facing down and in contact with agarose-solidified N6 medium (Chu et al. (1975) *Sci. Sin. Peking* 18:659–668). The embryos are kept in the dark at 27° C. Friable embryogenic callus consisting of undifferentiated masses of cells with somatic proembryoids and embryoids borne on suspensor structures proliferates from the scutellum of these immature embryos. The embryogenic callus isolated from the primary explant can be cultured on N6 medium and sub-cultured on this medium every 2 to 3 weeks.

The plasmid, p35S/Ac (obtained from Dr. Peter Eckes, Hoechst Ag, Frankfurt, Germany) may be used in transformation experiments in order to provide for a selectable marker. This plasmid contains the Pat gene (see European Patent Publication 0 242 236) which encodes phosphinothricin acetyl transferase (PAT). The enzyme PAT confers resistance to herbicidal glutamine synthetase inhibitors such as phosphinothricin. The pat gene in p35S/Ac is under the control of the 35S promoter from cauliflower mosaic virus (Odell et al. (1985) *Nature* 313:810–812) and the 3' region of the nopaline synthase gene from the T-DNA of the Ti plasmid of *Agrobacterium tumefaciens*.

The particle bombardment method (Klein et al. (1987) *Nature* 327:70–73) may be used to transfer genes to the callus culture cells. According to this method, gold particles (1 μm in diameter) are coated with DNA using the following technique. Ten μg of plasmid DNAs are added to 50 μL of a suspension of gold particles (60 mg per mL). Calcium chloride (50 μL of a 2.5 M solution) and spermidine free base (20 μL of a 1.0 M solution) are added to the particles. The suspension is vortexed during the addition of these solutions. After 10 minutes, the tubes are briefly centrifuged (5 sec at 15,000 rpm) and the supernatant removed. The particles are resuspended in 200 μL of absolute ethanol, centrifuged again and the supernatant removed. The ethanol rinse is performed again and the particles resuspended in a final volume of 30 μL of ethanol. An aliquot (5 μL) of the DNA-coated gold particles can be placed in the center of a Kapton™ flying disc (Bio-Rad Labs). The particles are then accelerated into the corn tissue with a Biolistic™ PDS-1000/He (Bio-Rad Instruments, Hercules Calif.), using a helium pressure of 1000 psi, a gap distance of 0.5 cm and a flying distance of 1.0 cm.

For bombardment, the embryogenic tissue is placed on filter paper over agarose-solidified N6 medium. The tissue is arranged as a thin lawn and covered a circular area of about 5 cm in diameter. The petri dish containing the tissue can be placed in the chamber of the PDS-1000/He approximately 8 cm from the stopping screen. The air in the chamber is then evacuated to a vacuum of 28 inches of Hg. The macrocarrier is accelerated with a helium shock wave using a rupture membrane that bursts when the He pressure in the shock tube reaches 1000 psi.

Seven days after bombardment the tissue can be transferred to N6 medium that contains bialophos (5 mg per liter) and lacks casein or proline. The tissue continues to grow slowly on this medium. After an additional 2 weeks the tissue can be transferred to fresh N6 medium containing bialophos. After 6 weeks, areas of about 1 cm in diameter of actively growing callus can be identified on some of the plates containing the bialophos-supplemented medium. These calli may continue to grow when sub-cultured on the selective medium.

Plants can be regenerated from the transgenic callus by first transferring clusters of tissue to N6 medium supplemented with 0.2 mg per liter of 2,4-D. After two weeks the tissue can be transferred to regeneration medium (Fromm et al. (1990) *Bio/Technology* 8:833–839).

Example 7

Expression of Recombinant DNA Constructs in Dicot Cells

A seed-specific expression cassette composed of the promoter and transcription terminator from the gene encoding the β subunit of the seed storage protein phaseolin from the bean *Phaseolus vulgaris* (Doyle et al. (1986) *J. Biol. Chem.* 261:9228–9238) can be used for expression of the instant polypeptides in transformed soybean. The phaseolin cassette includes about 500 nucleotides upstream (5') from the translation initiation codon and about 1650 nucleotides downstream (3') from the translation stop codon of phaseolin. Between the 5' and 3' regions are the unique restriction endonuclease sites NcoI (which includes the ATG translation initiation codon), SmaI, KpnI and XbaI. The entire cassette is flanked by HindIII sites.

The cDNA fragment of this gene may be generated by polymerase chain reaction (PCR) of the cDNA clone using appropriate oligonucleotide primers. Cloning sites can be incorporated into the oligonucleotides to provide proper orientation of the DNA fragment when inserted into the expression vector. Amplification is then performed as described above, and the isolated fragment is inserted into a pUC18 vector carrying the seed expression cassette.

Soybean embryos may then be transformed with the expression vector comprising sequences encoding the instant polypeptides. To induce somatic embryos, cotyledons, 3–5 mm in length dissected from surface sterilized, immature seeds of the soybean cultivar A2872, can be cultured in the light or dark at 26° C. on an appropriate agar medium for 6–10 weeks. Somatic embryos which produce secondary embryos are then excised and placed into a suitable liquid medium. After repeated selection for clusters of somatic embryos which multiplied as early, globular staged embryos, the suspensions are maintained as described below.

Soybean embryogenic suspension cultures can be maintained in 35 mL liquid media on a rotary shaker, 150 rpm, at 26° C. with florescent lights on a 16:8 hour day/night schedule. Cultures are subcultured every two weeks by inoculating approximately 35 mg of tissue into 35 mL of liquid medium.

Soybean embryogenic suspension cultures may then be transformed by the method of particle gun bombardment (Klein et al. (1987) *Nature* (London) 327:70–73, U.S. Pat. No. 4,945,050). A DuPont Biolistic™ PDS1000/HE instrument (helium retrofit) can be used for these transformations.

A selectable marker gene which can be used to facilitate soybean transformation is a chimeric gene composed of the 35S promoter from cauliflower mosaic virus (Odell et al. (1985) *Nature* 313:810–812), the hygromycin phosphotransferase gene from plasmid pJR225 (from *E. coli*; Gritz et al. (1983) *Gene* 25:179–188) and the 3' region of the nopaline synthase gene from the T-DNA of the Ti plasmid of *Agrobacterium tumefaciens*. The seed expression cassette comprising the phaseolin 5' region, the fragment encoding one of the instant polypeptides and the phaseolin 3' region can be isolated as a restriction fragment. This fragment can then be inserted into a unique restriction site of the vector carrying the marker gene.

To 50 μL of a 60 mg/mL 1 μm gold particle suspension is added (in order): 5 μL DNA (1 μg/μL), 20 μL spermidine (0.1 M), and 50 μL $CaCl_2$ (2.5 M). The particle preparation is then agitated for three minutes, spun in a microfuge for 10 seconds and the supernatant removed. The DNA-coated particles are then washed once in 400 μL 70% ethanol and resuspended in 40 μL of anhydrous ethanol. The DNA/particle suspension can be sonicated three times for one second each. Five μL of the DNA-coated gold particles are then loaded on each macro carrier disk.

Approximately 300–400 mg of a two-week-old suspension culture is placed in an empty 60×1 5 mm petri dish and the residual liquid removed from the tissue with a pipette. For each transformation experiment, approximately 5–10 plates of tissue are normally bombarded. Membrane rupture pressure is set at 1100 psi and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post bombardment with fresh media containing 50 mg/mL hygromycin. This selective media can be refreshed weekly. Seven to eight weeks post bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example 8

Expression of Recombinant DNA Constructs in Microbial Cells

The cDNAs encoding the instant polypeptides can be inserted into the T7 *E. coli* expression vector pBT430. This vector is a derivative of pET-3a (Rosenberg et al. (1987) *Gene* 56:125–135) which employs the bacteriophage T7 RNA polymerase/T7 promoter system. Plasmid pBT430 was constructed by first destroying the EcoRI and HindIII sites in pET-3a at their original positions. An oligonucleotide adaptor containing EcoRI and Hind III sites was inserted at the BamHI site of pET-3a. This created pET-3aM with additional unique cloning sites for insertion of genes into the expression vector. Then, the NdeI site at the position of translation initiation was converted to an NcoI site using oligonucleotide-directed mutagenesis. The DNA sequence of pET-3aM in this region, 5'-CATATGG, was converted to 5'-CCCATGG in pBT430.

Plasmid DNA containing a cDNA may be appropriately digested to release a nucleic acid fragment encoding the protein. This fragment may then be purified on a 1% low melting agarose gel. Buffer and agarose contain 10 μg/ml ethidium bromide for visualization of the DNA fragment. The fragment can then be purified from the agarose gel by digestion with GELase™ (Epicentre Technologies, Madison, Wis.) according to the manufacturer's instructions, ethanol precipitated, dried and resuspended in 20 μL of water. Appropriate oligonucleotide adapters may be ligated to the fragment using T4 DNA ligase (New England Biolabs (NEB), Beverly, Mass.). The fragment containing the ligated adapters can be purified from the excess adapters using low melting agarose as described above. The vector pBT430 is digested, dephosphorylated with alkaline phosphatase (NEB) and deproteinized with phenol/chloroform as described above. The prepared vector pBT430 and fragment can then be ligated at 16° C. for 15 hours followed by transformation into DH5 electrocompetent cells (GIBCO BRL). Transformants can be selected on agar plates containing LB media and 100 μg/mL ampicillin. Transformants containing the gene encoding the instant polypeptide are then screened for the correct orientation with respect to the T7 promoter by restriction enzyme analysis.

For high level expression, a plasmid clone with the cDNA insert in the correct orientation relative to the T7 promoter can be transformed into E. coli strain BL21 (DE3) (Studier et al. (1986) *J. Mol. Biol.* 189:113–130). Cultures are grown in LB medium containing ampicillin (100 mg/L) at 25° C. At an optical density at 600 nm of approximately 1, IPTG (isopropylthio-p-galactoside, the inducer) can be added to a final concentration of 0.4 mM and incubation can be continued for 3 h at 25°. Cells are then harvested by centrifugation and re-suspended in 50 μL of 50 mM Tris-HCl at pH 8.0 containing 0.1 mM DTT and 0.2 mM phenyl methylsulfonyl fluoride. A small amount of 1 mm glass beads can be added and the mixture sonicated 3 times for about 5 seconds each time with a microprobe sonicator. The mixture is centrifuged and the protein concentration of the supernatant determined. One μg of protein from the soluble fraction of the culture can be separated by SDS-polyacrylamide gel electrophoresis. Gels can be observed for protein bands migrating at the expected molecular weight. Alpha, alpha-trehalase acitivity can be determined by the method of Kalf and Rieder (1958) *J Biol Chem* 230:691–698. Alpha, alpha-trehalose-phosphate synthase activity can be determined by the method of Blazquez et al. (1998) *Plant J* 13:685–689. Trehalose-6-phosphate phosphatase activity can be determined by the method of Vogel, G. et al. (1998) *Plant J* 13(5):673–683.

Example 9

Expression of Recombinant DNA Constructs in Yeast Cells

The polypeptides encoded by the polynucleotides of the instant invention may be expressed in a yeast (*Saccharomyces cerevisiae*) strain YPH. Plasmid DNA may be used as template to amplify the portion encoding the alpha, alpha-trehalase, alpha, alpha-trehalose-phosphate synthase or trehalose-6-phosphate phosphatase. Amplification may be performed using the GC melt kit (Clontech) with a 1 M final concentration of GC melt reagent and using a Perkin Elmer 9700 thermocycler. The amplified insert may then be incubated with a modified pRS315 plasmid (NCBI General Identifier No. 984798; Sikorski, R. S. and Hieter, P. (1989) *Genetics* 122:19–27) that has been digested with Not I and Spe I. Plasmid pRS315 has been previously modified by the insertion of a bidirectional gall/10 promoter between the Xho I and Hind III sites. The plasmid may then be transformed into the YPH yeast strain using standard procedures where the insert recombines through gap repair to form the desired transformed yeast strain (Hua, S. B. et al. (1997) *Plasmid* 38:91–96).

Yeast cells may be prepared according to a modification of the methods of Pompon et al. (Pompon, D. et al. (1996) *Meth. Enz.* 272:51–64). Briefly, a yeast colony will be grown overnight (to saturation) in SG (-Leucine) medium at 30° C. with good aeration. A 1:50 dilution of this culture will be made into 500 mL of YPGEi medium with adenine supplementation and allowed to grow at 30° C. with good aeration to an $OD_{600}$ of 1.6 (24–30 h). Fifty mL of 20% galactose will be added, and the culture allowed to grow overnight at 30° C. The cells will be recovered by centrifugation at 5,500 rpm for five minutes in a Sorvall GS-3 rotor. The cell pellet resuspended in 500 mL of 0.1 M potassium phosphate buffer (pH 7.0) and then allowed to grow at 30° C. for another 24 hours.

The cells may be recovered by centrifugation as described above and the presence of the polypeptide of the instant invention determined by HPLC/mass spectrometry or any other suitable method.

Example 10

Expression of Recombinant DNA Constructs in Insect Cells

The cDNAs encoding the instant polypeptides may be introduced into the baculovirus genome itself. For this purpose the cDNAs may be placed under the control of the polyhedron promoter, the IE1 promoter, or any other one of the baculovirus promoters. The cDNA, together with appropriate leader sequences is then inserted into a baculovirus transfer vector using standard molecular cloning techniques. Following transformation of *E. coli* DH5a, isolated colonies are chosen and plasmid DNA is prepared and is analyzed by restriction enzyme analysis. Colonies containing the appropriate fragment are isolated, propagated, and plasmid DNA is prepared for cotransfection.

*Spodoptera frugiperda* cells (Sf-9) are propagated in ExCell®401 media (JRH Biosciences, Lenexa, Kans.) supplemented with 3.0% fetal bovine serum. Lipofectin® (50 μL at 0.1 mg/mL, Gibco/BRL) is added to a 50 μL aliquot of the transfer vector containing the toxin gene (500 ng) and linearized polyhedrin-negative AcNPV (2.5 μg, Baculogold® viral DNA, Pharmigen, San Diego, Calif.). Sf-9 cells (approximate 50% monolayer) are co-transfected with the viral DNA/transfer vector solution. The supernatant fluid from the co-transfection experiment is collected at 5 days post-transfection and recombinant viruses are isolated employing standard plaque purification protocols, wherein only polyhedrin-positive plaques are selected (O'Reilly et al. (1992), *Baculovirus Expression Vectors: A Laboratory Manual*, W. H. Freeman and Company, New York.). Sf-9 cells in 35 mM petri dishes (50% monolayer) are inoculated with 100 μL of a serial dilution of the viral suspension, and supernatant fluids are collected at 5 days post infection. In order to prepare larger quantities of virus for characterization, these supernatant fluids are used to inoculate larger tissue cultures for large-scale propagation of recombinant viruses. Expression of the instant polypeptides encoded by the recombinant baculovirus is confirmed by any of the methods mentioned in Example 8.

What is claimed is:

1. An isolated polynucleotide comprising:

(a) a nucleoticle sequence encoding a polypeptide having trehalose-6-phosphate phosphatase activity, wherein the polypepticie has an amino acid sequence of at least 95% sequence identity when compared to SEQ ID NQ:16, or (b) the complement of the nucleotide sequence of (a), wherein the complement and the nucleotide sequence consist of the same number of nucleotides and are 100% complementary.

2. The polynucleotide of claim 1, wherein the amino acid sequence of the polypeptide comprises SEQ ID NO:16.

3. The polynucleotide of claim 1 wherein the nucleotide sequence comprises SEQ ID NO:15.

4. A vector comprising the polynucleotide of claim 1.

5. A recombinant DNA construct comprising the polynucleotide of claim 1 operably linked to at least one regulatory sequence.

6. A method for transforming a cell, wherein the method comprises transforming a cell with the polynucleotide of claim 1.

7. A cell comprising the recombinant DNA construct of claim 5.

8. A method for producing a plant, wherein the method comprises transforming a plant cell with the polynucleotide of claim 1 and regenerating a plant from the transformed plant cell.

9. A plant comprising the recombinant DNA construct of claim 5.

10. A seed comprising the recombinant DNA construct of claim 5.

11. A method for isolating a polypeptide having trehalose-6-phosphate phosphatase activity, wherein the method comprises isolating the polypeptide from a cell or culture medium of the cell, wherein the cell comprises a recombinant DNA construct comprising the polynucleotide of claim 1 operably linked to at least one regulatory sequence.

12. A method of altering the level of expression of a trehalose-6-phosphate phosphatase in a host cell, wherein the method comprises:

(a) transforming a host cell with the recombinant DNA construct of claim 5; and (b) growing the transformed host ceU under conditions that are suitable for expression of the recombinant DNA construct wherein expression of the recombinant DNA construct results in production of altered levels of the trehalose-6-phosphate phosphatase in the transformed host cell.

* * * * *

UNITED STATES PATENT AND TRADEMARK OFFICE

CERTIFICATE OF CORRECTION

PATENT NO. : 7,214,858 B2
APPLICATION NO. : 10/365970
DATED : May 8, 2007
INVENTOR(S) : Perry G. Caimi, Saverio Carl Falco and Zude Weng It is certified that error appears in the above-identified patent and that said Letters Patent is hereby corrected as shown below:

Col. 99, line 52;

Last page of patent, Claims section, Claim 1(a): please delete “nucleoticle” and insert therefor --nucleotide--.

Col. 99, line 54;

Last page of patent, Claims section, Claim 1(a): please delete “polypepticie” and insert therefor --polypeptide--.

Col. 102, line 3;

Last page of patent, Claims section, Claim 12(b): please delete “CeU” and insert therefor --cell--.

Signed and Sealed this

Third Day of July, 2007

JON W. DUDAS

*Director of the United States Patent and Trademark Office*

SEQUENCE LISTING

```
<160> NUMBER OF SEQ ID NOS: 38

<210> SEQ ID NO 1
<211> LENGTH: 1358
<212> TYPE: DNA
<213> ORGANISM: Zea mays

<400> SEQUENCE: 1

gcacgaggca agatcctact acactaaccg aagccaacca ccacttttga gctccatggt     60

tttagaaata tacagggcaa ctggtgatgt ggagtttgtt aggacagtat tccactctct    120

gcttaaagag catagcttct ggatgtcaga gattcataat gttgctatag cagacaatca    180

tggtcgggtc cataatttat ctcggtatca ggccaggtgg aacaaaccta ggcctgaaag    240

tgcgacaatt gatgaggaac tggcttcgaa gttgaattct atggcagcta aggaaaaact    300

gtactgcgaa attgcttcaa cggcagaatc gggatgggat ttcagctctc gatggatgag    360

gaattctact gacatgacaa cattggcaac cacttacata atacctgtgg acttgaacac    420

atttcttttt aagatggagc tggatattgg tgccttggct aaagtcgtag gagataatgc    480

gacttcagaa ttttttttaa atgcttcgaa agcacgtcat attgcaattg actctatttt    540

gtggaactct gagatggaac agtggcttga ctattggctt cctggtgatg cagactgtca    600

ggaagtacac gaatggaagc ctaactcaca gaaccgcaac atatttgctt ccaacttcgt    660

tccgctgtgg ctaaatgcat accattccga attcgtacgc tttgctgatg aggcaaaatc    720

aaacagagtc atggcgagcc tcaaggcatc tggattactt catgccgcag ggatagcaac    780

ttccctgaca aacacgagcc aacaatggga tttcccgaat ggatgggccc cactgcagca    840

tcttatagct gaggggctgc tgcattctgg atcagaggcc aaaaaactag ctgaggacat    900

tgctacgagg tgggtgagaa cgaactacgc cgcttacaaa gcaacgggtg cgatgcatga    960

gaagtacgat gttgaggctt gtggagaatc tggaggcggt ggagaataca agccccagac   1020

tggttttggc tggtccaatg gcgtggtgtt gtcattcttg gaagaattcg ggtggccaga   1080

gggcaaggaa atagcttgtt gagcggcgaa gcgctcacga cagggtggat ctggtcttgc   1140

cggagagcaa tctggttagg catcgttcat gtcacacatg tctagctacg agagtggcgc   1200

attgccttct gcagttcgtc aagtgcgttt gtgtgttctt gtttgctttt agttgcgact   1260

aggctgtaga tccttcttgt atcacaacaa tatatgtact gctactgtac cggccccggc   1320

ctcttgttta atctgaaatg ctcattgtat atcctctt                            1358
```

-continued

```
<210> SEQ ID NO 2
<211> LENGTH: 366
<212> TYPE: PRT
<213> ORGANISM: Zea mays

<400> SEQUENCE: 2

His Glu Ala Arg Ser Tyr Tyr Thr Asn Arg Ser Gln Pro Pro Leu Leu
  1               5                  10                  15

Ser Ser Met Val Leu Glu Ile Tyr Arg Ala Thr Gly Asp Val Glu Phe
             20                  25                  30

Val Arg Thr Val Phe His Ser Leu Leu Lys Glu His Ser Phe Trp Met
         35                  40                  45

Ser Glu Ile His Asn Val Ala Ile Ala Asp Asn His Gly Arg Val His
     50                  55                  60

Asn Leu Ser Arg Tyr Gln Ala Arg Trp Asn Lys Pro Arg Pro Glu Ser
 65                  70                  75                  80

Ala Thr Ile Asp Glu Glu Leu Ala Ser Lys Leu Asn Ser Met Ala Ala
                 85                  90                  95

Lys Glu Lys Leu Tyr Cys Glu Ile Ala Ser Thr Ala Glu Ser Gly Trp
            100                 105                 110

Asp Phe Ser Ser Arg Trp Met Arg Asn Ser Thr Asp Met Thr Thr Leu
        115                 120                 125

Ala Thr Thr Tyr Ile Ile Pro Val Asp Leu Asn Thr Phe Leu Phe Lys
    130                 135                 140

Met Glu Leu Asp Ile Gly Ala Leu Ala Lys Val Val Gly Asp Asn Ala
145                 150                 155                 160

Thr Ser Glu Phe Phe Leu Asn Ala Ser Lys Ala Arg His Ile Ala Ile
                165                 170                 175

Asp Ser Ile Leu Trp Asn Ser Glu Met Glu Gln Trp Leu Asp Tyr Trp
            180                 185                 190

Leu Pro Gly Asp Ala Asp Cys Gln Glu Val His Glu Trp Lys Pro Asn
        195                 200                 205

Ser Gln Asn Arg Asn Ile Phe Ala Ser Asn Phe Val Pro Leu Trp Leu
    210                 215                 220

Asn Ala Tyr His Ser Glu Phe Val Arg Phe Ala Asp Glu Ala Lys Ser
225                 230                 235                 240

Asn Arg Val Met Ala Ser Leu Lys Ala Ser Gly Leu Leu His Ala Ala
                245                 250                 255

Gly Ile Ala Thr Ser Leu Thr Asn Thr Ser Gln Gln Trp Asp Phe Pro
            260                 265                 270

Asn Gly Trp Ala Pro Leu Gln His Leu Ile Ala Glu Gly Leu Leu His
        275                 280                 285

Ser Gly Ser Glu Ala Lys Lys Leu Ala Glu Asp Ile Ala Thr Arg Trp
    290                 295                 300

Val Arg Thr Asn Tyr Ala Ala Tyr Lys Ala Thr Gly Ala Met His Glu
305                 310                 315                 320

Lys Tyr Asp Val Glu Ala Cys Gly Glu Ser Gly Gly Gly Gly Glu Tyr
                325                 330                 335

Lys Pro Gln Thr Gly Phe Gly Trp Ser Asn Gly Val Val Leu Ser Phe
            340                 345                 350

Leu Glu Glu Phe Gly Trp Pro Glu Gly Lys Glu Ile Ala Cys
        355                 360                 365
```

-continued

<210> SEQ ID NO 3
<211> LENGTH: 1409
<212> TYPE: DNA
<213> ORGANISM: Glycine max

<400> SEQUENCE: 3

```
gcacgagcct caactcgtta ttgtacaagt acgagtcgga tatttacact gccatcgagc     60
aagtctttgg gggtgaactc gaaatggacg aagagtttga actctcgcca tggcccatca    120
ctgctgaggc tttcgccgag ggtgctgcac gtgaactctc gacatcccgc gttcaaacgg    180
cggccgagtg gaaggaacgc atggataagc gtcgtgatac gatgaatgag ctctgctgga    240
atgagggacg aggaatgttc tttgactggg ataccaaggc gcagaaacag gccaaatacg    300
agagtgttac ctgtctctgg ccactctggg ctggaaatgc gtccgaggat caggcaatga    360
agatggtcaa tatggctcta cccaagtttg aggtcgctgg cgggcttgtt tcgggaacag    420
aggagagccg aggtatcatc tcgatcgatc gaccgaatcg acagtgggat taccctttca    480
gctggccgcc gcatcagatt atgacttggg tcgggcttga gcgatacgga cacgataccc    540
acgctgcccg tcttgcgtac cgttggatct acatgatgac attgtccttt gtcgatttca    600
acggcattgt tcccgagaag tttgatgctg tcgagttgag ccacatggtg gatgccgagt    660
atggtaatca gggtactgat ttccgttatg ttccccgaga gggtttcggc tggatgaatg    720
ctgcttacca agttggattg caattcttgt ctattggtat gcgccgagcg gtagctgctt    780
gtgttcctcc atgggtcttt ttcaatctcc ccgcccccga cttcccctcg gcgcgtcgtc    840
gtcgtgcgga acgcgaggcc cgcgaagccg atgctgcggc ccagggtcat ggtggacagc    900
ctaaacagca ggtacatcac gaaccgccga gtctcgagca ggctattgcc aacctcaaga    960
ttgatcttgg cacgggcacg gcgtagaatt acaagagatg ggtagacgat tgtgcaggat   1020
gctgtgaatt cttttgcgaa attcgaatgc gaaatacgag gatgattgtg aaggtctgat   1080
atcgtctctg acttgcgggt cgcgggcaag gtgtgagaca attcctcctc tacgagaatg   1140
ggcataatga ggaaaatgag aaacaggtat actcagtctg cttttttttc catcaaagaa   1200
attctcttct tttgtcattg tattcattca ctctttccgt gtgcgggata gcagcagcgg   1260
agcacggggt cgagggttgt ttagcaagag ttttctctct acaagcgcat gcattacatt   1320
ttgtgacgga tgaaaaaaaa aaaaaaaaaa aaaaaaaaaa aaaaaaaaaa aaaaaaaaaa   1380
aaaaaaataa aaataaaaaa aaaaaacccc                                    1409
```

<210> SEQ ID NO 4
<211> LENGTH: 327
<212> TYPE: PRT
<213> ORGANISM: Glycine max

<400> SEQUENCE: 4

```
Thr Ser Leu Asn Ser Leu Leu Tyr Lys Tyr Glu Ser Asp Ile Tyr Thr
  1               5                  10                  15

Ala Ile Glu Gln Val Phe Gly Gly Glu Leu Glu Met Asp Glu Glu Phe
             20                  25                  30

Glu Leu Ser Pro Trp Pro Ile Thr Ala Glu Ala Phe Ala Glu Gly Ala
         35                  40                  45

Ala Arg Glu Leu Ser Thr Ser Arg Val Gln Thr Ala Ala Glu Trp Lys
     50                  55                  60

Glu Arg Met Asp Lys Arg Arg Asp Thr Met Asn Glu Leu Cys Trp Asn
 65                  70                  75                  80

Glu Gly Arg Gly Met Phe Phe Asp Trp Asp Thr Lys Ala Gln Lys Gln
```

-continued

```
                85                  90                  95

Ala Lys Tyr Glu Ser Val Thr Cys Leu Trp Pro Leu Trp Ala Gly Asn
            100                 105                 110

Ala Ser Glu Asp Gln Ala Met Lys Met Val Asn Met Ala Leu Pro Lys
        115                 120                 125

Phe Glu Val Ala Gly Gly Leu Val Ser Gly Thr Glu Glu Ser Arg Gly
    130                 135                 140

Ile Ile Ser Ile Asp Arg Pro Asn Arg Gln Trp Asp Tyr Pro Phe Ser
145                 150                 155                 160

Trp Pro Pro His Gln Ile Met Thr Trp Val Gly Leu Glu Arg Tyr Gly
                165                 170                 175

His Asp Thr His Ala Ala Arg Leu Ala Tyr Arg Trp Ile Tyr Met Met
            180                 185                 190

Thr Leu Ser Phe Val Asp Phe Asn Gly Ile Val Pro Glu Lys Phe Asp
        195                 200                 205

Ala Val Glu Leu Ser His Met Val Asp Ala Glu Tyr Gly Asn Gln Gly
    210                 215                 220

Thr Asp Phe Arg Tyr Val Pro Arg Glu Gly Phe Gly Trp Met Asn Ala
225                 230                 235                 240

Ala Tyr Gln Val Gly Leu Gln Phe Leu Ser Ile Gly Met Arg Arg Ala
                245                 250                 255

Val Ala Ala Cys Val Pro Pro Trp Val Phe Phe Asn Leu Pro Ala Pro
            260                 265                 270

Asp Phe Pro Ser Ala Arg Arg Arg Arg Ala Glu Arg Glu Ala Arg Glu
        275                 280                 285

Ala Asp Ala Ala Ala Gln Gly His Gly Gly Gln Pro Lys Gln Gln Val
    290                 295                 300

His His Glu Pro Pro Ser Leu Glu Gln Ala Ile Ala Asn Leu Lys Ile
305                 310                 315                 320

Asp Leu Gly Thr Gly Thr Ala
                325
```

<210> SEQ ID NO 5
<211> LENGTH: 749
<212> TYPE: DNA
<213> ORGANISM: Zea mays

<400> SEQUENCE: 5

```
ccacgcgtcc gccaactacc tgctggccaa tttctcgtgc ctgccggtgt accttcccac     60

cgacctccac caccgcttct accacggatt ctgcaagcac tacctctggc cgctcctcca    120

ctacctcctc ccgctgacgc cgtcctcgct cggtggcctc cctttccagc gaacgctcta    180

ccactccttc ctctcggcaa acagggcgtt cgccgaccgc ctcaccgagg tgctgtcccc    240

cgacgaggac ctcgtctgga tccacgatta ccacctcctc gcgctcccga ccttcctccg    300

caagcgcttc ccgcgcgcca aggtcggatt cttcctccac tcacccttcc cctcgtcgga    360

gatcttccgt acgatccccg tgcgggatga cctcgtccgc gcactcctca acgccgacct    420

cgtcggcttc cacaccttcg actacgcgcg ccacttcctg tccgcgtgct cgcggctgct    480

cggcctcgac taccagtcca agcgcggcta catcggcatc gagtattacg gccgcaccgt    540

gactgtcaag atactccccg ttgggatcga catggggcag ctcagatcgg tggtctcggc    600

gccggagacg gaggacgcgg tgcggcgggt gacagaggcg tacaagggaa ggcgcctcat    660

ggtaggcgtc gacgacgtcg atctgttcaa ggggatcggg ctcaagttcc tggcgatgga    720
```

```
gcagctgctc gtggagcacc gggagctcc                                       749


<210> SEQ ID NO 6
<211> LENGTH: 249
<212> TYPE: PRT
<213> ORGANISM: Zea mays

<400> SEQUENCE: 6

His Ala Ser Ala Asn Tyr Leu Leu Ala Asn Phe Ser Cys Leu Pro Val
  1               5                  10                  15

Tyr Leu Pro Thr Asp Leu His His Arg Phe Tyr His Gly Phe Cys Lys
             20                  25                  30

His Tyr Leu Trp Pro Leu Leu His Tyr Leu Leu Pro Leu Thr Pro Ser
         35                  40                  45

Ser Leu Gly Gly Leu Pro Phe Gln Arg Thr Leu Tyr His Ser Phe Leu
     50                  55                  60

Ser Ala Asn Arg Ala Phe Ala Asp Arg Leu Thr Glu Val Leu Ser Pro
 65                  70                  75                  80

Asp Glu Asp Leu Val Trp Ile His Asp Tyr His Leu Leu Ala Leu Pro
                 85                  90                  95

Thr Phe Leu Arg Lys Arg Phe Pro Arg Ala Lys Val Gly Phe Phe Leu
            100                 105                 110

His Ser Pro Phe Pro Ser Ser Glu Ile Phe Arg Thr Ile Pro Val Arg
        115                 120                 125

Asp Asp Leu Val Arg Ala Leu Leu Asn Ala Asp Leu Val Gly Phe His
    130                 135                 140

Thr Phe Asp Tyr Ala Arg His Phe Leu Ser Ala Cys Ser Arg Leu Leu
145                 150                 155                 160

Gly Leu Asp Tyr Gln Ser Lys Arg Gly Tyr Ile Gly Ile Glu Tyr Tyr
                165                 170                 175

Gly Arg Thr Val Thr Val Lys Ile Leu Pro Val Gly Ile Asp Met Gly
            180                 185                 190

Gln Leu Arg Ser Val Val Ser Ala Pro Glu Thr Glu Asp Ala Val Arg
        195                 200                 205

Arg Val Thr Glu Ala Tyr Lys Gly Arg Arg Leu Met Val Gly Val Asp
    210                 215                 220

Asp Val Asp Leu Phe Lys Gly Ile Gly Leu Lys Phe Leu Ala Met Glu
225                 230                 235                 240

Gln Leu Leu Val Glu His Arg Glu Leu
                245


<210> SEQ ID NO 7
<211> LENGTH: 3083
<212> TYPE: DNA
<213> ORGANISM: Oryza sativa

<400> SEQUENCE: 7

gcacgaggcg gatgtcgcgg gtgatgacgg tgcccgggac gctgtcggag ctggacgggg      60

aggacgactc ggagcacgcg gcgacgaaca gcgtcgcctc cgacgtgccc tcgtcggtgg     120

cgggggatcg agtcatagtg gtctccaacc agctgcccgt cgtcgcacgc cgccgtcccg     180

acggccgcgg gtggtccttc tcatgggacg acgactcgct gctcctccag ctccgcgacg     240

gcattcccga tgagatggag gtgttcttcg tcggttccct ccgcgccgaa atccccgtcg     300

ccgaccagga agaggtctcc caggcgctgc tcgatcgctt ccgatgtgct ccggtgttcc     360

tccccgaccc cctcaacgaa cggttttacc accgcttctg caagcgccac ctatggcctc     420
```

-continued

```
tgttccacta catgctccct ttctcctcct ccgcatcccc gagtccctcc tcctcctcct    480
cctcctcctc ctccccctca tcctcatccg gcagtggcca cttcgaccgc ggcgcgtggg    540
aggcctacgt gctcgcgaac aagttcttct tcgagaaggt cgtggaggtc atcaacccag    600
aagacgacta cgtatgggtt cacgactacc atctcatggc gctgcccacc ttccttcgcc    660
gccgcttcaa ccgcctgcgc atcggcttct tcctccacag ccccttcccc tcgtcggaga    720
tctaccggac cctccctgtt cgcgaggaga tcctaaaggc gctgctcaat tgtgacctta    780
ttggattcca cacttttgac tatgccagac atttcctctc ttgttgtagt aggatgctgg    840
gaattgaata ccagtcaaag cgtggataca ttgggttgga ttactttggg cgtaccgttg    900
ggatcaaaat catgccagtg ggagttcata tgggtcaatt gaagacggtt ctgagcttgc    960
ccgacaggga atggagggtc tccgagctgc agcagcaatt tgaggggaag actgtgttgc   1020
tcggtgtgga tgacatggat atcttcaagg gtatcaactt gaagcttctt gccttcgaga   1080
atatgttgag gacacatccc aagtggcagg ggcgggcagt gttggtgcaa attgctaatc   1140
cggcccgtgg aaagggtaag gatcttgaag ccatccaggc tgagattcat gagagctgca   1200
agaggattaa tggagagttt ggccagtcag gatacagccc tgttgtcttc attgaccgtg   1260
atgtgtcaag tgtggagaag attgcctact acacaatagc agaatgtgtg gtggtgactg   1320
ctgtgaggga tgggatgaac ttgacaccat atgaatatat tgtctgtagg caggggtctg   1380
actccacatc agaagtgaat ggaccaaaga agagcatgct ggtggtatca gaattcattg   1440
ggtgctcacc atctctgagt ggtgctatcc gggttaaccc atggaatata gaggcaaccg   1500
cagaggcact gaatgaggcc atatcaatgt cggaacagga gaaacaccta aggcatgaga   1560
aacattaccg ttatgtcagc acccacgatg ttgcttattg gtcgaaaagt ttcatccaag   1620
atttggagag ggcttgcaag gaccacttca ggaggacatg ttggggcatc gggttggggt   1680
ttggttttag ggtggtggcc ttagatcccc atttcacaaa gcttaacatg gattcaattg   1740
ttatggctta tgagcggtca gagagtaggg ctatatttct tgattatgat ggaacactgg   1800
tgccacagac ttccatcagt aggacaccta gtgcggaagt tttgaggatc atcaataccc   1860
tgtgctcaga taggaggaac aaagtttttc ttgtcagtgg gagacgcagg gacaaattgg   1920
gagaatggtt ttcctcttgt ccagatctgg gcattgcagc agagcatggt tacttcttaa   1980
ggtggactag agacgaagag tggcaaacat gtacccagac ctctgacttc gggtggatgg   2040
aaatggccaa gccagtgatg aatctgtata cagaagcaac tgatggatct tacattgatc   2100
ctaaggaaag tgctttggtg tggcatcacc aggatgctga cccaggattt ggatcctccc   2160
aggcaaagga gttacttgat catctggaaa gtgtattagc aaatgaacct gtttctgtca   2220
aaagtggcca gttcattgtt gaagtcaaac ctcagggagt aagcaaggga gtagtagctg   2280
agaagatact cgtctcaatg aaggagagag gaaagcaggc tgactttgta ttatgcattg   2340
gtgatgacag gtcggatgag gacatgtttg aaaacattgc tgataccatt aaaaagggta   2400
tggttgctac aaacacatca ttgtttgcat gcactgtggg acaaaaacca agcaaggcca   2460
aattttacct ggatgatacg tttgaagtgg tcaccatgct gagcgcactg gcagatgcta   2520
ctgaaccaga acctgagact gatcttaccg atgagtttga tgaactggcc gtgtctgtct   2580
cctcagttga tattgatgat gaacaaacgc ccagtgataa actgatcgga ggatagtagt   2640
caaggttgct tatatctgca gattgtcatg attaattcaa ccatctctat acaatttttg   2700
atgaatgtga aagctgggta ctcaaagaat gactaacacc aggccctacg aatgctccag   2760
```

```
tgtgaagtta ataccgtgga gtgctcgatt ctccactggg ggcaaaagcc aatacaatct   2820

tgtgctggaa aagtaggtcc atatgtccat agctgacttc acttttcttt gcacgtttct   2880

gttttaactt tttccatatc aagtaaaatg gaaagcttca cggaaggcaa gtgaatgtat   2940

gtatggcttg cacatgagaa agtttccacg tgcagcttgt gatgatgtga tccccccgca   3000

ttaacgcgta acgcggtgca ttcttttttt gtactcttga ggtagtagca aatgtgaatg   3060

aagtttgtgc tcgttgtttg att                                           3083
```

<210> SEQ ID NO 8
<211> LENGTH: 877
<212> TYPE: PRT
<213> ORGANISM: Oryza sativa

<400> SEQUENCE: 8

```
Thr Arg Arg Met Ser Arg Val Met Thr Val Pro Gly Thr Leu Ser Glu
  1               5                  10                  15

Leu Asp Gly Glu Asp Asp Ser Glu His Ala Ala Thr Asn Ser Val Ala
             20                  25                  30

Ser Asp Val Pro Ser Ser Val Ala Gly Asp Arg Val Ile Val Val Ser
         35                  40                  45

Asn Gln Leu Pro Val Val Ala Arg Arg Arg Pro Asp Gly Arg Gly Trp
     50                  55                  60

Ser Phe Ser Trp Asp Asp Asp Ser Leu Leu Leu Gln Leu Arg Asp Gly
 65                  70                  75                  80

Ile Pro Asp Glu Met Glu Val Phe Phe Val Gly Ser Leu Arg Ala Glu
                 85                  90                  95

Ile Pro Val Ala Asp Gln Glu Glu Val Ser Gln Ala Leu Leu Asp Arg
            100                 105                 110

Phe Arg Cys Ala Pro Val Phe Leu Pro Asp Pro Leu Asn Glu Arg Phe
        115                 120                 125

Tyr His Arg Phe Cys Lys Arg His Leu Trp Pro Leu Phe His Tyr Met
    130                 135                 140

Leu Pro Phe Ser Ser Ser Ala Ser Pro Ser Pro Ser Ser Ser Ser Ser
145                 150                 155                 160

Ser Ser Ser Ser Pro Ser Ser Ser Ser Gly Ser Gly His Phe Asp Arg
                165                 170                 175

Gly Ala Trp Glu Ala Tyr Val Leu Ala Asn Lys Phe Phe Phe Glu Lys
            180                 185                 190

Val Val Glu Val Ile Asn Pro Glu Asp Asp Tyr Val Trp Val His Asp
        195                 200                 205

Tyr His Leu Met Ala Leu Pro Thr Phe Leu Arg Arg Arg Phe Asn Arg
    210                 215                 220

Leu Arg Ile Gly Phe Phe Leu His Ser Pro Phe Pro Ser Ser Glu Ile
225                 230                 235                 240

Tyr Arg Thr Leu Pro Val Arg Glu Glu Ile Leu Lys Ala Leu Leu Asn
                245                 250                 255

Cys Asp Leu Ile Gly Phe His Thr Phe Asp Tyr Ala Arg His Phe Leu
            260                 265                 270

Ser Cys Cys Ser Arg Met Leu Gly Ile Glu Tyr Gln Ser Lys Arg Gly
        275                 280                 285

Tyr Ile Gly Leu Asp Tyr Phe Gly Arg Thr Val Gly Ile Lys Ile Met
    290                 295                 300

Pro Val Gly Val His Met Gly Gln Leu Lys Thr Val Leu Ser Leu Pro
305                 310                 315                 320
```

-continued

```
Asp Arg Glu Trp Arg Val Ser Glu Leu Gln Gln Gln Phe Glu Gly Lys
                325                 330                 335

Thr Val Leu Leu Gly Val Asp Asp Met Asp Ile Phe Lys Gly Ile Asn
            340                 345                 350

Leu Lys Leu Leu Ala Phe Glu Asn Met Leu Arg Thr His Pro Lys Trp
        355                 360                 365

Gln Gly Arg Ala Val Leu Val Gln Ile Ala Asn Pro Ala Arg Gly Lys
    370                 375                 380

Gly Lys Asp Leu Glu Ala Ile Gln Ala Glu Ile His Glu Ser Cys Lys
385                 390                 395                 400

Arg Ile Asn Gly Glu Phe Gly Gln Ser Gly Tyr Ser Pro Val Val Phe
                405                 410                 415

Ile Asp Arg Asp Val Ser Ser Val Glu Lys Ile Ala Tyr Tyr Thr Ile
            420                 425                 430

Ala Glu Cys Val Val Val Thr Ala Val Arg Asp Gly Met Asn Leu Thr
        435                 440                 445

Pro Tyr Glu Tyr Ile Val Cys Arg Gln Gly Ser Asp Ser Thr Ser Glu
    450                 455                 460

Val Asn Gly Pro Lys Lys Ser Met Leu Val Val Ser Glu Phe Ile Gly
465                 470                 475                 480

Cys Ser Pro Ser Leu Ser Gly Ala Ile Arg Val Asn Pro Trp Asn Ile
                485                 490                 495

Glu Ala Thr Ala Glu Ala Leu Asn Glu Ala Ile Ser Met Ser Glu Gln
            500                 505                 510

Glu Lys His Leu Arg His Glu Lys His Tyr Arg Tyr Val Ser Thr His
        515                 520                 525

Asp Val Ala Tyr Trp Ser Lys Ser Phe Ile Gln Asp Leu Glu Arg Ala
    530                 535                 540

Cys Lys Asp His Phe Arg Arg Thr Cys Trp Gly Ile Gly Leu Gly Phe
545                 550                 555                 560

Gly Phe Arg Val Val Ala Leu Asp Pro His Phe Thr Lys Leu Asn Met
                565                 570                 575

Asp Ser Ile Val Met Ala Tyr Glu Arg Ser Glu Ser Arg Ala Ile Phe
            580                 585                 590

Leu Asp Tyr Asp Gly Thr Leu Val Pro Gln Thr Ser Ile Ser Arg Thr
        595                 600                 605

Pro Ser Ala Glu Val Leu Arg Ile Ile Asn Thr Leu Cys Ser Asp Arg
    610                 615                 620

Arg Asn Lys Val Phe Leu Val Ser Gly Arg Arg Arg Asp Lys Leu Gly
625                 630                 635                 640

Glu Trp Phe Ser Ser Cys Pro Asp Leu Gly Ile Ala Ala Glu His Gly
                645                 650                 655

Tyr Phe Leu Arg Trp Thr Arg Asp Glu Glu Trp Gln Thr Cys Thr Gln
            660                 665                 670

Thr Ser Asp Phe Gly Trp Met Glu Met Ala Lys Pro Val Met Asn Leu
        675                 680                 685

Tyr Thr Glu Ala Thr Asp Gly Ser Tyr Ile Asp Pro Lys Glu Ser Ala
    690                 695                 700

Leu Val Trp His His Gln Asp Ala Asp Pro Gly Phe Gly Ser Ser Gln
705                 710                 715                 720

Ala Lys Glu Leu Leu Asp His Leu Glu Ser Val Leu Ala Asn Glu Pro
                725                 730                 735
```

-continued

```
Val Ser Val Lys Ser Gly Gln Phe Ile Val Glu Val Lys Pro Gln Gly
            740                 745                 750

Val Ser Lys Gly Val Val Ala Glu Lys Ile Leu Val Ser Met Lys Glu
        755                 760                 765

Arg Gly Lys Gln Ala Asp Phe Val Leu Cys Ile Gly Asp Asp Arg Ser
    770                 775                 780

Asp Glu Asp Met Phe Glu Asn Ile Ala Asp Thr Ile Lys Lys Gly Met
785                 790                 795                 800

Val Ala Thr Asn Thr Ser Leu Phe Ala Cys Thr Val Gly Gln Lys Pro
                805                 810                 815

Ser Lys Ala Lys Phe Tyr Leu Asp Asp Thr Phe Glu Val Val Thr Met
            820                 825                 830

Leu Ser Ala Leu Ala Asp Ala Thr Glu Pro Glu Pro Glu Thr Asp Leu
        835                 840                 845

Thr Asp Glu Phe Asp Glu Leu Ala Val Ser Val Ser Ser Val Asp Ile
    850                 855                 860

Asp Asp Glu Gln Thr Pro Ser Asp Lys Leu Ile Gly Gly
865                 870                 875


<210> SEQ ID NO 9
<211> LENGTH: 3157
<212> TYPE: DNA
<213> ORGANISM: Oryza sativa

<400> SEQUENCE: 9

gcacgagcgc tgtcggagct ggacgacgag gacgacgagc cggcggcgac gagcagcgtc      60

gcctccgacg tgccctcgtc ggcggcgtgc gagcgcctca tcgtcgtggc gaaccagctc     120

cccgtggtgg cgcggcggag gccgggcgcc gcggcggggg ggtgggcgtt ctcgtgggac     180

gacgactcgc tcctcctccg cctccgcgac ggcgtccccg acgagatgga ggtgctcttc     240

atcggcacgc tccgcgccga cgtgcccgcc tgcgagcagg acgaggtgtc gcagagcctc     300

atcgatggat tcggatgcgc acccgtgttc ctccccgcgg ggctctacga ccgattctac     360

cagcacttct gcaagggtta cctatggccg ctgttccact acatgctccc cttcgcctcc     420

gccttgccgg cggccgcatc cggcgatggc cggtttgacc gcggcgcgtg ggaggcctac     480

gtgctcgcca acaaatactt cttcgagaag gtggtcgagg tcatcaaccc ggaggacgac     540

tacgtttggg tccacgatta ccacctcatg gcgctgccca ccttcctccg ccgccgcttc     600

aatcgcctcc gcatcgggtt cttcctccac agcccctttc cctcatcgga gatctaccgc     660

tcgctgcccg tccgagagga gatcctaaga acgctgctta attgcgatct cattggattc     720

cacacattcg attatgcgag gcacttccta tcttgctgta gtaggatgct ggggatagag     780

taccagtcaa agcgtggata cattggattg gattactttg gccgcactgt tggaatcaag     840

atcatgccag tgggaatcca tatgggtcaa ttgcaatcag tgttgcgatt gtccgagaaa     900

gaaaagaagg ttgctgagct gcggcagcaa ttcgagggca agtccgtgtt acttggtgtg     960

gatgatatgg atatcttcaa gggaatcaac ttaaaacttc ttgcgtttga gaatatgctg    1020

aggacgcatc ccaagtggaa gggaagagct gtgttggtgc agattgcaaa cccagcacga    1080

gggaagggaa aggatctgga ggctgtccag gctgagattc gggagagttg tgatagaatt    1140

aacaaggagt ttggccagtc aggttacagt ccagtgattt tcattgacca gagcgtgcca    1200

agtgcggtga ggcttgcata ttatacggtt gctgagtgtg ttgtggtgac ggctgtgagg    1260

gatgggatga atttgacccc atatgaatac attgtctgcc gggaggggat acctggctct    1320
```

-continued

```
gagtgtgcac cagaggtgag tggaccaaag aagagcatgt tggttgtgtc ggagtttatt   1380
ggttgctcac cttcactgag tggagccatt cgtgttaacc cgtggaatat cgaggcaact   1440
gcagaggcac tgaatgaggc catctcaatg tcagagcgtg aaaagcagct gaggcacgaa   1500
aaacattacc gttatgtcag cacccatgat gttgcatatt ggtctaagag ctttgtacag   1560
gacctggaga gggcttgcaa ggatcacttt aggaaaccat gctggggcat tggattggga   1620
tttggcttca gggtggtagc cctagaccca catttcacaa agcttaattt cgaatcaatt   1680
ataatgtcct atgagagatc aaagagtagg gctatatttc tcgactatga tggcacattg   1740
gtgccacagg cttcgctcaa caagaatcca agtgaagaat tactgaggat cattaatacc   1800
ctatgcgcag atagaaataa caccgtgttc attgtcagcg ggagaagcaa ggatgacttg   1860
agcaaaaagc ttatctcatg tccaaagcta ggcattgccg cagagcatgg ctacttctta   1920
aggtggacta gagatgaaga atggcaaacc actgcacaga cctcagattt tggatggatg   1980
caaatggcga agccagtgat ggatctttat actgaatcaa ctgacggatc caccattgag   2040
actaaagaaa ctgcactggt gtggcaccat caggatgctg accaaggttt tggctcttcc   2100
caggcaaagg aaatgcttga tcacttggaa agtgtattag caaatgaacc agtctcagtc   2160
aagagtggcc aattcattgt tgaagtcaaa cctcagggtg ttaccaaagg gctcatagct   2220
gagaaagtac tcacatcaat gaaggagaag ggcaactggc cagattttgt attatgcatt   2280
ggtgatgaca ggtcagatga ggatatgttt gaaaatattg ccgatgtcat gaaaaggagc   2340
attgttgcac caaaaactcc actgtttgca tgtactgtgg gccagaagcc aagcaaagct   2400
aggttttacc tggatgatac atttgaagtc gtcaccatgt tgagttcact ggcggatgct   2460
tcagaaccag accttatggc agacttggaa gatgacttgg ccacatcagt ctcatcaata   2520
gaaataagtg acagagtggt atcttttagt aatttaagga cagaaggatc ttagtctggt   2580
gtttctgcgt tgcttttctc gccgaaaaag ttctgttgga actgagtgag ggagtgttaa   2640
gcaagatgaa acactgcaag attaaagatg ctacagggca aggaagtcga attcttgggt   2700
tcatgattca ttttggtgaa gatgagggta agggattaaa acatgtagct gcaaatattc   2760
tgaagtccgg aaagagatta cagtttgagt agctcccaaa tagcctcatt atgcgttttg   2820
ttacggcggc atttactacc agtcgctgct acgaagattc ttatgttcat agctgacctg   2880
ccatgttctt tccatttgaa tacttatccc aaggctaagt aggaagcatc ggcgtggcag   2940
aagtgcatcg gtgcaatatg gggaatatg agggtaaatc ttgtgacagg ttaactgcag   3000
cttgtgattt cttgcttgtt aacctggtta acagaaatcg tctagtaggg aaaaaactag   3060
tgatgctttt cgtttacttg taatgttgtg gcaatgtgga ggatgacatt tgattcattg   3120
tttgacagca ttatctgtat catccttata tgtagct                            3157
```

<210> SEQ ID NO 10
<211> LENGTH: 857
<212> TYPE: PRT
<213> ORGANISM: Oryza sativa

<400> SEQUENCE: 10

```
Ala Arg Ala Leu Ser Glu Leu Asp Asp Glu Asp Asp Glu Pro Ala Ala
  1               5                  10                  15

Thr Ser Ser Val Ala Ser Asp Val Pro Ser Ser Ala Ala Cys Glu Arg
             20                  25                  30

Leu Ile Val Val Ala Asn Gln Leu Pro Val Val Ala Arg Arg Arg Pro
         35                  40                  45
```

-continued

```
Gly Ala Ala Ala Gly Gly Trp Ala Phe Ser Trp Asp Asp Asp Ser Leu
    50                  55                  60

Leu Leu Arg Leu Arg Asp Gly Val Pro Asp Glu Met Glu Val Leu Phe
65                  70                  75                  80

Ile Gly Thr Leu Arg Ala Asp Val Pro Ala Cys Glu Gln Asp Glu Val
                85                  90                  95

Ser Gln Ser Leu Ile Asp Gly Phe Gly Cys Ala Pro Val Phe Leu Pro
            100                 105                 110

Ala Gly Leu Tyr Asp Arg Phe Tyr Gln His Phe Cys Lys Gly Tyr Leu
        115                 120                 125

Trp Pro Leu Phe His Tyr Met Leu Pro Phe Ala Ser Ala Leu Pro Ala
    130                 135                 140

Ala Ala Ser Gly Asp Gly Arg Phe Asp Arg Gly Ala Trp Glu Ala Tyr
145                 150                 155                 160

Val Leu Ala Asn Lys Tyr Phe Phe Glu Lys Val Val Glu Val Ile Asn
                165                 170                 175

Pro Glu Asp Asp Tyr Val Trp Val His Asp Tyr His Leu Met Ala Leu
            180                 185                 190

Pro Thr Phe Leu Arg Arg Arg Phe Asn Arg Leu Arg Ile Gly Phe Phe
        195                 200                 205

Leu His Ser Pro Phe Pro Ser Ser Glu Ile Tyr Arg Ser Leu Pro Val
    210                 215                 220

Arg Glu Glu Ile Leu Arg Thr Leu Leu Asn Cys Asp Leu Ile Gly Phe
225                 230                 235                 240

His Thr Phe Asp Tyr Ala Arg His Phe Leu Ser Cys Cys Ser Arg Met
                245                 250                 255

Leu Gly Ile Glu Tyr Gln Ser Lys Arg Gly Tyr Ile Gly Leu Asp Tyr
            260                 265                 270

Phe Gly Arg Thr Val Gly Ile Lys Ile Met Pro Val Gly Ile His Met
        275                 280                 285

Gly Gln Leu Gln Ser Val Leu Arg Leu Ser Glu Lys Glu Lys Lys Val
    290                 295                 300

Ala Glu Leu Arg Gln Gln Phe Glu Gly Lys Ser Val Leu Leu Gly Val
305                 310                 315                 320

Asp Asp Met Asp Ile Phe Lys Gly Ile Asn Leu Lys Leu Leu Ala Phe
                325                 330                 335

Glu Asn Met Leu Arg Thr His Pro Lys Trp Lys Gly Arg Ala Val Leu
            340                 345                 350

Val Gln Ile Ala Asn Pro Ala Arg Gly Lys Gly Lys Asp Leu Glu Ala
        355                 360                 365

Val Gln Ala Glu Ile Arg Glu Ser Cys Asp Arg Ile Asn Lys Glu Phe
    370                 375                 380

Gly Gln Ser Gly Tyr Ser Pro Val Ile Phe Ile Asp Gln Ser Val Pro
385                 390                 395                 400

Ser Ala Val Arg Leu Ala Tyr Tyr Thr Val Ala Glu Cys Val Val Val
                405                 410                 415

Thr Ala Val Arg Asp Gly Met Asn Leu Thr Pro Tyr Glu Tyr Ile Val
            420                 425                 430

Cys Arg Glu Gly Ile Pro Gly Ser Glu Cys Ala Pro Glu Val Ser Gly
        435                 440                 445

Pro Lys Lys Ser Met Leu Val Val Ser Glu Phe Ile Gly Cys Ser Pro
    450                 455                 460

Ser Leu Ser Gly Ala Ile Arg Val Asn Pro Trp Asn Ile Glu Ala Thr
```

-continued

```
465                 470                 475                 480

Ala Glu Ala Leu Asn Glu Ala Ile Ser Met Ser Glu Arg Glu Lys Gln
                485                 490                 495

Leu Arg His Glu Lys His Tyr Arg Tyr Val Ser Thr His Asp Val Ala
            500                 505                 510

Tyr Trp Ser Lys Ser Phe Val Gln Asp Leu Glu Arg Ala Cys Lys Asp
        515                 520                 525

His Phe Arg Lys Pro Cys Trp Gly Ile Gly Leu Gly Phe Gly Phe Arg
    530                 535                 540

Val Val Ala Leu Asp Pro His Phe Thr Lys Leu Asn Phe Glu Ser Ile
545                 550                 555                 560

Ile Met Ser Tyr Glu Arg Ser Lys Ser Arg Ala Ile Phe Leu Asp Tyr
                565                 570                 575

Asp Gly Thr Leu Val Pro Gln Ala Ser Leu Asn Lys Asn Pro Ser Glu
            580                 585                 590

Glu Leu Leu Arg Ile Ile Asn Thr Leu Cys Ala Asp Arg Asn Asn Thr
        595                 600                 605

Val Phe Ile Val Ser Gly Arg Ser Lys Asp Asp Leu Ser Lys Lys Leu
    610                 615                 620

Ile Ser Cys Pro Lys Leu Gly Ile Ala Ala Glu His Gly Tyr Phe Leu
625                 630                 635                 640

Arg Trp Thr Arg Asp Glu Glu Trp Gln Thr Thr Ala Gln Thr Ser Asp
                645                 650                 655

Phe Gly Trp Met Gln Met Ala Lys Pro Val Met Asp Leu Tyr Thr Glu
            660                 665                 670

Ser Thr Asp Gly Ser Thr Ile Glu Thr Lys Glu Thr Ala Leu Val Trp
        675                 680                 685

His His Gln Asp Ala Asp Gln Gly Phe Gly Ser Ser Gln Ala Lys Glu
    690                 695                 700

Met Leu Asp His Leu Glu Ser Val Leu Ala Asn Glu Pro Val Ser Val
705                 710                 715                 720

Lys Ser Gly Gln Phe Ile Val Glu Val Lys Pro Gln Gly Val Thr Lys
                725                 730                 735

Gly Leu Ile Ala Glu Lys Val Leu Thr Ser Met Lys Glu Lys Gly Gln
            740                 745                 750

Leu Ala Asp Phe Val Leu Cys Ile Gly Asp Asp Arg Ser Asp Glu Asp
        755                 760                 765

Met Phe Glu Asn Ile Ala Asp Val Met Lys Arg Ser Ile Val Ala Pro
    770                 775                 780

Lys Thr Pro Leu Phe Ala Cys Thr Val Gly Gln Lys Pro Ser Lys Ala
785                 790                 795                 800

Arg Phe Tyr Leu Asp Asp Thr Phe Glu Val Val Thr Met Leu Ser Ser
                805                 810                 815

Leu Ala Asp Ala Ser Glu Pro Asp Leu Met Ala Asp Leu Glu Asp Asp
            820                 825                 830

Leu Ala Thr Ser Val Ser Ser Ile Glu Ile Ser Asp Arg Val Val Ser
        835                 840                 845

Phe Ser Asn Leu Arg Thr Glu Gly Ser
    850                 855
```

<210> SEQ ID NO 11
<211> LENGTH: 2538
<212> TYPE: DNA
<213> ORGANISM: Glycine max

<400> SEQUENCE: 11

```
gcacgaggct gaacaggatg atgtatcaca gtatttattg gataaattca aatgtgtgcc     60
gactttttta cccgctgacg ttttggcaaa attttatgac ggcttctgta aacggcagtt    120
atggccactt tttcattata tgttaccatt ttcaacagat aaaagccacc gatttgatcg    180
ttctttgtgg gaagcttacg tgctggcaaa caagcttttt tttcagaagg tagttgaaat    240
aataaaccca gaggatgatt acatttggat tcatgattat catttgatgg tgctgccaac    300
ttttataaga aggcgtttta acagggttaa aatgggattt ttcctgcata gcccctttcc    360
atcatcagag atatacagga ctcttccggt cagggaagag atactgaaag ctttactaaa    420
ctctgatatc atcggattcc atacctttga ctatgctcgt catttccttt cctgttgcag    480
tcgtatgttg ggtctggagt atcagtcaaa gaggggttat ttaggattgg agtattatgg    540
aaggacaatc agtattaaga ttatgcctgt tgggattcac atgggtcgaa ttgagtcagt    600
tatgagaatg gcagatgagg aatgcaaggt aagggagctc aaacagaaat ttgaaggaaa    660
aaccatcttg cttggtattg atgatatgga catttttaaa ggcataaatt tgaagatttt    720
ggctatggag cagatgctca gacagcatcc caaatggcaa ggaagagctg ttctggtcca    780
gatagttaat cctgctagag gtaaagggat acatctggag gagatacatg ctgaaataca    840
agaaagctgc aacaggatca acagagtgtt tgggagacct ggttatgaac ctattgtttt    900
tattgataga gcagttccta ttgctgaaaa agttgcttat tactgcattg ctgagtgtgt    960
tattgtcaca gctgtaaggg atggaatgaa cctaactcct tatgagtata ttgcatgtag   1020
acagggaata tctggttctg aatcatgttc caatgtcaat gaccctaaga agagtatgct   1080
agtaatatca gaatttattg ggtgttctcc atcacttagt ggggcaatcc gtgtcaatcc   1140
atggaatgtt gaagcaactt cagaggcaat gaatgaggcc atctcaactg gtgatggaga   1200
gaaacagttg cggcacgaga agcattaccg ttatgtcagc actcatgatg tggcttactg   1260
gtcacgtagt ttcttgcaag acatggagcg ggcttgcaca gaccttctaa ggaaaagatg   1320
ttggggaata ggtcttagct ttggatttag agttgtggca cttgacccta attttaaaaa   1380
gctctcaatc gatgctatgg tttcagctta caagagggca aagaataggg ccattttgtt   1440
ggactatgat ggtactgtga tgccacagaa ctccattaat aagagtccaa gcaaggaggt   1500
cttgtctatt ttggaatcac ttagtgaaga ccccaaaaat gttgttttca ttgttagtgg   1560
acgggggagg aatagcttaa gtgactggtt taattcctgt gaaaaacttg gaattgctgc   1620
agaacatggg tacttcttga gatggtccca caatcgagaa tgggaaaatt gtggtaagag   1680
ctccgacttt ggatggatgc agattgctga acctgtaatg aaactctata cagaggcgac   1740
tgatggttcc tctattgaaa gaaaagaaag tgctttggtc tggcaatacc gtgatgcaga   1800
ccttggtttt ggatctgctc aggctaagga aatgttagat catctagaaa gtgttttggc   1860
caatgagcct gttgctgtga agagtggcca gtttattgtt gaagtaaaac cccaggatgt   1920
gagcaaaggc ttagtcgccg agaagatatt ttcgtcaatg gacgggaagg gcaaacaggc   1980
cgactttgtg ttgtgtgttg gtgatgacag atcagatgag gacatgtttg agatagttag   2040
tagtgccatc tcaaggaata ttcttgccac caatgcttct gtgtttgctt gcacggttgg   2100
acaaaaacca agcaaagcaa agtattattt ggatgataca actgaggtaa caagcatgtt   2160
ggaatctttg gctgaagaat cagatgcttc accctacata gaagaaactg gagattcctc   2220
tcggaggcaa gtgtgagttg aggttgaggt ttctcttatt ttaggtgatg attttttttt   2280
```

-continued

```
ttaattggga tgtaatattc gtggtgatat ttggggcgtt tgcagagtat gttttcataa   2340

tattttttt tctttttgg tttttcttct attatatatt acatatattt ttgggagaat   2400

cccgtcatta ttttctgttg cagtcattga tagttttatt attttagttg tggtgtagca   2460

gataacaagg atgctaattt tgattttttt atattctata acaaaggaag aaaagagtga   2520

aagctcttct tgcttggc                                                  2538


<210> SEQ ID NO 12
<211> LENGTH: 744
<212> TYPE: PRT
<213> ORGANISM: Glycine max

<400> SEQUENCE: 12

His Glu Ala Glu Gln Asp Asp Val Ser Gln Tyr Leu Leu Asp Lys Phe
1               5                   10                  15

Lys Cys Val Pro Thr Phe Leu Pro Ala Asp Val Leu Ala Lys Phe Tyr
            20                  25                  30

Asp Gly Phe Cys Lys Arg Gln Leu Trp Pro Leu Phe His Tyr Met Leu
        35                  40                  45

Pro Phe Ser Thr Asp Lys Ser His Arg Phe Asp Arg Ser Leu Trp Glu
    50                  55                  60

Ala Tyr Val Leu Ala Asn Lys Leu Phe Phe Gln Lys Val Val Glu Ile
65                  70                  75                  80

Ile Asn Pro Glu Asp Asp Tyr Ile Trp Ile His Asp Tyr His Leu Met
                85                  90                  95

Val Leu Pro Thr Phe Ile Arg Arg Arg Phe Asn Arg Val Lys Met Gly
            100                 105                 110

Phe Phe Leu His Ser Pro Phe Pro Ser Ser Glu Ile Tyr Arg Thr Leu
        115                 120                 125

Pro Val Arg Glu Glu Ile Leu Lys Ala Leu Leu Asn Ser Asp Ile Ile
    130                 135                 140

Gly Phe His Thr Phe Asp Tyr Ala Arg His Phe Leu Ser Cys Cys Ser
145                 150                 155                 160

Arg Met Leu Gly Leu Glu Tyr Gln Ser Lys Arg Gly Tyr Leu Gly Leu
                165                 170                 175

Glu Tyr Tyr Gly Arg Thr Ile Ser Ile Lys Ile Met Pro Val Gly Ile
            180                 185                 190

His Met Gly Arg Ile Glu Ser Val Met Arg Met Ala Asp Glu Glu Cys
        195                 200                 205

Lys Val Arg Glu Leu Lys Gln Lys Phe Glu Gly Lys Thr Ile Leu Leu
    210                 215                 220

Gly Ile Asp Asp Met Asp Ile Phe Lys Gly Ile Asn Leu Lys Ile Leu
225                 230                 235                 240

Ala Met Glu Gln Met Leu Arg Gln His Pro Lys Trp Gln Gly Arg Ala
                245                 250                 255

Val Leu Val Gln Ile Val Asn Pro Ala Arg Gly Lys Gly Ile His Leu
            260                 265                 270

Glu Glu Ile His Ala Glu Ile Gln Glu Ser Cys Asn Arg Ile Asn Arg
        275                 280                 285

Val Phe Gly Arg Pro Gly Tyr Glu Pro Ile Val Phe Ile Asp Arg Ala
    290                 295                 300

Val Pro Ile Ala Glu Lys Val Ala Tyr Tyr Cys Ile Ala Glu Cys Val
305                 310                 315                 320

Ile Val Thr Ala Val Arg Asp Gly Met Asn Leu Thr Pro Tyr Glu Tyr
```

-continued

```
                325                 330                 335

Ile Ala Cys Arg Gln Gly Ile Ser Gly Ser Glu Ser Cys Ser Asn Val
            340                 345                 350

Asn Asp Pro Lys Lys Ser Met Leu Val Ile Ser Glu Phe Ile Gly Cys
        355                 360                 365

Ser Pro Ser Leu Ser Gly Ala Ile Arg Val Asn Pro Trp Asn Val Glu
    370                 375                 380

Ala Thr Ser Glu Ala Met Asn Glu Ala Ile Ser Thr Gly Asp Gly Glu
385                 390                 395                 400

Lys Gln Leu Arg His Glu Lys His Tyr Arg Tyr Val Ser Thr His Asp
                405                 410                 415

Val Ala Tyr Trp Ser Arg Ser Phe Leu Gln Asp Met Glu Arg Ala Cys
            420                 425                 430

Thr Asp Leu Leu Arg Lys Arg Cys Trp Gly Ile Gly Leu Ser Phe Gly
        435                 440                 445

Phe Arg Val Val Ala Leu Asp Pro Asn Phe Lys Lys Leu Ser Ile Asp
    450                 455                 460

Ala Met Val Ser Ala Tyr Lys Arg Ala Lys Asn Arg Ala Ile Leu Leu
465                 470                 475                 480

Asp Tyr Asp Gly Thr Val Met Pro Gln Asn Ser Ile Asn Lys Ser Pro
                485                 490                 495

Ser Lys Glu Val Leu Ser Ile Leu Glu Ser Leu Ser Glu Asp Pro Lys
            500                 505                 510

Asn Val Val Phe Ile Val Ser Gly Arg Gly Arg Asn Ser Leu Ser Asp
        515                 520                 525

Trp Phe Asn Ser Cys Glu Lys Leu Gly Ile Ala Ala Glu His Gly Tyr
    530                 535                 540

Phe Leu Arg Trp Ser His Asn Arg Glu Trp Glu Asn Cys Gly Lys Ser
545                 550                 555                 560

Ser Asp Phe Gly Trp Met Gln Ile Ala Glu Pro Val Met Lys Leu Tyr
                565                 570                 575

Thr Glu Ala Thr Asp Gly Ser Ser Ile Glu Arg Lys Glu Ser Ala Leu
            580                 585                 590

Val Trp Gln Tyr Arg Asp Ala Asp Leu Gly Phe Gly Ser Ala Gln Ala
        595                 600                 605

Lys Glu Met Leu Asp His Leu Glu Ser Val Leu Ala Asn Glu Pro Val
    610                 615                 620

Ala Val Lys Ser Gly Gln Phe Ile Val Glu Val Lys Pro Gln Asp Val
625                 630                 635                 640

Ser Lys Gly Leu Val Ala Glu Lys Ile Phe Ser Ser Met Asp Gly Lys
                645                 650                 655

Gly Lys Gln Ala Asp Phe Val Leu Cys Val Gly Asp Asp Arg Ser Asp
            660                 665                 670

Glu Asp Met Phe Glu Ile Val Ser Ser Ala Ile Ser Arg Asn Ile Leu
        675                 680                 685

Ala Thr Asn Ala Ser Val Phe Ala Cys Thr Val Gly Gln Lys Pro Ser
    690                 695                 700

Lys Ala Lys Tyr Tyr Leu Asp Asp Thr Thr Glu Val Thr Ser Met Leu
705                 710                 715                 720

Glu Ser Leu Ala Glu Glu Ser Asp Ala Ser Pro Tyr Ile Glu Glu Thr
                725                 730                 735

Gly Asp Ser Ser Arg Arg Gln Val
            740
```

<210> SEQ ID NO 13
<211> LENGTH: 2511
<212> TYPE: DNA
<213> ORGANISM: Triticum aestivum

<400> SEQUENCE: 13

```
gcacgagcaa gcactacatg tggccgctcc tccactacct gctcccgctc acgccctcca     60

cgctcggggg gctgcccttc gaccgcgcgc tctaccactc cttcctctcc gccaaccgcg    120

ccttcgccga ccgcctcacc gaggtgctcg cccccgacga cgacttcgtc tggatccagg    180

actaccacct cctcgccctc cccaccttcc tccgcaagcg cttcccgcgc gccagggtcg    240

gattcttcct ccactcgccc ttcccctcct ccgagatctt ccgcaccatc cccgtccgcg    300

acgacctgct ccgcgccctc ctcaacgccg acctcgtcgg cttccacacc ttcgactacg    360

cgcgccactt cctttcggcc tgctcccgcc tcctcggcct cgactaccag tccaagcgcg    420

gatacatcgg catcgagtac tacggccgca ccgtcaccgt caagattctg cccgtcggca    480

tcgacatggg ccagctccgg tcggtcgtgt cggcgccgga gacggcggac gtggtgcgcc    540

aggtcgccga cgcctacaag gggaggcgcc tcatgctcgg cgtggacgac gtcgacctct    600

tcaaggggat cgggctcaag ttcctgggga tggagcagct gctggtggag aaccccgagc    660

tccggggcaa ggccgtgctc gtgcaaatca ccaatccggc gcgcagcgag ggccgggacg    720

tgcaggaggt gcaggatgag gccagagcca tcagcgcccg tgtcaacgag cggttcggca    780

cccccgggta cacccccatc gtgatgatca gccgcccggt gtcggagcac gagaaggcgg    840

cttactacgc cgccgccgag tgctgcgtgg tgagcgccgt ccgcgacggg ctcaaccgga    900

ttccgtacat ctacacggtg tgccggcagg agagcaccgc cctgggcgac gcccccaagc    960

gaagcgtcat cgtgctgtcc gagttcgtgg gatgctcccc gtcgctcagc ggggcgatcc   1020

cgggtgaacc catggagcgt ggagtccgtg gcagaggcca tgagctcggc attgaggatg   1080

tccgacggcg agcagcggct gcgccacgag aagcattaca agtatgtgag cacccatgat   1140

gtggcctact gggcgcggtc cttcgaccag gacctgcagc gggcctgcaa ggaccatttc   1200

tcgtggcggc attgggggat tgggttcggg atgagcttca aggtggtggc gcttggccca   1260

aatttcaggc ggctctccgt cgagcacatt gtgccgtcgt tcaggaagac ggagaaccgg   1320

ctgattctcc tggactacga tggcacggtg atgccggaga gttccatcga caaggcgccg   1380

agcagtgagg tcatctctgt cttgaatcgg ctgtgcgaag atccgaagaa cagggtgttc   1440

atcgtgagcg gtcgggggaa ggatgagctg agcaagtggt tcgcgccatg tgagaagctg   1500

ggaattgctg cagagcatgg ctacttcact aggtggagca aggaatcgcc atgggagacc   1560

tgcgggctgg tggcagactt cgattggaag aagacggccg agccggtgat gagactgtac   1620

acagaggcca ccgatggatc gtacatcgag cacaaggaga gcgcgctggt gtggcaccac   1680

gacgaggcgg atcctgactt cggttcatgc caggcgaagg agctgctcga ccatctcgag   1740

agcgtgctcg ccaacgagcc agtcgtcgtg aagaggggcc agcacatcgt ggaggttaac   1800

ccccagggca tcagcaaggg cgtggtggtg gagagcctcc tgtcgtccat ggtgcgcggc   1860

ggcaaggcgc ccgacttcgt gctctgcatc ggggacgacc ggtccgacga ggacatgttc   1920

gagagcatcg tgtgcccggc caacggcagc gtgaagctcc cggcgacgag cgaggtgttc   1980

gcgtgcaccg tggggaagaa gccgagcatg gccaagtact acctggacga cacggtggac   2040

gtgatcaaga tgctgcaggg gctcgcgaac gcgccgtcgc agcagcggcc gtggcccgtg   2100
```

-continued

```
cagctccggg tcaccttcga ggaaggaaac ggagtatgaa caaaccaagg aggagatgtc   2160

aataaccagt gaaaaaagaa ggacgacggt ggtgatgatg atgatgatga ttcagcgagt   2220

cggttggtgt ggttttagga ttagctgcag ttacaggata aacaggtttc tttcttcttc   2280

tttcttctgc ttctttttct ggtttacgtt tccgacctct tcctctcgcg cacgcatata   2340

catatgcccg cccgccccca tacattgagc gtgagaggga gaggtttgtt ccttcgggtc   2400

acattgtata tgtagttgac gatgacgatg aagatgaaat caatcagagc aagaaaaatg   2460

attctttcaa aaaaaaaaaa aaaaaaaaaa aaaaaaaaaa aaaaaaaaaa a            2511


<210> SEQ ID NO 14
<211> LENGTH: 378
<212> TYPE: PRT
<213> ORGANISM: Triticum aestivum

<400> SEQUENCE: 14

Thr Ser Lys His Tyr Met Trp Pro Leu Leu His Tyr Leu Leu Pro Leu
  1               5                  10                  15

Thr Pro Ser Thr Leu Gly Gly Leu Pro Phe Asp Arg Ala Leu Tyr His
             20                  25                  30

Ser Phe Leu Ser Ala Asn Arg Ala Phe Ala Asp Arg Leu Thr Glu Val
         35                  40                  45

Leu Ala Pro Asp Asp Asp Phe Val Trp Ile Gln Asp Tyr His Leu Leu
     50                  55                  60

Ala Leu Pro Thr Phe Leu Arg Lys Arg Phe Pro Arg Ala Arg Val Gly
 65                  70                  75                  80

Phe Phe Leu His Ser Pro Phe Pro Ser Ser Glu Ile Phe Arg Thr Ile
                 85                  90                  95

Pro Val Arg Asp Asp Leu Leu Arg Ala Leu Leu Asn Ala Asp Leu Val
            100                 105                 110

Gly Phe His Thr Phe Asp Tyr Ala Arg His Phe Leu Ser Ala Cys Ser
        115                 120                 125

Arg Leu Leu Gly Leu Asp Tyr Gln Ser Lys Arg Gly Tyr Ile Gly Ile
    130                 135                 140

Glu Tyr Tyr Gly Arg Thr Val Thr Val Lys Ile Leu Pro Val Gly Ile
145                 150                 155                 160

Asp Met Gly Gln Leu Arg Ser Val Val Ser Ala Pro Glu Thr Ala Asp
                165                 170                 175

Val Val Arg Gln Val Ala Asp Ala Tyr Lys Gly Arg Arg Leu Met Leu
            180                 185                 190

Gly Val Asp Asp Val Asp Leu Phe Lys Gly Ile Gly Leu Lys Phe Leu
        195                 200                 205

Gly Met Glu Gln Leu Leu Val Glu Asn Pro Glu Leu Arg Gly Lys Ala
    210                 215                 220

Val Leu Val Gln Ile Thr Asn Pro Ala Arg Ser Glu Gly Arg Asp Val
225                 230                 235                 240

Gln Glu Val Gln Asp Glu Ala Arg Ala Ile Ser Ala Arg Val Asn Glu
                245                 250                 255

Arg Phe Gly Thr Pro Gly Tyr Thr Pro Ile Val Met Ile Ser Arg Pro
            260                 265                 270

Val Ser Glu His Glu Lys Ala Ala Tyr Tyr Ala Ala Ala Glu Cys Cys
        275                 280                 285

Val Val Ser Ala Val Arg Asp Gly Leu Asn Arg Ile Pro Tyr Ile Tyr
    290                 295                 300
```

-continued

```
Thr Val Cys Arg Gln Glu Ser Thr Ala Leu Gly Asp Ala Pro Lys Arg
305                 310                 315                 320

Ser Val Ile Val Leu Ser Glu Phe Val Gly Cys Ser Pro Ser Leu Ser
                325                 330                 335

Gly Ala Ile Pro Gly Glu Pro Met Glu Arg Gly Val Arg Gly Arg Gly
            340                 345                 350

His Glu Leu Gly Ile Glu Asp Val Arg Arg Arg Ala Ala Ala Ala Pro
        355                 360                 365

Arg Glu Ala Leu Gln Val Cys Glu His Pro
    370                 375


<210> SEQ ID NO 15
<211> LENGTH: 1613
<212> TYPE: DNA
<213> ORGANISM: Zea mays
<220> FEATURE:
<221> NAME/KEY: CDS
<222> LOCATION: (232)..(1338)
<223> OTHER INFORMATION:

<400> SEQUENCE: 15

ctctctcttc tctctctctc tctacggatt gcctcacacg catctcgcgt gcaattcaag      60

ttctcaggta ctccgccgtt gatgaactgc ctccacacct gcggcgacaa gaagacgctg     120

aagaagtggt ttttcatcga caagacagta ggctaaatcc agtcccagag aacaaattga     180

agcaccactc cccaccgcac agcagcacag ctcttctctt caccgatccc g atg gat      237
                                                         Met Asp
                                                         1

atg ggc agc ggc tcg tca cct gtc atc acc gat ccg ata tcg ata agc      285
Met Gly Ser Gly Ser Ser Pro Val Ile Thr Asp Pro Ile Ser Ile Ser
        5                   10                  15

cca ccg ctg ctg gga ggc ttg acg tcg aac ctg atg ccg ttc tcg gtc      333
Pro Pro Leu Leu Gly Gly Leu Thr Ser Asn Leu Met Pro Phe Ser Val
    20                  25                  30

atg tcc gga ggc tgc tcc tcc agt cct agc atg agc gcc agc agc agg      381
Met Ser Gly Gly Cys Ser Ser Ser Pro Ser Met Ser Ala Ser Ser Arg
35                  40                  45                  50

cgt aaa atc gag gag gtc ctt gtc aat ggc ctg cta gac gcg atg aaa      429
Arg Lys Ile Glu Glu Val Leu Val Asn Gly Leu Leu Asp Ala Met Lys
                55                  60                  65

tcg tcg tcg cct cgc aag aag cac aac ctc gcc ttc gga cag gat aat      477
Ser Ser Ser Pro Arg Lys Lys His Asn Leu Ala Phe Gly Gln Asp Asn
            70                  75                  80

tcg ccc gac gaa gat cct gct tac act gca tgg ctg tca aaa tgc cct      525
Ser Pro Asp Glu Asp Pro Ala Tyr Thr Ala Trp Leu Ser Lys Cys Pro
        85                  90                  95

tct gcg ctg gcc tcc ttc aag cag ata gta gcc aac gca cag ggc agg      573
Ser Ala Leu Ala Ser Phe Lys Gln Ile Val Ala Asn Ala Gln Gly Arg
    100                 105                 110

agg atc gct gtg ttc ttg gat tac gac ggc acc ctg tcg ccg atc gtc      621
Arg Ile Ala Val Phe Leu Asp Tyr Asp Gly Thr Leu Ser Pro Ile Val
115                 120                 125                 130

gac gat ccc gac aaa gcg ttc atg tcc cct gtg atg aga gct gct gtt      669
Asp Asp Pro Asp Lys Ala Phe Met Ser Pro Val Met Arg Ala Ala Val
                135                 140                 145

aga aat gtc gcg aag tac ttc cct acc gcg att gtc agc gga agg tcc      717
Arg Asn Val Ala Lys Tyr Phe Pro Thr Ala Ile Val Ser Gly Arg Ser
            150                 155                 160

cgt aag aag gtg ttt gaa ttt gta aaa ctg acg gaa ctg tac tac gct      765
Arg Lys Lys Val Phe Glu Phe Val Lys Leu Thr Glu Leu Tyr Tyr Ala
```

```
        165                 170                 175

ggt agt cac ggg atg gac ata gtg aca tct gca gca gca cat gct act      813
Gly Ser His Gly Met Asp Ile Val Thr Ser Ala Ala Ala His Ala Thr
    180                 185                 190

gaa aag tgc aaa gaa gcc aat ctc ttc caa cct gct tgc gag ttt ctc      861
Glu Lys Cys Lys Glu Ala Asn Leu Phe Gln Pro Ala Cys Glu Phe Leu
195                 200                 205                 210

cct atg att aat gag gtt tcc aag tgc ctc gtg gag gtc acg agt tca      909
Pro Met Ile Asn Glu Val Ser Lys Cys Leu Val Glu Val Thr Ser Ser
                215                 220                 225

att gaa ggt gca aga gtt gag aac aac aag ttc tgt gta tct gta cat      957
Ile Glu Gly Ala Arg Val Glu Asn Asn Lys Phe Cys Val Ser Val His
            230                 235                 240

tac cgc aac gta gca gag aag gac tgg aaa gtg gtc gca gga ctc gtg     1005
Tyr Arg Asn Val Ala Glu Lys Asp Trp Lys Val Val Ala Gly Leu Val
        245                 250                 255

aaa caa gtc ttg gag gcc ttc cct cgt ctc aaa gta acc aac ggg cga     1053
Lys Gln Val Leu Glu Ala Phe Pro Arg Leu Lys Val Thr Asn Gly Arg
    260                 265                 270

atg gtt tta gag gtt cgc ccg gtg atc gac tgg gac aag gga aag gct     1101
Met Val Leu Glu Val Arg Pro Val Ile Asp Trp Asp Lys Gly Lys Ala
275                 280                 285                 290

gtc gag ttc ctg ctt cgg tcg ctc ggc cta agc gac tcc gaa gat gtg     1149
Val Glu Phe Leu Leu Arg Ser Leu Gly Leu Ser Asp Ser Glu Asp Val
                295                 300                 305

gtt cct atc tac atc gga gac gat cga aca gac gaa gac gcc ttc aag     1197
Val Pro Ile Tyr Ile Gly Asp Asp Arg Thr Asp Glu Asp Ala Phe Lys
            310                 315                 320

gta ctg cga gag cga agc tgt gga tac gga atc cta gtc tcg cag gtg     1245
Val Leu Arg Glu Arg Ser Cys Gly Tyr Gly Ile Leu Val Ser Gln Val
        325                 330                 335

ccc aag gac act gaa gcc ttc tac tcg gtg aga gac ccg tct gaa gtg     1293
Pro Lys Asp Thr Glu Ala Phe Tyr Ser Val Arg Asp Pro Ser Glu Val
    340                 345                 350

atg ggg ttc ctc aat tcc ttg gtg aga tgg aag aag cac ccg ctg         1338
Met Gly Phe Leu Asn Ser Leu Val Arg Trp Lys Lys His Pro Leu
355                 360                 365

tgacgcaact gaaaacacaa cgactgattc agaagccgta aagcgactgt acttcgtgcg   1398

gcggcaattt tgtagagttt ttggctcacc gggtggctca ttctttcatg cgtttttatt   1458

ttttattttt ttaactgtca cagtccttcg tcactgagaa ataacaagtg gttgtcccac   1518

accctcttgc aactgtaatc tgtaagcaag aggccctccc tgttcggtct atatatatat   1578

attgaataaa accgggacgc ttttgccttg ccctg                              1613


<210> SEQ ID NO 16
<211> LENGTH: 369
<212> TYPE: PRT
<213> ORGANISM: Zea mays

<400> SEQUENCE: 16

Met Asp Met Gly Ser Gly Ser Ser Pro Val Ile Thr Asp Pro Ile Ser
1               5                   10                  15

Ile Ser Pro Pro Leu Leu Gly Gly Leu Thr Ser Asn Leu Met Pro Phe
            20                  25                  30

Ser Val Met Ser Gly Gly Cys Ser Ser Ser Pro Ser Met Ser Ala Ser
        35                  40                  45

Ser Arg Arg Lys Ile Glu Glu Val Leu Val Asn Gly Leu Leu Asp Ala
    50                  55                  60
```

-continued

```
Met Lys Ser Ser Ser Pro Arg Lys Lys His Asn Leu Ala Phe Gly Gln
65                  70                  75                  80

Asp Asn Ser Pro Asp Glu Asp Pro Ala Tyr Thr Ala Trp Leu Ser Lys
                85                  90                  95

Cys Pro Ser Ala Leu Ala Ser Phe Lys Gln Ile Val Ala Asn Ala Gln
            100                 105                 110

Gly Arg Arg Ile Ala Val Phe Leu Asp Tyr Asp Gly Thr Leu Ser Pro
        115                 120                 125

Ile Val Asp Asp Pro Asp Lys Ala Phe Met Ser Pro Val Met Arg Ala
    130                 135                 140

Ala Val Arg Asn Val Ala Lys Tyr Phe Pro Thr Ala Ile Val Ser Gly
145                 150                 155                 160

Arg Ser Arg Lys Lys Val Phe Glu Phe Val Lys Leu Thr Glu Leu Tyr
                165                 170                 175

Tyr Ala Gly Ser His Gly Met Asp Ile Val Thr Ser Ala Ala Ala His
            180                 185                 190

Ala Thr Glu Lys Cys Lys Glu Ala Asn Leu Phe Gln Pro Ala Cys Glu
        195                 200                 205

Phe Leu Pro Met Ile Asn Glu Val Ser Lys Cys Leu Val Glu Val Thr
    210                 215                 220

Ser Ser Ile Glu Gly Ala Arg Val Glu Asn Asn Lys Phe Cys Val Ser
225                 230                 235                 240

Val His Tyr Arg Asn Val Ala Glu Lys Asp Trp Lys Val Val Ala Gly
                245                 250                 255

Leu Val Lys Gln Val Leu Glu Ala Phe Pro Arg Leu Lys Val Thr Asn
            260                 265                 270

Gly Arg Met Val Leu Glu Val Arg Pro Val Ile Asp Trp Asp Lys Gly
        275                 280                 285

Lys Ala Val Glu Phe Leu Leu Arg Ser Leu Gly Leu Ser Asp Ser Glu
    290                 295                 300

Asp Val Val Pro Ile Tyr Ile Gly Asp Asp Arg Thr Asp Glu Asp Ala
305                 310                 315                 320

Phe Lys Val Leu Arg Glu Arg Ser Cys Gly Tyr Gly Ile Leu Val Ser
                325                 330                 335

Gln Val Pro Lys Asp Thr Glu Ala Phe Tyr Ser Val Arg Asp Pro Ser
            340                 345                 350

Glu Val Met Gly Phe Leu Asn Ser Leu Val Arg Trp Lys Lys His Pro
        355                 360                 365

Leu


<210> SEQ ID NO 17
<211> LENGTH: 1053
<212> TYPE: DNA
<213> ORGANISM: Oryza sativa
<220> FEATURE:
<221> NAME/KEY: CDS
<222> LOCATION: (2)..(643)
<223> OTHER INFORMATION:

<400> SEQUENCE: 17

t aca gcc tct tct tct tgg ggt gtt ctt gac tgg aag gtt tct ttg gtg      49
  Thr Ala Ser Ser Ser Trp Gly Val Leu Asp Trp Lys Val Ser Leu Val
  1               5                   10                  15

atg gcg aag gcg agc gag acg atg cgg atg gcc gtg cgc agc gtg gcg        97
Met Ala Lys Ala Ser Glu Thr Met Arg Met Ala Val Arg Ser Val Ala
            20                  25                  30
```

-continued

```
aag cac ttc ccg acg gcg atc gtg agc ggg cgg tgc cgc gac aag gtg      145
Lys His Phe Pro Thr Ala Ile Val Ser Gly Arg Cys Arg Asp Lys Val
        35                  40                  45

ttc gag ttc gtg aag ctc gcc gag ctg tac tac gcg ggg agc cac ggc      193
Phe Glu Phe Val Lys Leu Ala Glu Leu Tyr Tyr Ala Gly Ser His Gly
    50                  55                  60

atg gac atc aag ggc ccc gcc tcc cgc cac gcc gcc gcc aag tct cct      241
Met Asp Ile Lys Gly Pro Ala Ser Arg His Ala Ala Ala Lys Ser Pro
65                  70                  75                  80

ccc cac aac aag gga gtc ctc ttc cag ccg gcc agc gag ttc ctc ccc      289
Pro His Asn Lys Gly Val Leu Phe Gln Pro Ala Ser Glu Phe Leu Pro
                85                  90                  95

atg atc gag cag gtg cac cag cga ctc gag cag gcc acc agc tcc atc      337
Met Ile Glu Gln Val His Gln Arg Leu Glu Gln Ala Thr Ser Ser Ile
            100                 105                 110

ccg ggc gcc aag gtc gag aac aac aag ttc tgc gtc tcc gtc cac ttc      385
Pro Gly Ala Lys Val Glu Asn Asn Lys Phe Cys Val Ser Val His Phe
        115                 120                 125

cgg tgc gtc gag ttc ctc ctc gac tcg ctc ggt ttc gcc gac tgc agc      433
Arg Cys Val Glu Phe Leu Leu Asp Ser Leu Gly Phe Ala Asp Cys Ser
    130                 135                 140

gac gtg ctg ccg gtc tac atc ggc gac gac cgc acg gac gag gac gcg      481
Asp Val Leu Pro Val Tyr Ile Gly Asp Asp Arg Thr Asp Glu Asp Ala
145                 150                 155                 160

ttc aag gtt ttg cgg cgg cgt ggg cag ggc gtg ggg atc ctg gtg tcc      529
Phe Lys Val Leu Arg Arg Arg Gly Gln Gly Val Gly Ile Leu Val Ser
                165                 170                 175

aag cac ccc aag gag acg agc gcc tcc ttc tcc ctc cag gag ccc gcc      577
Lys His Pro Lys Glu Thr Ser Ala Ser Phe Ser Leu Gln Glu Pro Ala
            180                 185                 190

gag gtg atg gag ttc ttg ctg cgg ctc gtg gag tgg aat cgc ctg tcc      625
Glu Val Met Glu Phe Leu Leu Arg Leu Val Glu Trp Asn Arg Leu Ser
        195                 200                 205

agg aca cgg ttg agg ctg taacaattga atttaaccgg cgaggctagc             673
Arg Thr Arg Leu Arg Leu
    210

tagagagaag cgcgtgatct gggccgtcca agcgattaca tcggcagggt aacccgtgac    733

gctgatcgat cgtggattct acaccaacac aggtgctcga aaatggtgtc cacattgcag    793

aagcgcagag agctaattaa tcaacgacgg acgagagaaa ctgatggctg tctggccatt    853

gttgtgccat aatcctgttt agttcttcac ctttctccct tcttcttttt tcccatttgg    913

ggcccccctt ttggtaccaa ccatgtaaat tccgtactac tagtaccttg tcatgcacaa    973

gaggaagatc aatgcaaata atgaagagca actaatgcaa gtatatactc atcaaaaaaa   1033

aaaaaaaaaa aaaaaaaaaa                                                1053


<210> SEQ ID NO 18
<211> LENGTH: 214
<212> TYPE: PRT
<213> ORGANISM: Oryza sativa

<400> SEQUENCE: 18

Thr Ala Ser Ser Ser Trp Gly Val Leu Asp Trp Lys Val Ser Leu Val
1               5                   10                  15

Met Ala Lys Ala Ser Glu Thr Met Arg Met Ala Val Arg Ser Val Ala
            20                  25                  30

Lys His Phe Pro Thr Ala Ile Val Ser Gly Arg Cys Arg Asp Lys Val
        35                  40                  45
```

```
Phe Glu Phe Val Lys Leu Ala Glu Leu Tyr Tyr Ala Gly Ser His Gly
    50                  55                  60

Met Asp Ile Lys Gly Pro Ala Ser Arg His Ala Ala Ala Lys Ser Pro
65                  70                  75                  80

Pro His Asn Lys Gly Val Leu Phe Gln Pro Ala Ser Glu Phe Leu Pro
                85                  90                  95

Met Ile Glu Gln Val His Gln Arg Leu Glu Gln Ala Thr Ser Ser Ile
            100                 105                 110

Pro Gly Ala Lys Val Glu Asn Asn Lys Phe Cys Val Ser Val His Phe
        115                 120                 125

Arg Cys Val Glu Phe Leu Leu Asp Ser Leu Gly Phe Ala Asp Cys Ser
    130                 135                 140

Asp Val Leu Pro Val Tyr Ile Gly Asp Asp Arg Thr Asp Glu Asp Ala
145                 150                 155                 160

Phe Lys Val Leu Arg Arg Arg Gly Gln Gly Val Gly Ile Leu Val Ser
                165                 170                 175

Lys His Pro Lys Glu Thr Ser Ala Ser Phe Ser Leu Gln Glu Pro Ala
            180                 185                 190

Glu Val Met Glu Phe Leu Leu Arg Leu Val Glu Trp Asn Arg Leu Ser
        195                 200                 205

Arg Thr Arg Leu Arg Leu
    210


<210> SEQ ID NO 19
<211> LENGTH: 1904
<212> TYPE: DNA
<213> ORGANISM: Glycine max
<220> FEATURE:
<221> NAME/KEY: CDS
<222> LOCATION: (262)..(1407)
<223> OTHER INFORMATION:

<400> SEQUENCE: 19

gctttctctt ttcagttctc ttctcctctc tgcgcgacac agcacttcgt cactttcctt      60

tttttccatt ctcatagcgt ttttgtgttt tcaagcaagc gagtacggaa ctcatctgtt     120

gataaactgc tacctcaagc agtgacaaga aaagtggtgg aagtttgata gactttatag     180

ttcaatttgt tctgaatact ccttaaaaaa aaggtcttac attgttgctg cactgtgaaa     240

ttgtgcatag acctggatcc a atg gac ctg aag cca aat ctt aac cct gtc       291
                        Met Asp Leu Lys Pro Asn Leu Asn Pro Val
                        1               5                   10

ctt act gat gcc aca ccc tta aca agg tca agg ctg ggt gtg cct tct       339
Leu Thr Asp Ala Thr Pro Leu Thr Arg Ser Arg Leu Gly Val Pro Ser
                15                  20                  25

ggt tta tca cct tac tct cct ata ggg gca acc ttt ccc cat ggt aac       387
Gly Leu Ser Pro Tyr Ser Pro Ile Gly Ala Thr Phe Pro His Gly Asn
            30                  35                  40

atg ctg gca att cca agg aag aag aca gga att ctt gac gat ttt cgt       435
Met Leu Ala Ile Pro Arg Lys Lys Thr Gly Ile Leu Asp Asp Phe Arg
        45                  50                  55

tct agc ggt tgg ctc gat gca atg aaa tcg tct tct cct act cac act       483
Ser Ser Gly Trp Leu Asp Ala Met Lys Ser Ser Ser Pro Thr His Thr
    60                  65                  70

aag gta tcc aag gat gtt agt cat ggg att gga tca cct gat tct gct       531
Lys Val Ser Lys Asp Val Ser His Gly Ile Gly Ser Pro Asp Ser Ala
75                  80                  85                  90

tat agt acc tgg ctg cta aag ttt cca tca gca cta gca tct ttt gat       579
```

-continued

```
Tyr Ser Thr Trp Leu Leu Lys Phe Pro Ser Ala Leu Ala Ser Phe Asp
                95                  100                 105

caa att acc aac tgt gca aaa ggg aag aga ata gca ttg ttt ctg gat      627
Gln Ile Thr Asn Cys Ala Lys Gly Lys Arg Ile Ala Leu Phe Leu Asp
            110                 115                 120

tat gat ggg act ctt tca ccc att gtg gat aat cct gac tct gct ttc      675
Tyr Asp Gly Thr Leu Ser Pro Ile Val Asp Asn Pro Asp Ser Ala Phe
        125                 130                 135

atg tca gac aat atg cgt gct gct gtt aaa ata gtg gcg gaa tat ttt      723
Met Ser Asp Asn Met Arg Ala Ala Val Lys Ile Val Ala Glu Tyr Phe
    140                 145                 150

cca acc gcg ata att agt gga aga agc cgt gac aag gta tat gaa ttt      771
Pro Thr Ala Ile Ile Ser Gly Arg Ser Arg Asp Lys Val Tyr Glu Phe
155                 160                 165                 170

gtt gga gta agt gat cta tgt tat gct ggt agt cat ggt atg gac att      819
Val Gly Val Ser Asp Leu Cys Tyr Ala Gly Ser His Gly Met Asp Ile
                175                 180                 185

att ggt cct tct aga caa tct att tct gat aat cac cct gat tgc att      867
Ile Gly Pro Ser Arg Gln Ser Ile Ser Asp Asn His Pro Asp Cys Ile
            190                 195                 200

agt tct gct gac aag cag ggt gtt gaa gtt aat tta ttc caa cct gct      915
Ser Ser Ala Asp Lys Gln Gly Val Glu Val Asn Leu Phe Gln Pro Ala
        205                 210                 215

gct gaa ttc ctg ccc atg att aat gag gta ctt ggg ttg ctc atg gag      963
Ala Glu Phe Leu Pro Met Ile Asn Glu Val Leu Gly Leu Leu Met Glu
    220                 225                 230

tgc aca gaa gat att gaa gga gca aca gtt gag aac aac aaa ttt tgt     1011
Cys Thr Glu Asp Ile Glu Gly Ala Thr Val Glu Asn Asn Lys Phe Cys
235                 240                 245                 250

gtg tct gtg cat tac cgc aat gta gat gag gag agt tgg caa att gtg     1059
Val Ser Val His Tyr Arg Asn Val Asp Glu Glu Ser Trp Gln Ile Val
                255                 260                 265

gga caa cgt gta tat gat gtt ctg aag gag tat cca cgt ttg cgt tta     1107
Gly Gln Arg Val Tyr Asp Val Leu Lys Glu Tyr Pro Arg Leu Arg Leu
            270                 275                 280

act cat ggg cgg aag gtt tta gag gtt cgg cca gtg att gac tgg gat     1155
Thr His Gly Arg Lys Val Leu Glu Val Arg Pro Val Ile Asp Trp Asp
        285                 290                 295

aag gga aaa gct gtc aca ttt tta ctc gag tca ctt gga ctt aat tgt     1203
Lys Gly Lys Ala Val Thr Phe Leu Leu Glu Ser Leu Gly Leu Asn Cys
    300                 305                 310

gat gac gtg ctc gct att tat gtt ggg gat gat aga aca gat gaa gat     1251
Asp Asp Val Leu Ala Ile Tyr Val Gly Asp Asp Arg Thr Asp Glu Asp
315                 320                 325                 330

gca ttt aag gtt ttg aaa gaa gct aat aaa ggt tgt ggc atc tta gtg     1299
Ala Phe Lys Val Leu Lys Glu Ala Asn Lys Gly Cys Gly Ile Leu Val
                335                 340                 345

tcc cgt gcc cca aaa gaa agc aac gca att tac tct ctt cgt gat ccc     1347
Ser Arg Ala Pro Lys Glu Ser Asn Ala Ile Tyr Ser Leu Arg Asp Pro
            350                 355                 360

tct gag gtc atg gaa ttt ctg aca tca ctt gcg gaa tgg aaa tca agc     1395
Ser Glu Val Met Glu Phe Leu Thr Ser Leu Ala Glu Trp Lys Ser Ser
        365                 370                 375

att caa gct cgc tgaaaagatt tacatattgt atagaggaga acatactcca         1447
Ile Gln Ala Arg
    380

ctatgctata tattagagac agtcttttgt ttttagtttg aattttttgt tagaagactt   1507

tccaagaggt ctgctggaac atatttgagc tcagaagacc tctgacctga cgacagcaac   1567
```

-continued

```
aacattgtca ttacccaatt gttttactca aattttgtgt ggtagctgta aattcctggc   1627

tgagaattat atatatatat atatattggg aagattaagg aaaatctcct catagggtgt   1687

ttcttttttc cgcattagaa gtttattatc gtattcattt catatccttt cttcagtttt   1747

ggttactgac cagctcattg ggattaaat atgaaactgt tctgtttctt ttttttgaga   1807

gaatatataa ttttttaata tgtagattgg atatcattat ttgtattacc aatttatatc   1867

agtctgatta ccgttacata aaaaaaaaaa aaaaaaa                            1904
```

```
<210> SEQ ID NO 20
<211> LENGTH: 382
<212> TYPE: PRT
<213> ORGANISM: Glycine max

<400> SEQUENCE: 20

Met Asp Leu Lys Pro Asn Leu Asn Pro Val Leu Thr Asp Ala Thr Pro
1               5                   10                  15

Leu Thr Arg Ser Arg Leu Gly Val Pro Ser Gly Leu Ser Pro Tyr Ser
            20                  25                  30

Pro Ile Gly Ala Thr Phe Pro His Gly Asn Met Leu Ala Ile Pro Arg
        35                  40                  45

Lys Lys Thr Gly Ile Leu Asp Asp Phe Arg Ser Ser Gly Trp Leu Asp
    50                  55                  60

Ala Met Lys Ser Ser Ser Pro Thr His Thr Lys Val Ser Lys Asp Val
65                  70                  75                  80

Ser His Gly Ile Gly Ser Pro Asp Ser Ala Tyr Ser Thr Trp Leu Leu
                85                  90                  95

Lys Phe Pro Ser Ala Leu Ala Ser Phe Asp Gln Ile Thr Asn Cys Ala
            100                 105                 110

Lys Gly Lys Arg Ile Ala Leu Phe Leu Asp Tyr Asp Gly Thr Leu Ser
        115                 120                 125

Pro Ile Val Asp Asn Pro Asp Ser Ala Phe Met Ser Asp Asn Met Arg
    130                 135                 140

Ala Ala Val Lys Ile Val Ala Glu Tyr Phe Pro Thr Ala Ile Ile Ser
145                 150                 155                 160

Gly Arg Ser Arg Asp Lys Val Tyr Glu Phe Val Gly Val Ser Asp Leu
                165                 170                 175

Cys Tyr Ala Gly Ser His Gly Met Asp Ile Ile Gly Pro Ser Arg Gln
            180                 185                 190

Ser Ile Ser Asp Asn His Pro Asp Cys Ile Ser Ser Ala Asp Lys Gln
        195                 200                 205

Gly Val Glu Val Asn Leu Phe Gln Pro Ala Ala Glu Phe Leu Pro Met
    210                 215                 220

Ile Asn Glu Val Leu Gly Leu Leu Met Glu Cys Thr Glu Asp Ile Glu
225                 230                 235                 240

Gly Ala Thr Val Glu Asn Asn Lys Phe Cys Val Ser Val His Tyr Arg
                245                 250                 255

Asn Val Asp Glu Glu Ser Trp Gln Ile Val Gly Gln Arg Val Tyr Asp
            260                 265                 270

Val Leu Lys Glu Tyr Pro Arg Leu Arg Leu Thr His Gly Arg Lys Val
        275                 280                 285

Leu Glu Val Arg Pro Val Ile Asp Trp Asp Lys Gly Lys Ala Val Thr
    290                 295                 300

Phe Leu Leu Glu Ser Leu Gly Leu Asn Cys Asp Asp Val Leu Ala Ile
305                 310                 315                 320
```

```
Tyr Val Gly Asp Asp Arg Thr Asp Glu Asp Ala Phe Lys Val Leu Lys
                325                 330                 335

Glu Ala Asn Lys Gly Cys Gly Ile Leu Val Ser Arg Ala Pro Lys Glu
            340                 345                 350

Ser Asn Ala Ile Tyr Ser Leu Arg Asp Pro Ser Glu Val Met Glu Phe
        355                 360                 365

Leu Thr Ser Leu Ala Glu Trp Lys Ser Ser Ile Gln Ala Arg
    370                 375                 380


<210> SEQ ID NO 21
<211> LENGTH: 1383
<212> TYPE: DNA
<213> ORGANISM: Glycine max
<220> FEATURE:
<221> NAME/KEY: CDS
<222> LOCATION: (3)..(1091)
<223> OTHER INFORMATION:

<400> SEQUENCE: 21

cc ctt gtg gag ttg gca atg tcg att tca aac aca agt gct cta cct       47
   Leu Val Glu Leu Ala Met Ser Ile Ser Asn Thr Ser Ala Leu Pro
   1               5                   10                  15

aga gct acg gtg cct gga ata atg gcc ttg ctt ggt ggg gtt ttg ggc      95
Arg Ala Thr Val Pro Gly Ile Met Ala Leu Leu Gly Gly Val Leu Gly
                20                  25                  30

cta ccc cag aag aag ctc tta atg aaa act ttg gaa gat gga agt gtt     143
Leu Pro Gln Lys Lys Leu Leu Met Lys Thr Leu Glu Asp Gly Ser Val
            35                  40                  45

aat aaa gga ggg acc aaa gtt att aac aca tgg att gat tca atg aga     191
Asn Lys Gly Gly Thr Lys Val Ile Asn Thr Trp Ile Asp Ser Met Arg
        50                  55                  60

gcc tct tct ccc aca cga gtc aaa tcc aca caa aac caa gac cca aca     239
Ala Ser Ser Pro Thr Arg Val Lys Ser Thr Gln Asn Gln Asp Pro Thr
    65                  70                  75

agt cct tgg aca ctt tac cac cct tcg gca ctg agc atg ttt gat cag     287
Ser Pro Trp Thr Leu Tyr His Pro Ser Ala Leu Ser Met Phe Asp Gln
80                  85                  90                  95

att gta tgt gag tcc aaa gga aag cag att gtg act ttt ctt gac tat     335
Ile Val Cys Glu Ser Lys Gly Lys Gln Ile Val Thr Phe Leu Asp Tyr
                100                 105                 110

gat gga act ctc tcc cca att gtt gca gat cca gat aaa gca tac atg     383
Asp Gly Thr Leu Ser Pro Ile Val Ala Asp Pro Asp Lys Ala Tyr Met
            115                 120                 125

agt aaa aag atg agg acc aca ttg aag gac tta gca agg cat ttc ccc     431
Ser Lys Lys Met Arg Thr Thr Leu Lys Asp Leu Ala Arg His Phe Pro
        130                 135                 140

act gcc atc gtg agt gga agg tgc ctg gac aag gtg tat aac ttt gta     479
Thr Ala Ile Val Ser Gly Arg Cys Leu Asp Lys Val Tyr Asn Phe Val
    145                 150                 155

aga ttg gca gaa ctg tac tat gct ggg agc cat gga atg gac atc aag     527
Arg Leu Ala Glu Leu Tyr Tyr Ala Gly Ser His Gly Met Asp Ile Lys
160                 165                 170                 175

gga cca aca aat aag cga agt act aag aag gaa aat gaa caa gtg ctc     575
Gly Pro Thr Asn Lys Arg Ser Thr Lys Lys Glu Asn Glu Gln Val Leu
                180                 185                 190

ttc caa ccc gct agt gaa ttc ttg ccc atg atc aat gag gtg tac aac     623
Phe Gln Pro Ala Ser Glu Phe Leu Pro Met Ile Asn Glu Val Tyr Asn
            195                 200                 205

atc ttg gtg gaa aaa aca aag tct gtc cct ggg gct aag gta gaa aat     671
Ile Leu Val Glu Lys Thr Lys Ser Val Pro Gly Ala Lys Val Glu Asn
```

-continued

```
        210                 215                 220

aac aag ttt tgc ttg tcc gtg cac ttt cgc tgt gtt gac gaa aag agt      719
Asn Lys Phe Cys Leu Ser Val His Phe Arg Cys Val Asp Glu Lys Ser
    225                 230                 235

tgg gtg tca ttg gct gaa caa gtg agc ttc gtg ctc aac gag tac cca      767
Trp Val Ser Leu Ala Glu Gln Val Ser Phe Val Leu Asn Glu Tyr Pro
240                 245                 250                 255

aaa ctt aag cta act caa ggg aga aaa gtg ctt gag att cga cca acc      815
Lys Leu Lys Leu Thr Gln Gly Arg Lys Val Leu Glu Ile Arg Pro Thr
                260                 265                 270

ata aaa tgg gac aag ggc aag gct ctt gaa ttc ttg cta gag tca ctg      863
Ile Lys Trp Asp Lys Gly Lys Ala Leu Glu Phe Leu Leu Glu Ser Leu
            275                 280                 285

gga tat gct aat tct gat aat gta ttt cca atc tat att ggg gat gat      911
Gly Tyr Ala Asn Ser Asp Asn Val Phe Pro Ile Tyr Ile Gly Asp Asp
        290                 295                 300

cga act gat gaa gat gct ttt aag gtt tta cgg agg agg ggt cat ggg      959
Arg Thr Asp Glu Asp Ala Phe Lys Val Leu Arg Arg Arg Gly His Gly
    305                 310                 315

gtt ggg att cta gtt tct aaa att cca aaa gaa act gat gct tcc tac     1007
Val Gly Ile Leu Val Ser Lys Ile Pro Lys Glu Thr Asp Ala Ser Tyr
320                 325                 330                 335

act ttg caa gat cca aca gag gtt ggg cag ttt ttg agg cat ttg gtg     1055
Thr Leu Gln Asp Pro Thr Glu Val Gly Gln Phe Leu Arg His Leu Val
                340                 345                 350

gag tgg aaa aga acg agt tcc caa tac cac aag ttg tagattctta          1101
Glu Trp Lys Arg Thr Ser Ser Gln Tyr His Lys Leu
            355                 360

gatgaattca gggaaattga caccagccca taatttggtc aaggggtggt tccaattata   1161

tccctttct tgttcgaaat aggaaatagt gtgttccata atttaaagtt ttagggagga    1221

acaaagttga aatagctagc taggttctct ctctattttc tttttctaat gtaatctatt   1281

ccatcacacg tttgcatgcg catgcggata gtgaaagaat tgatgtttta tgccgcaatt   1341

gcgagtggcg cgtcaaaaaa aaaaaaaaaa aaaaaaaaaa aa                      1383


<210> SEQ ID NO 22
<211> LENGTH: 363
<212> TYPE: PRT
<213> ORGANISM: Glycine max

<400> SEQUENCE: 22

Leu Val Glu Leu Ala Met Ser Ile Ser Asn Thr Ser Ala Leu Pro Arg
1               5                   10                  15

Ala Thr Val Pro Gly Ile Met Ala Leu Leu Gly Gly Val Leu Gly Leu
            20                  25                  30

Pro Gln Lys Lys Leu Leu Met Lys Thr Leu Glu Asp Gly Ser Val Asn
        35                  40                  45

Lys Gly Gly Thr Lys Val Ile Asn Thr Trp Ile Asp Ser Met Arg Ala
    50                  55                  60

Ser Ser Pro Thr Arg Val Lys Ser Thr Gln Asn Gln Asp Pro Thr Ser
65                  70                  75                  80

Pro Trp Thr Leu Tyr His Pro Ser Ala Leu Ser Met Phe Asp Gln Ile
                85                  90                  95

Val Cys Glu Ser Lys Gly Lys Gln Ile Val Thr Phe Leu Asp Tyr Asp
            100                 105                 110

Gly Thr Leu Ser Pro Ile Val Ala Asp Pro Asp Lys Ala Tyr Met Ser
        115                 120                 125
```

```
Lys Lys Met Arg Thr Thr Leu Lys Asp Leu Ala Arg His Phe Pro Thr
    130                 135                 140

Ala Ile Val Ser Gly Arg Cys Leu Asp Lys Val Tyr Asn Phe Val Arg
145                 150                 155                 160

Leu Ala Glu Leu Tyr Tyr Ala Gly Ser His Gly Met Asp Ile Lys Gly
                165                 170                 175

Pro Thr Asn Lys Arg Ser Thr Lys Lys Glu Asn Glu Gln Val Leu Phe
            180                 185                 190

Gln Pro Ala Ser Glu Phe Leu Pro Met Ile Asn Glu Val Tyr Asn Ile
        195                 200                 205

Leu Val Glu Lys Thr Lys Ser Val Pro Gly Ala Lys Val Glu Asn Asn
    210                 215                 220

Lys Phe Cys Leu Ser Val His Phe Arg Cys Val Asp Glu Lys Ser Trp
225                 230                 235                 240

Val Ser Leu Ala Glu Gln Val Ser Phe Val Leu Asn Glu Tyr Pro Lys
                245                 250                 255

Leu Lys Leu Thr Gln Gly Arg Lys Val Leu Glu Ile Arg Pro Thr Ile
            260                 265                 270

Lys Trp Asp Lys Gly Lys Ala Leu Glu Phe Leu Leu Glu Ser Leu Gly
        275                 280                 285

Tyr Ala Asn Ser Asp Asn Val Phe Pro Ile Tyr Ile Gly Asp Asp Arg
    290                 295                 300

Thr Asp Glu Asp Ala Phe Lys Val Leu Arg Arg Arg Gly His Gly Val
305                 310                 315                 320

Gly Ile Leu Val Ser Lys Ile Pro Lys Glu Thr Asp Ala Ser Tyr Thr
                325                 330                 335

Leu Gln Asp Pro Thr Glu Val Gly Gln Phe Leu Arg His Leu Val Glu
            340                 345                 350

Trp Lys Arg Thr Ser Ser Gln Tyr His Lys Leu
        355                 360


<210> SEQ ID NO 23
<211> LENGTH: 924
<212> TYPE: DNA
<213> ORGANISM: Triticum aestivum
<220> FEATURE:
<221> NAME/KEY: CDS
<222> LOCATION: (2)..(679)
<223> OTHER INFORMATION:

<400> SEQUENCE: 23

g aga aac gtc gcc aag tac ttc cct gct gcc atc gtc agc gga agg tcc      49
  Arg Asn Val Ala Lys Tyr Phe Pro Ala Ala Ile Val Ser Gly Arg Ser
  1               5                   10                  15

cgg aag aag gtt ctt gaa ttc gta aaa ctg aag gaa ctc tgc tat gct       97
Arg Lys Lys Val Leu Glu Phe Val Lys Leu Lys Glu Leu Cys Tyr Ala
            20                  25                  30

ggt agt cat ggg atg gac ata atg aca tct tct tca gca cat tat gaa      145
Gly Ser His Gly Met Asp Ile Met Thr Ser Ser Ser Ala His Tyr Glu
        35                  40                  45

cgc aat gct gaa aag ggc aaa gaa gcc aac ctc ttc caa cct gct cgc      193
Arg Asn Ala Glu Lys Gly Lys Glu Ala Asn Leu Phe Gln Pro Ala Arg
    50                  55                  60

gat ttt ctg cct atg atc gat gag gtt tcc aag gtc ctc ttg gaa gtc      241
Asp Phe Leu Pro Met Ile Asp Glu Val Ser Lys Val Leu Leu Glu Val
65                  70                  75                  80

acg agc cga atc gaa ggc gca agc gtt gag gac aac aag ttc tgc gtg      289
```

```
Thr Ser Arg Ile Glu Gly Ala Ser Val Glu Asp Asn Lys Phe Cys Val
                85                  90                  95

tct gta cat tac cgc aac gtg gac gag aag gac tgg gag ctg gtc gca      337
Ser Val His Tyr Arg Asn Val Asp Glu Lys Asp Trp Glu Leu Val Ala
            100                 105                 110

cgg ctc gta aac gaa gtg ctg gag gac ttc ccc cgt ctc aaa gtg acc      385
Arg Leu Val Asn Glu Val Leu Glu Asp Phe Pro Arg Leu Lys Val Thr
        115                 120                 125

aac gga cga atg gtt tta gag gtt cgt cca gtg atc gac tgg gac aag      433
Asn Gly Arg Met Val Leu Glu Val Arg Pro Val Ile Asp Trp Asp Lys
    130                 135                 140

ggg aag gcc gtc gag ttc ctg ctt cag tcg ctc ggg ctg agc gac tcc      481
Gly Lys Ala Val Glu Phe Leu Leu Gln Ser Leu Gly Leu Ser Asp Ser
145                 150                 155                 160

gag aaa gtg atc cct atc tac atc ggc gac gac cgc acc gac gaa gac      529
Glu Lys Val Ile Pro Ile Tyr Ile Gly Asp Asp Arg Thr Asp Glu Asp
                165                 170                 175

gcg ttc aag gtg ctt cgg gag agg aac tgc gga tac ggg ata ctg gtc      577
Ala Phe Lys Val Leu Arg Glu Arg Asn Cys Gly Tyr Gly Ile Leu Val
            180                 185                 190

tcg cag gcg ccc aag gaa acc gag gcc ttc tac tcg ctc agg gac ccg      625
Ser Gln Ala Pro Lys Glu Thr Glu Ala Phe Tyr Ser Leu Arg Asp Pro
        195                 200                 205

tct gaa gtg atg gag ttc ctg aac tcc ttg gtg aga tgg aag aag cac      673
Ser Glu Val Met Glu Phe Leu Asn Ser Leu Val Arg Trp Lys Lys His
    210                 215                 220

tcg cta tgaacaaaca ggagatgact gtagtttccg aggcgacagt tttgcagcgt      729
Ser Leu
225

tggaaaccat agctagggtc gaatgatgtt gccgtcccct gttaattcgt ttaggtcgat    789

tgatattctt gtactgctag tcatgttctt tgccactgag aaatttgatc ggtggctgtg    849

ttggttgtta tacataatgc tttaggttaa caaaaaaaaa aaaaaaaaaa aaaaaaaaaa    909

aaaaaaaaaa aaaaa                                                      924


<210> SEQ ID NO 24
<211> LENGTH: 226
<212> TYPE: PRT
<213> ORGANISM: Triticum aestivum

<400> SEQUENCE: 24

Arg Asn Val Ala Lys Tyr Phe Pro Ala Ala Ile Val Ser Gly Arg Ser
1               5                   10                  15

Arg Lys Lys Val Leu Glu Phe Val Lys Leu Lys Glu Leu Cys Tyr Ala
            20                  25                  30

Gly Ser His Gly Met Asp Ile Met Thr Ser Ser Ser Ala His Tyr Glu
        35                  40                  45

Arg Asn Ala Glu Lys Gly Lys Glu Ala Asn Leu Phe Gln Pro Ala Arg
    50                  55                  60

Asp Phe Leu Pro Met Ile Asp Glu Val Ser Lys Val Leu Leu Glu Val
65                  70                  75                  80

Thr Ser Arg Ile Glu Gly Ala Ser Val Glu Asp Asn Lys Phe Cys Val
                85                  90                  95

Ser Val His Tyr Arg Asn Val Asp Glu Lys Asp Trp Glu Leu Val Ala
            100                 105                 110

Arg Leu Val Asn Glu Val Leu Glu Asp Phe Pro Arg Leu Lys Val Thr
        115                 120                 125
```

-continued

```
Asn Gly Arg Met Val Leu Glu Val Arg Pro Val Ile Asp Trp Asp Lys
    130                 135                 140

Gly Lys Ala Val Glu Phe Leu Leu Gln Ser Leu Gly Leu Ser Asp Ser
145                 150                 155                 160

Glu Lys Val Ile Pro Ile Tyr Ile Gly Asp Asp Arg Thr Asp Glu Asp
                165                 170                 175

Ala Phe Lys Val Leu Arg Glu Arg Asn Cys Gly Tyr Gly Ile Leu Val
            180                 185                 190

Ser Gln Ala Pro Lys Glu Thr Glu Ala Phe Tyr Ser Leu Arg Asp Pro
        195                 200                 205

Ser Glu Val Met Glu Phe Leu Asn Ser Leu Val Arg Trp Lys Lys His
    210                 215                 220

Ser Leu
225


<210> SEQ ID NO 25
<211> LENGTH: 529
<212> TYPE: DNA
<213> ORGANISM: Glycine max
<220> FEATURE:
<221> NAME/KEY: unsure
<222> LOCATION: (493)
<223> OTHER INFORMATION: n is a, c, g or t
<220> FEATURE:
<221> NAME/KEY: unsure
<222> LOCATION: (507)
<223> OTHER INFORMATION: n is a, c, g or t

<400> SEQUENCE: 25

cctcaactcg ttattgtaca agtacgagtc ggatatttac actgccatcg agcaagtctt     60

tgggggtgaa ctcgaaatgg acgaagagtt tgaactctcg ccatggccca tcactgctga    120

ggctttcgcc gagggtgctg cacgtgaact ctcgacatcc cgcgttcaaa cggcggccga    180

gtggaaggaa cgcatggata agcgtcgtga tacgatgaat gagctctgct ggaatgaggg    240

acgaggaatg ttctttgact gggataccaa ggcgcagaaa caggccaaat acgagagtgt    300

tacctgtctc tggccactct gggctggaaa tgcgtccgag gatcaggcaa tgaagatggt    360

caatatggct ctacccaagt ttgaggtcgc tggcgggctt gtttcgggaa cagaggagag    420

ccgaggtatc atctcgatcg atcgaccgaa tcgacagtgg gattaacctt tcaagctggc    480

cgccgcatca gantatgact tgggtcnggc ttgacgatac ggcacgata               529


<210> SEQ ID NO 26
<211> LENGTH: 30
<212> TYPE: PRT
<213> ORGANISM: Glycine max

<400> SEQUENCE: 26

Leu Asn Ser Leu Leu Tyr Lys Tyr Glu Ser Asp Ile Tyr Thr Ala Ile
  1               5                  10                  15

Glu Gln Val Phe Gly Gly Glu Leu Glu Met Asp Glu Glu Phe
             20                  25                  30


<210> SEQ ID NO 27
<211> LENGTH: 461
<212> TYPE: DNA
<213> ORGANISM: Triticum aestivum
<220> FEATURE:
<221> NAME/KEY: unsure
<222> LOCATION: (432)
<223> OTHER INFORMATION: n is a, c, g or t
<220> FEATURE:
```

-continued

<221> NAME/KEY: unsure
<222> LOCATION: (461)
<223> OTHER INFORMATION: n is a, c, g or t

<400> SEQUENCE: 27
caagcactac atgtggccgc tcctccacta cctgctcccg ctcacgccct ccacgctcgg 60
ggggctgccc ttcgaccgcg cgctctacca ctccttcctc tccgccaacc gcgccttcgc 120
cgaccgcctc accgaggtgc tcgcccccga cgacgacttc gtctggatcc aggactacca 180
cctcctcgcc ctccccacct tcctccgcaa gcgcttcccg cgcgccaggg tcggattctt 240
cctccactcg cccttcccct cctccgagat cttccgcacc atccccgtcc gcgacgacct 300
gctccgcgcc ctcctcaacg ccgacctcgt cggcttccac accttcgact acgcgcgcca 360
cttcctttcg gctgctcccg cctcctcggc tcgactacag tcaaagcgcg gataatcggc 420
atcgagtata anggcgcacg tcaacgtcaa gattctgccg n 461

<210> SEQ ID NO 28
<211> LENGTH: 120
<212> TYPE: PRT
<213> ORGANISM: Triticum aestivum

<400> SEQUENCE: 28

Met Trp Pro Leu Leu His Tyr Leu Leu Pro Leu Thr Pro Ser Thr Leu
1 5 10 15

Gly Gly Leu Pro Phe Asp Arg Ala Leu Tyr His Ser Phe Leu Ser Ala
20 25 30

Asn Arg Ala Phe Ala Asp Arg Leu Thr Glu Leu Ala Pro Asp Asp Asp
35 40 45

Phe Val Trp Ile Gln Asp Tyr His Leu Leu Ala Leu Pro Thr Phe Leu
50 55 60

Arg Lys Arg Phe Pro Arg Ala Arg Val Gly Phe Phe Leu His Ser Pro
65 70 75 80

Phe Pro Ser Ser Glu Ile Phe Arg Thr Ile Pro Val Arg Asp Asp Leu
85 90 95

Leu Arg Ala Leu Leu Asn Ala Asp Leu Val Gly Phe His Thr Phe Asp
100 105 110

Tyr Ala Arg His Phe Leu Ser Ala
115 120

<210> SEQ ID NO 29
<211> LENGTH: 447
<212> TYPE: DNA
<213> ORGANISM: Oryza sativa

<400> SEQUENCE: 29
tacagcctct tcttcttggg gtgttcttga ctggaaggtt tctttggtga tggcgaaggc 60
gagcgagacg atgcggatgg ccgtgcgcag cgtggcgaag cacttcccga cggcgatcgt 120
gagcgggcgg tgccgcgaca aggtgttcga gttcgtgaag ctcgccgagc tgtactacgc 180
ggggagccac ggcatggaca tcaagggccc cgcctcccgc cacgccgccg ccaagtctcc 240
tccccacaac aagggagtcc tcttccagcc ggccagcgag ttcctcccca tgatcgagca 300
ggtgcaccaa gcgactcgag caggcaccaa gctccatccc gggcgccaag tcgagaacaa 360
caattctgcg tctccgtcca cttccggtgc gtcgattcct cctcgactcg ctcggtttcg 420
ccgactgcag cgactgctgc cggtcta 447

<210> SEQ ID NO 30
<211> LENGTH: 54
<212> TYPE: PRT
<213> ORGANISM: Oryza sativa

<400> SEQUENCE: 30

```
Ala Lys Ala Ser Glu Thr Met Arg Met Ala Val Arg Ser Val Ala Lys
  1               5                  10                  15

His Phe Pro Thr Ala Ile Val Ser Gly Arg Cys Arg Asp Lys Val Phe
             20                  25                  30

Glu Phe Val Lys Leu Ala Glu Leu Tyr Tyr Ala Gly Ser His Gly Met
         35                  40                  45

Asp Ile Lys Gly Pro Ala
     50
```

<210> SEQ ID NO 31
<211> LENGTH: 492
<212> TYPE: DNA
<213> ORGANISM: Glycine max
<220> FEATURE:
<221> NAME/KEY: unsure
<222> LOCATION: (384)
<223> OTHER INFORMATION: n is a, c, g or t
<220> FEATURE:
<221> NAME/KEY: unsure
<222> LOCATION: (435)
<223> OTHER INFORMATION: n is a, c, g or t
<220> FEATURE:
<221> NAME/KEY: unsure
<222> LOCATION: (488)
<223> OTHER INFORMATION: n is a, c, g or t

<400> SEQUENCE: 31

```
gctttctctt ttcagttctc ttctcctctc tgcgcgacac agcacttcgt cactttcctt     60

tttttccatt ctcatagcgt ttttgtgttt tcaagcaagc gagtacggaa ctcatctgtt    120

gataaactgc tacctcaagc agtgacaaga aaagtggtgg aagtttgata gactttatag    180

ttcaatttgt tctgaatact ccttaaaaaa aaggtcttac attgttgctg cactgtgaaa    240

ttgtgcatag acctggatcc aatggacctg aagccaaatc ttaaccctgt ccttactgat    300

gccacaccct taacaaggtc aaggctgggt gtgccttctg gtttatcacc ttactctcct    360

ataggggcaa cctttcccca tggnaacatg ctggcaattc caaggaagaa gacaggaatt    420

cttgacgatt ttcgntctag cggttggctc gatgcaatga aatcgtcttc tcctactcac    480

actaaggnat cc                                                        492
```

<210> SEQ ID NO 32
<211> LENGTH: 30
<212> TYPE: PRT
<213> ORGANISM: Glycine max

<400> SEQUENCE: 32

```
Asn Pro Val Leu Thr Asp Ala Thr Pro Leu Thr Arg Ser Arg Leu Gly
  1               5                  10                  15

Val Pro Ser Gly Leu Ser Pro Tyr Ser Pro Ile Gly Ala Thr
             20                  25                  30
```

<210> SEQ ID NO 33
<211> LENGTH: 541
<212> TYPE: DNA
<213> ORGANISM: Glycine max
<220> FEATURE:
<221> NAME/KEY: unsure
<222> LOCATION: (415)

```
<223> OTHER INFORMATION: n is a, c, g or t
<220> FEATURE:
<221> NAME/KEY: unsure
<222> LOCATION: (453)
<223> OTHER INFORMATION: n is a, c, g or t
<220> FEATURE:
<221> NAME/KEY: unsure
<222> LOCATION: (469)
<223> OTHER INFORMATION: n is a, c, g or t
<220> FEATURE:
<221> NAME/KEY: unsure
<222> LOCATION: (520)
<223> OTHER INFORMATION: n is a, c, g or t

<400> SEQUENCE: 33

cccttgtgga gttggcaatg tcgatttcaa acacaagtgc tctacctaga gctacggtgc     60

ctggaataat ggccttgctt ggtggggttt tgggcctacc ccagaagaag ctcttaatga    120

aaactttgga agatggaagt gttaataaag gagggaccaa agttattaac acatggattg    180

attcaatgag agcctcttct cccacacgag tcaaatccac acaaaaccaa gacccaacaa    240

gtccttggac actttaccac ccttcggcac tgagcatgtt tgatcagatt gtatgtgagt    300

ccaaaggaaa gcagattgtg acttttcttg actatgatgg aactctctcc ccaattgttg    360

cagatccaag ataaagcata catgagtaaa aagatgagga ccacattgaa ggacntagca    420

aggcatttcc ccactgccaa ccgtgagtgg aangtgcctg ggacaaggng tataactttg    480

gaaagattgg caaaactgta ctaagctggg agccatgggn atgggcatca agggaacaac    540

a                                                                    541


<210> SEQ ID NO 34
<211> LENGTH: 90
<212> TYPE: PRT
<213> ORGANISM: Glycine max

<400> SEQUENCE: 34

Pro Gln Lys Lys Leu Leu Met Lys Thr Leu Glu Asp Gly Ser Val Asn
  1               5                  10                  15

Lys Gly Gly Thr Lys Val Ile Asn Thr Trp Ile Asp Ser Met Arg Ala
             20                  25                  30

Ser Ser Pro Thr Arg Val Lys Ser Thr Gln Asn Gln Asp Pro Thr Ser
         35                  40                  45

Pro Trp Thr Leu Tyr His Pro Ser Ala Leu Ser Met Phe Asp Gln Ile
     50                  55                  60

Val Cys Glu Ser Lys Gly Lys Gln Ile Val Thr Phe Leu Asp Tyr Asp
 65                  70                  75                  80

Gly Thr Leu Ser Pro Ile Val Ala Asp Pro
                 85                  90


<210> SEQ ID NO 35
<211> LENGTH: 516
<212> TYPE: DNA
<213> ORGANISM: Triticum aestivum
<220> FEATURE:
<221> NAME/KEY: unsure
<222> LOCATION: (407)
<223> OTHER INFORMATION: n is a, c, g or t
<220> FEATURE:
<221> NAME/KEY: unsure
<222> LOCATION: (452)
<223> OTHER INFORMATION: n is a, c, g or t
<220> FEATURE:
<221> NAME/KEY: unsure
<222> LOCATION: (471)
<223> OTHER INFORMATION: n is a, c, g or t
```

-continued

<220> FEATURE:
<221> NAME/KEY: unsure
<222> LOCATION: (478)
<223> OTHER INFORMATION: n is a, c, g or t
<220> FEATURE:
<221> NAME/KEY: unsure
<222> LOCATION: (493)
<223> OTHER INFORMATION: n is a, c, g or t
<220> FEATURE:
<221> NAME/KEY: unsure
<222> LOCATION: (502)
<223> OTHER INFORMATION: n is a, c, g or t

<400> SEQUENCE: 35

```
gagaaacgtc gccaagtact tccctgctgc catcgtcagc ggaaggtccc ggaagaaggt     60

tcttgaattc gtaaaactga aggaactctg ctatgctggt agtcatggga tggacataat    120

gacatcttct tcagcacatt atgaacgcaa tgctgaaaag ggcaaagaag ccaacctctt    180

ccaacctgct cgcgattttc tgcctatgat cgatgaggtt tccaaggtcc tcttggaagt    240

cacgagccga atcgaaggcg caagcgttga ggacaacaag ttctgcgtgt ctgtacatta    300

ccgcaacgtg gacgagaagg actggggagc tggtcccacg gctcgtaaac gaatgctgga    360

ggacttcccc gtctcaaagt gaccaacgga cgaatggttt taaaagntcg tcaagtgatt    420

gactgggaca aggggaaggc cttcaatttc cngcttaatc cccccgggct naccaacncc    480

gagaaaagtg atncctatcc anatcgggga cgaccg                             516
```

<210> SEQ ID NO 36
<211> LENGTH: 41
<212> TYPE: PRT
<213> ORGANISM: Triticum aestivum

<400> SEQUENCE: 36

```
Arg Asn Val Ala Lys Tyr Phe Pro Ala Ala Ile Val Ser Gly Arg Ser
  1               5                  10                  15

Arg Lys Lys Val Leu Glu Phe Val Lys Leu Lys Glu Leu Cys Tyr Ala
             20                  25                  30

Gly Ser His Gly Met Asp Ile Met Thr
         35                  40
```

<210> SEQ ID NO 37
<211> LENGTH: 385
<212> TYPE: PRT
<213> ORGANISM: Arabidopsis thaliana

<400> SEQUENCE: 37

```
Met Asp Met Lys Ser Gly His Ser Ser Pro Val Met Thr Asp Ser Pro
1               5                   10                  15

Pro Ile Ser Asn Ser Arg Leu Thr Ile Arg Gln Asn Arg Leu Pro Tyr
            20                  25                  30

Ser Ser Ala Ala Ala Thr Ala Ile Ser Gln Asn Asn Asn Leu Leu Leu
        35                  40                  45

Thr Val Pro Arg Lys Lys Thr Gly Ile Leu Asp Asp Val Lys Ser Asn
    50                  55                  60

Gly Trp Leu Asp Ala Met Lys Ser Ser Ser Pro Pro Pro Thr Ile Leu
65                  70                  75                  80

Asn Lys Asp Asn Leu Ser Asn Asp Ala Thr Asp Met Thr Tyr Arg Glu
            85                  90                  95

Trp Met Gln Leu Lys Tyr Pro Ser Ala Leu Thr Ser Phe Glu Lys Ile
            100                 105                 110
```

-continued

```
Met Ser Phe Ala Lys Gly Lys Arg Ile Ala Leu Phe Leu Asp Tyr Asp
        115                 120                 125

Gly Thr Leu Ser Pro Ile Val Glu Glu Pro Asp Cys Ala Tyr Met Ser
    130                 135                 140

Ser Ala Met Arg Ser Ala Val Gln Asn Val Ala Lys Tyr Phe Pro Thr
145                 150                 155                 160

Ala Ile Ile Ser Gly Arg Ser Arg Asp Lys Val Tyr Glu Phe Val Asn
                165                 170                 175

Leu Ser Glu Leu Tyr Tyr Ala Gly Ser His Gly Met Asp Ile Met Ser
            180                 185                 190

Pro Ala Gly Glu Ser Leu Asn His Glu His Ser Arg Thr Val Ser Val
        195                 200                 205

Tyr Glu Gln Gly Lys Asp Val Asn Leu Phe Gln Pro Ala Ser Glu Phe
    210                 215                 220

Leu Pro Met Ile Asp Lys Val Leu Cys Ser Leu Ile Glu Ser Thr Lys
225                 230                 235                 240

Asp Ile Lys Gly Val Lys Val Glu Asp Asn Lys Phe Cys Ile Ser Val
                245                 250                 255

His Tyr Arg Asn Val Glu Glu Lys Asn Trp Thr Leu Val Ala Gln Cys
            260                 265                 270

Val Asp Asp Val Ile Arg Thr Tyr Pro Lys Leu Arg Leu Thr His Gly
        275                 280                 285

Arg Lys Val Leu Glu Ile Arg Pro Val Ile Asp Trp Asp Lys Gly Lys
    290                 295                 300

Ala Val Thr Phe Leu Leu Glu Ser Leu Gly Leu Asn Asn Cys Glu Asp
305                 310                 315                 320

Val Leu Pro Ile Tyr Val Gly Asp Asp Arg Thr Asp Glu Asp Ala Phe
                325                 330                 335

Lys Val Leu Arg Asp Gly Pro Asn His Gly Tyr Gly Ile Leu Val Ser
            340                 345                 350

Ala Val Pro Lys Asp Ser Asn Ala Phe Tyr Ser Leu Arg Asp Pro Ser
        355                 360                 365

Glu Val Met Glu Phe Leu Lys Ser Leu Val Thr Trp Lys Arg Ser Met
    370                 375                 380

Gly
385


<210> SEQ ID NO 38
<211> LENGTH: 374
<212> TYPE: PRT
<213> ORGANISM: Arabidopsis thaliana

<400> SEQUENCE: 38

Met Thr Asn Gln Asn Val Ile Val Ser Asp Arg Lys Pro Ile Leu Gly
1               5                   10                  15

Leu Lys Thr Ile Thr Val Ser Val Ser Asn Ser Pro Leu Phe Ser Asn
            20                  25                  30

Ser Phe Pro Thr Tyr Phe Asn Phe Pro Arg Arg Lys Leu Leu Lys Leu
        35                  40                  45

Leu Glu Ala Ala Asp Lys Asn Asn Leu Val Val Ala Pro Lys Ile Thr
    50                  55                  60

Ser Met Ile Asp Ser Met Arg Asp Ser Ser Pro Thr Arg Leu Arg Ser
65                  70                  75                  80

Ser Ser Tyr Asp Ser Asp Ser Asp Asn Asp Asp Lys Thr Ser Trp Ile
                85                  90                  95
```

-continued

```
Val Arg Phe Pro Ser Ala Leu Asn Met Phe Asp Glu Ile Val Asn Ala
            100                 105                 110

Ala Lys Gly Lys Gln Ile Val Met Phe Leu Asp Tyr Asp Gly Thr Leu
        115                 120                 125

Ser Pro Ile Val Glu Asp Pro Asp Lys Ala Phe Ile Thr His Glu Met
    130                 135                 140

Arg Glu Val Val Lys Asp Val Ala Ser Asn Phe Pro Thr Ala Ile Val
145                 150                 155                 160

Thr Gly Arg Ser Ile Glu Lys Val Arg Ser Phe Val Gln Val Asn Glu
                165                 170                 175

Ile Tyr Tyr Ala Gly Ser His Gly Met Asp Ile Glu Gly Pro Thr Asn
            180                 185                 190

Glu Asn Ser Asn Gly Gln Ser Asn Glu Arg Val Leu Phe Gln Pro Ala
        195                 200                 205

Arg Glu Phe Leu Pro Met Ile Glu Lys Val Val Asn Ile Leu Glu Glu
    210                 215                 220

Lys Thr Lys Trp Ile Pro Gly Ala Met Val Glu Asn Asn Lys Phe Cys
225                 230                 235                 240

Leu Ser Val His Phe Arg Arg Val Asp Glu Lys Arg Trp Pro Ala Leu
                245                 250                 255

Ala Glu Val Val Lys Ser Val Leu Ile Asp Tyr Pro Lys Leu Lys Leu
            260                 265                 270

Thr Gln Gly Arg Lys Val Leu Glu Ile Arg Pro Thr Ile Lys Trp Asp
        275                 280                 285

Lys Gly Gln Ala Leu Asn Phe Leu Leu Lys Ser Leu Gly Tyr Glu Asn
    290                 295                 300

Ser Asp Asp Val Val Pro Val Tyr Ile Gly Asp Asp Arg Thr Asp Glu
305                 310                 315                 320

Asp Ala Phe Lys Val Leu Arg Glu Arg Gly Gln Gly Phe Gly Ile Leu
                325                 330                 335

Val Ser Lys Val Pro Lys Asp Thr Asn Ala Ser Tyr Ser Leu Gln Asp
            340                 345                 350

Pro Ser Gln Val Asn Lys Phe Leu Glu Arg Leu Val Glu Trp Lys Arg
        355                 360                 365

Lys Thr Val Gly Glu Glu
    370
```